United States Patent
Nagele

(10) Patent No.: US 10,132,817 B2
(45) Date of Patent: Nov. 20, 2018

(54) DIAGNOSTIC BIOMARKER PROFILES FOR THE DETECTION AND DIAGNOSIS OF ALZHEIMER'S DISEASE

(75) Inventor: Robert G. Nagele, Turnersville, NJ (US)

(73) Assignee: Rowan University, Glassboro, NJ (US)

( * ) Notice: Subject to any disclaimer, the term of this patent is extended or adjusted under 35 U.S.C. 154(b) by 0 days.

(21) Appl. No.: 14/232,347

(22) PCT Filed: Jul. 12, 2012

(86) PCT No.: PCT/US2012/046502
§ 371 (c)(1),
(2), (4) Date: Jul. 7, 2014

(87) PCT Pub. No.: WO2013/010003
PCT Pub. Date: Jan. 17, 2013

(65) Prior Publication Data
US 2014/0315736 A1    Oct. 23, 2014

Related U.S. Application Data

(60) Provisional application No. 61/507,006, filed on Jul. 12, 2011.

(51) Int. Cl.
G01N 33/68 (2006.01)
G01N 33/564 (2006.01)
G01N 33/543 (2006.01)

(52) U.S. Cl.
CPC ....... *G01N 33/6896* (2013.01); *G01N 33/564* (2013.01); *G01N 33/54306* (2013.01); *G01N 2800/2821* (2013.01)

(58) Field of Classification Search
CPC ........ C12Q 2600/158; C12Q 2600/178; C12Q 1/6883; C12Q 1/6886; C12Q 2600/118; A61K 31/517; G06F 19/18; G06F 19/24; G01N 33/564; G01N 33/54306; G01N 33/6896; G01N 2800/2821
See application file for complete search history.

(56) References Cited

U.S. PATENT DOCUMENTS

| | | |
|---|---|---|
| 2005/0112116 A1 | 5/2005 | Lennon et al. |
| 2008/0254482 A1 | 10/2008 | Mattoon et al. |
| 2009/0258792 A1 | 10/2009 | Wang et al. |
| 2009/0317837 A1 | 12/2009 | Wong et al. |
| 2010/0035360 A1 | 2/2010 | Mikoshiba |

FOREIGN PATENT DOCUMENTS

| | | |
|---|---|---|
| CN | 1910456 A | 2/2007 |
| WO | 02/10753 A2 | 2/2002 |
| WO | 20061121912 A2 | 11/2006 |
| WO | 2008/122432 A1 | 10/2008 |
| WO | 2010/028248 A1 | 3/2010 |
| WO | 2011/028912 A2 | 3/2011 |

OTHER PUBLICATIONS

Life Technologies Corporation, Absolute identification of novel autoimmune biomarkers ProtoArray® Human Protein Microarrays, published 2009. Retrieved online <https://www.lifetechnologies.com/us/en/home/life-science/protein-biology/protein-assays-analysis/protein-microarrays/immune-response-biomarker-profiling-irbp.html> Retrieved on Jul. 27, 2015.*
Strausberg et al., Proc. Natl. Acad. Sci. U.S.A. 99 (26), 16899-16903, 2002.*
Invitrogen brochure "Absolute identification of novel autoimmune biomarkers", published 2009 [online] Retrieved from <https://www.thermofisher.com/us/en/home/life-science/protein-biology/protein-assays-analysis/protein-microarrays/technical-resources.html> Retrieved on Feb. 4, 2016.*
Version 5.0 Protein Content list v5.0 [Excel spreadsheet, online] Retrieved from <https://www.thermofisher.com/us/en/home/life-science/protein-biology/protein-assays-analysis/protein-microarrays/technical-resources.html> Retrieved on Feb. 4, 2016.*
Wuchty et al. "Prediction of Associations between microRNAs and Gene Expression in Glioma Biology", PlosONE; Feb. 16, 2011; vol. 6, No. 2; p. 1-10.
Nelson "Alzheimer Pathology in Elderly Patients With Glioblastoma Multiforme"; Arch Pathol Lab Med; Dec. 2002; vol. 126; p. 1515-1517.
International Search Report dated Oct. 10, 2012, in Application No. PCT/US2012/046502.
International Preliminary Report on Patentability dated Jan. 14, 2014, in Application No. PCT/US2012/046502.
Altman et al., "Insect cells as hosts for the expression of recombinant glycoproteins," Glycoconj J, 1999, vol. 16, pp. 109-•123 (Abstract only).
Bahr et al., "Amyloid beta protein is internalized selectively by hippocampal field CA1 and causes neurons to accumulate amyloidogenic carboxyterminal fragments of the amyloid precursor protein," J Comp Neurol., 1998, vol. 397, No. 1, pp. 139-147 (Abstract only).
Bouras et al., "Humoral immunity in brain aging and Alzheimer's disease," Brain Res Brain Res Rev, 2005, vol. 48, No. 3, pp. 477-487 (Abstract only).
Clifford et al., "Abeta peptides can enter the brain through a defective blood-brain barrier and bind selectively to neurons," Brain Res., 2007, vol. 1142, pp. 223-236 (Abstract only).
D'Andrea et al., "Evidence that neurones accumulating amyloid can undergo lysis to form amyloid plaques in Alzheimer's disease," Histopathology, 2001, vol. 38, pp. 120-134 (Abstract only).
D'Andrea, "Evidence linking neuronal cell death to autoimmunity in Alzheimer's disease," Brain Res, 2003, vol. 982, No. 1, pp. 19-30 (Abstract only).

(Continued)

*Primary Examiner* — Kimberly Ballard
*Assistant Examiner* — Stacey N MacFarlane
(74) *Attorney, Agent, or Firm* — Saul Ewing Arnstein & Lehr LLP; Domingos J. Silva

(57) ABSTRACT

The present invention provides methods, compositions and kits for the detection of Alzheimer's disease (AD) diagnostic biomarkers, for the diagnosis of AD, for the identification of a subject at risk for developing AD, and for the generation of patient-specific AD diagnostic biomarker profiles.

6 Claims, 1 Drawing Sheet

(56) References Cited

OTHER PUBLICATIONS

Deane and Zlokovic, "Role of the blood-brain barrier in the pathogenesis of Alzheimer's disease," Curr Alzheimer Res., 2007, vol. 4, pp. 191-97 (abstract only).
Franceschi et al., "Neuron-binding antibodies in Alzheimer's disease and Down's syndrome," J Gerontol., 1989, vol. 44, No. 4, pp. M128-M130 (Abstract only).
Gouras et al., "Intraneuronal Ab42 accumulation in human brain," Am J Pathol, Jan. 2000, vol. 156, No. 1, pp. 15-20.
Hall et al., "Protein Microarray Technology," Mech Ageing Dev, Jan. 2007, vol. 128, No. 1, pp. 161-167.
Harris-White et al., "Effects of transforming growth factor-ß (isoforms 1-3) on amyloid-ß deposition, inflammation, and cell targeting in organotypic hippocampal slice cultures," J Neurosci., 1998, vol. 18, pp. 10366-10374.
He et al., "Single step generation of protein arrays from DNA by cell-free expression and in situ immobilisation (PISA method)" Nucleic Acids Res, 2001, vol. 29, No. 15, pp. e73-3.
He et al., "In situ synthesis of protein arrays," Curr. Opin Biotechnol, Feb. 2008, vol. 19, No. 1, pp. 4-9 (Abstract only).
He et al., "Printing protein arrays from DNA arrays," Nature Methods, 2008, vol. 5, No. 2, pp. 175-177 (Abstract only).
Kalaria, "The blood-brain barrier and cerebrovascular pathology in Alzheimer's disease," Ann NY Acad Sci., 1999, vol. 893, pp. 113-125 (Abstract only).
Kulmala et al., "Brain reactive antibodies and the blood-brain barrier: observations in aging rodents and the effects of peripheral kainic acid," Exp Aging Res, 1987, vol. 13, No. 1-2, pp. 67-72 (Abstract only).
Li et al., "Expression of recombinant proteins in Pichia pastoris," Appl Biochem Biotechnol, 2007, vol. 142, pp. 105-124 (Abstract only).
Loeffler et al., "Immunocytochemical detection of anti-hippocampal antibodies in Alzheimer's disease and normal cerebrospinal fluid," Neurochem Res., 1997, vol. 22, No. 2, pp. 209-214 (Abstract only).
Malouf, AT, "Effect of beta amyloid peptides on neurons in hippocampal slice cultures," Neurobiol Aging, 1992, vol. 13, No. 5, pp. 543-551 (Abstract only).
Mecocci et al., "Antihistone and anti-dsDNA autoantibodies in Alzheimer's disease and vascular dementia," Biol Psychiatry, 1993, vol. 34, No. 6, pp. 380-385 (Abstract only).
Mecocci et al., "Serum anti-GFAP and anti-S100 autoantibodies in brain aging, Alzheimer's disease and vascular dementia," J Neuroimmunol, Mar. 1995, vol. 57, No. 1-2, pp. 165-170 (Abstract only).
Mooradian, "Effect of aging on the blood-brain barrier," Neurobiol Aging., Jan.-Feb. 1988, vol. 9, No. 1, pp. 31-39 (Abstract only).
Nagele et al., "Intracellular accumulation of beta-amyloid(1-42) in neurons is facilitated by the alpha 7 nicotinic acetylcholine receptor in Alzheimer's disease," Neuroscience, 2002, vol. 110, No. 2, pp. 199-211 (Abstract only).
Nandy et al., "Specificity of brain-reactive antibodies in serum of old mice," J Gerontol., May 1975, vol. 30, No. 3, pp. 269-274 (Abstract only).
Ramachandran et al., "On-chip protein synthesis for making microarrays," Methods Mol. Biol, 2006, vol. 328, pp. 1-14 (Abstract only).
Ramachandran et al., "Self-assembling protein microarrays," Science, 2004, vol. 305, No. 5680, pp. 86-90.
Ray et al., "Label-free detection techniques for protein microarrays: prospects, merits and challenges," Proteomics, Feb. 2010, vol. 10, No. 4, pp. 731-748 (Abstract only).
Schwab et al., "Inflammatory aspects of Alzheimer disease and other neurodegenerative disorders," J Alzheimers Dis, May 2008, vol. 13, No. 4, pp. 359-369 (Abstract only).
Selkoe, "Alzheimer's disease is a synaptic failure," Science, Oct. 2002, vol. 298, No. 5594, pp. 789-791 (Abstract only).
Spampinato et al., "Agonist-regulated internalization and desensitization of the human nociceptin receptor expressed in CHO cells," Curr Drug Targets, Jan. 2007, vol. 8, No. 1, pp. 137-146 (Abstract only).
Stein et al., "Circulating autoantibodies recognize and bind dying neurons following injury to the brain," J Neuropathol Exp Neurol, Dec. 2002, vol. 61, No. 12, pp. 1100-1108 (Abstract only).
Stoevesandt et al., "Protein microarrays: high-throughput tools for proteomics," Expert Rev Proteomics, Apr. 2009, vol. 6, No. 2, pp. 145-157 (Abstract only).
Stoppini et al., "A simple method for organotypic cultures of nervous tissue," J Neurosci Methods., Apr. 1991, vol. 37, No. 2, pp. 173-•82 (Abstract only).
Thal et al., "Cerebral amyloid angiopathy and its relationship to Alzheimer's disease," Acta Neuropathol, Jun. 2008, vol. 115, No. 6, pp. 599•-609 (Abstract only).
Tibshirani et al., "Diagnosis of multiple cancer types by shrunken centroids of gene expression," Proc Natl Acad Sci USA, May 2002, vol. 99, No. 10, pp. 6567-6572.
Venkateswar et al., "Neurocalcin delta modulation of ROS-GC1, a new model of Ca(2+) signaling," Biochemistry, 2008, vol. 47, pp. 6590-6601.
Weisman et al., "Interleukins, inflammation, and mechanisms of Alzheimer's disease," Vitam Horm. 2006, vol. 74, pp. 505-530 (Abstract only).
Weksler et al., "Do age-associated changes in 'physiologic' autoantibodies contribute to infection, atherosclerosis, and Alzheimer's disease?" Exp Gerontol, Aug.-Sep. 2002, vol. 37, No. 8-9, pp. 971-979 (Abstract only).
Zagorski et al., "Methodological and chemical factors affecting amyloid beta peptide amyloidogenicity," Methods Enzymol., 1999, vol. 309, pp. 189-204 (Abstract only).
K. Yanagawa et al: "Pathologic and immunologic profiles of a limited form of neuromyelitis optica with myelitis", Neurology, vol. 73, No. 20, Nov. 17, 2009 (Nov. 17, 2009), pp. 1628-1637.
Vernino Steven et al: "Autoimmune encephalopathies", Neurologist, vol. 13, No. 3, May 1, 2007 (May 1, 2007), pp. 140-147.
Kuboshima et al., Presence of serum tripartite motif-containing 21 antibodies in patients with esophageal squamous cell carcinoma, Cancer Science, May 2006, vol. 97, No. 5, pp. 380-386; abstract.

* cited by examiner

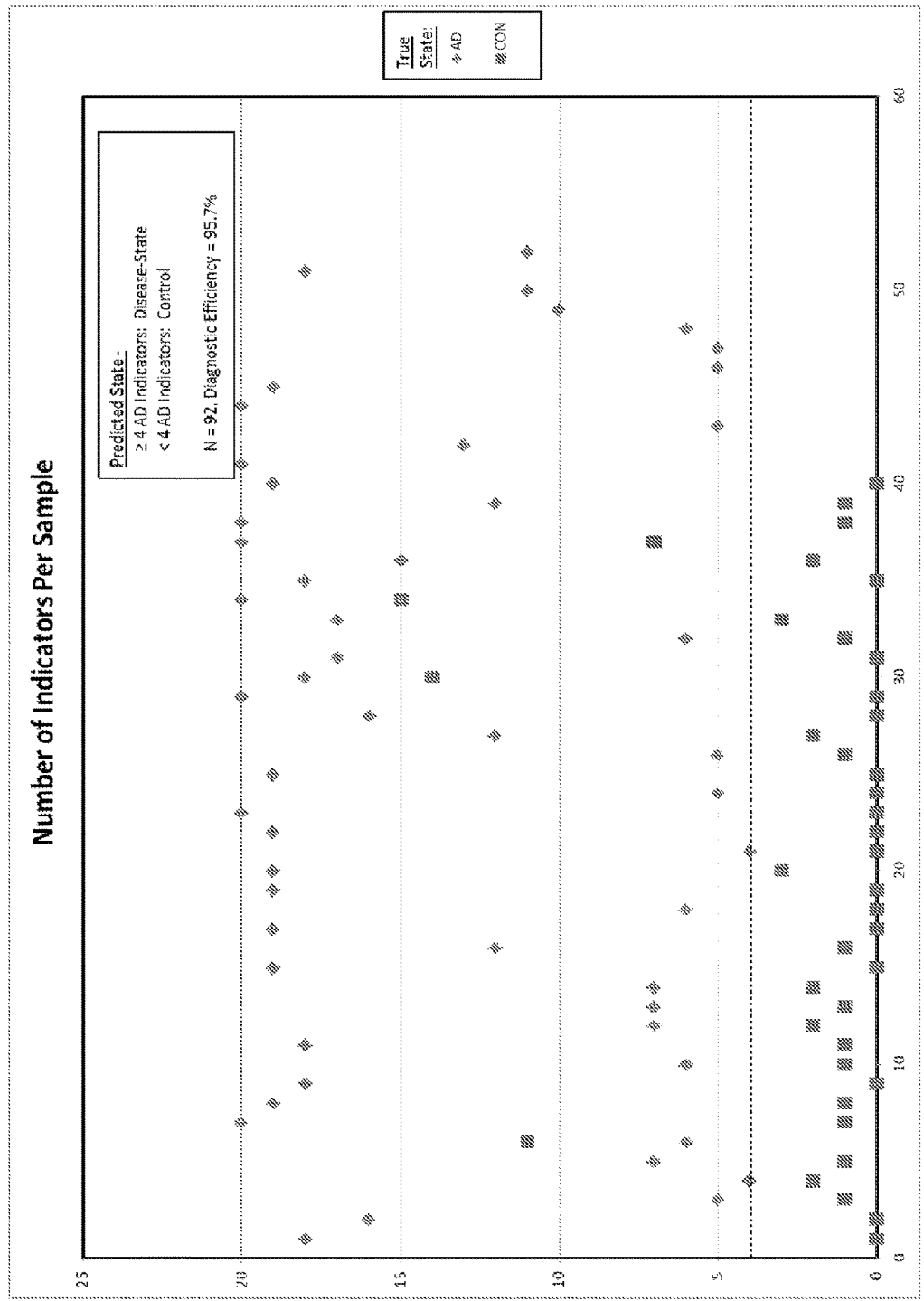

DIAGNOSTIC BIOMARKER PROFILES FOR THE DETECTION AND DIAGNOSIS OF ALZHEIMER'S DISEASE

The present application is the U.S. National Phase of International Patent Application Serial No. PCT/US12/46502, filed on Jul. 12, 2012, which claims priority to U.S. Provisional Application. No. 61/507,006 filed on Jul. 12, 2011. The contents of the foregoing applications are incorporated herein by reference in their entireties.

BACKGROUND OF THE INVENTION

Alzheimer's disease (AD) is a progressive and devastating neurodegenerative disorder of the elderly that is highlighted by a dramatic reduction of memory and cognition and linked to loss of neurons and synapses (Selkoe (2002) *Science* 298, 789-791). Additional key pathological features include the deposition of amyloid beta (Aβ), especially the 42-amino acid peptide (Aβ42), within neurons, amyloid plaques and in the walls of brain blood vessels, as well as the appearance of neurofibrillary tangles, glial activation and widespread inflammation (Schwab et al. (2008) *J Alzheimers Dis* 13, 359-369; Thal et al. (2008) *Acta Neuropathol* 115, 599-609; Weisman et al. (2006) *Vitam Horm* 74, 505-530). Aβ42 deposition within neurons is initiated early in the course of the disease, precedes amyloid plaque and tangle formation, and temporally and spatially coincides with loss of synapses in human AD and transgenic mouse brains (D'Andrea et al. (2001) *Histopathology* 38, 120-134; Nagele et al. (2002) *Neuroscience* 110, 199-211; Gouras et al. (2000) *Am J Pathol* 156, 15-20).

Studies have reported the presence of immunoglobulin (Ig)-immunopositive neurons in histological sections of post-mortem AD brains, which were only rarely observed in comparable brain regions of non-demented, age-matched controls (Stein et al. (2002) *J Neuropathol Exp Neurol* 61, 1100-1108; Bouras et al. (2005) *Brain Res Brain Res Rev* 48, 477-487; D'Andrea (2003) *Brain Res* 982, 19-30). The presence of specific brain-reactive autoantibodies in the serum of AD patients has also been reported. (Bouras et al. (2005) *Brain Res Brain Res Rev* 48, 477-487; Kulmala et al. (1987) *Exp Aging Res* 13, 67-72; Mecocci et al. (1993) *Biol Psychiatry* 34, 380-385; Mecocci et al. (1995) *J Neuroimmunol* 57, 165-170; Weksler et al. (2002) *Exp Gerontol* 37, 971-979).

BRIEF SUMMARY OF THE INVENTION

In one embodiment, the present invention provides a method for detecting AD diagnostic biomarkers in a subject in need of such detection comprising obtaining an immunoglobulin-containing biological sample from the subject, and performing an assay to determine the presence or absence of one or more AD diagnostic biomarkers in the biological sample.

In another embodiment, the present invention provides a method for diagnosing AD in a subject in need of such diagnosis comprising obtaining an immunoglobulin-containing biological sample from the subject, performing an assay to determine the presence or absence of one or more AD diagnostic biomarkers in the biological sample, and diagnosing AD if one or more AD diagnostic biomarkers are present.

In another embodiment, the present invention provides a method of identifying a subject at risk for developing a AD comprising obtaining an immunoglobulin-containing biological sample from the subject, performing an assay to determine the presence or absence of one or more AD diagnostic biomarkers in the biological sample, and identifying the subject as at risk for developing AD if one or more of the AD diagnostic biomarkers is present.

In another embodiment, the present invention provides a method of generating a patient-specific AD diagnostic biomarker profile comprising obtaining an immunoglobulin-containing biological sample from a patient, performing an assay to determine the presence or absence of one or more AD diagnostic biomarkers in the biological sample, and generating a patient-specific AD diagnostic biomarker profile of the AD diagnostic biomarkers present in the sample.

In yet another embodiment, the present invention provides a substrate on which one or more autoantigens that are specific for an AD diagnostic biomarker are immobilized.

The present invention provides, in another embodiment, a microarray comprising a substrate on which one or more autoantigens that are specific for an AD diagnostic biomarker are immobilized.

In a further embodiment, the present invention provides a kit for detecting AD-specific antibodies.

BRIEF DESCRIPTION OF THE DRAWING

The drawing displays a graphical representation of a diagnostic logic exemplified in Example 8.

DETAILED DESCRIPTION OF THE INVENTION

In accordance with the present invention, it has been discovered that brain-reactive autoantibodies are ubiquitous in the blood, and that these autoantibodies can enhance Aβ42 peptide deposition, a pathological hallmark of AD. It has further been discovered that brain-reactive autoantibodies are part of a much larger group of autoantibodies that are typically present in human sera, and that the expression of certain subsets of these autoantibodies is characteristically modulated by certain disease states such that disease-specific autoantibody patterns or profiles have been discovered and can be used as diagnostic biomarkers to detect and diagnose the presence of specific diseases such as AD. Among other embodiments, described herein is the use of these diagnostic biomarkers to accurately detect and diagnose AD based on their detection, identification and quantification revealed through interactions with their respective antigen targets on protein micro arrays.

AD diagnostic biomarkers are defined herein as antibodies that specifically bind to protein antigens and are diagnostic indicators that can be used to differentiate Alzheimer's Disease from control subjects without AD. The term "protein antigens" as used herein includes protein and peptide antigens. Protein antigens that have been identified as capable of being specifically bound by the AD diagnostic biomarkers are set forth in the following Table 1. The protein antigens in Table 1 are identified by art-accepted names as well as database identification numbers. The database identification numbers refer to the publically available protein databases of the National Center for Biotechnology Information (NCBI), which are well-known and accessible to those of ordinary skill in the art.

TABLE 1

| Database ID | Description |
|---|---|
| NM_024754.2 | pentatricopeptide repeat domain 2 (PTCD2) |
| BC051695.1 | FERM domain containing 8 (FRMD8) |
| NM_014280.1 | DnaJ homolog subfamily C member 8 |
| BC064984.1 | additional sex combs like 1 (*Drosophila*) (ASXL1) |
| NM_003384.1 | vaccinia related kinase 1 (VRK1) |
| NM_001544.2 | intercellular adhesion molecule 4 (Landsteiner-Wiener blood group) (ICAM4), transcript variant 1 |
| NM_001896.2 | casein kinase 2, alpha prime polypeptide (CSNK2A2) |
| NM_021104.1 | ribosomal protein L41 (RPL41), transcript variant 1 |
| BC016380.1 | cDNA clone MGC: 27376 IMAGE: 4688477, complete cds |
| NM_012387.1 | peptidyl arginine deiminase, type IV (PADI4) |
| NM_003135.1 | Signal recognition particle 19 kDa protein |
| BC022524.1 | fibroblast growth factor 12 (FGF12) |
| BC000758.1 | Coiled-coil domain-containing protein 28A |
| NM_021032.2 | fibroblast growth factor 12 (FGF12), transcript variant 1 |
| NM_022343.2 | Golgi-associated plant pathogenesis-related protein 1 |
| BC004236.2 | ubiquitin-conjugating enzyme E2S (UBE2S) |
| NM_000983.3 | 60S ribosomal protein L22 |
| NM_017588.1 | WD repeat domain 5 (WDR5), transcript variant 1 |
| NM_018956.2 | chromosome 9 open reading frame 9 (C9orf9) |
| BC033178.1 | immunoglobulin heavy constant gamma 3 (G3m marker) (IGHG3) |
| NM_006628.4 | cyclic AMP phosphoprotein, 19 kD (ARPP-19) |
| BC022098.1 | cDNA clone MGC: 31944 IMAGE: 4878869, complete cds |
| NM_001641.2 | APEX nuclease (multifunctional DNA repair enzyme) 1 (APEX1), transcript variant 1 |
| NM_003668.2 | mitogen-activated protein kinase-activated protein kinase 5 (MAPKAPK5), transcript variant 1 |
| NM_015933.1 | coiled-coil domain containing 72 (CCDC72) |
| PHC1244 | chemokine (C-C motif) ligand 19 (CCL19) |
| BC007782.2 | immunoglobulin lambda constant 1 (Mcg marker) (IGLC1) |
| BC006423.1 | Serine/threonine-protein kinase 6 |
| BC042628.1 | serpin peptidase inhibitor, clade E (nexin, plasminogen activator inhibitor type 1), member 2 (SERPINE2) |
| BC021561.1 | FACT complex subunit SPT16 |
| BC005248.1 | eukaryotic translation initiation factor 1A, Y-linked (EIF1AY) |
| NM_006223.1 | protein (peptidylprolyl cis/trans isomerase) NIMA-interacting, 4 (parvulin) (PIN4) |
| NM_032377.2 | elongation factor 1 homolog (*S. cerevisiae*) (ELOF1) |
| BC057774.1 | RNA (guanine-9-)-methyltransferase domain-containing protein 3 |
| NM_004196.2 | Cyclin-dependent kinase-like 1 |
| BC001662.1 | MAP kinase-activated protein kinase 3 |
| NM_015920.3 | 40S ribosomal protein S27-like protein |
| NM_001031.4 | 40S ribosomal protein S28 |
| NM_003688.1 | Peripheral plasma membrane protein CASK |
| BC048970.1 | tubulin tyrosine ligase-like family, member 7 (TTLL7) |
| NM_000984.2 | ribosomal protein L23a (RPL23A) |
| NM_018439.1 | Impact homolog (mouse) (IMPACT) |
| NM_002305.2 | lectin, galactoside-binding, soluble, 1 (galectin 1) (LGALS1) |
| BC056508.1 | variable charge, Y-linked 1B (VCY) |
| BC090938.1 | Ig gamma-1 chain C region |
| NM_002013.2 | FK506 binding protein 3, 25 kDa (FKBP3) |
| NM_007278.1 | GABA(A) receptor-associated protein (GABARAP) |
| BC007228.1 | CSAG family, member 3A (CSAG3A) |
| BC033758.1 | centaurin, alpha 2 (CENTA2) |
| BC092518.1 | Ig gamma-1 chain C region |
| BC019598.1 | Zinc finger matrin-type protein 4 |
| NM_145909.1 | Zinc finger protein 323 |
| NM_003516.2 | histone cluster 2, H2aa3 (HIST2H2AA3) |
| NM_006838.1 | methionyl aminopeptidase 2 (METAP2) |
| BC026038.1 | Ig gamma-1 chain C region |
| NM_002129.2 | high-mobility group box 2 (HMGB2) |
| NM_002677.1 | peripheral myelin protein 2 (PMP2) |
| BC001132.1 | DEAD (Asp-Glu-Ala-Asp) box polypeptide 54 (DDX54) |
| NM_001001794.1 | family with sequence similarity 116, member B (FAM116B) |
| NM_001997.2 | Finkel-Biskis-Reilly murine sarcoma virus (FBR-MuSV) ubiquitously expressed (FAU) |
| BC021174.1 | Small EDRK-rich factor 1 |
| NM_001028.2 | ribosomal protein S25 (RPS25) |
| NM_003512.3 | Histone H2A type 1-C |
| NM_002095.1 | general transcription factor IIE, polypeptide 2, beta 34 kDa (GTF2E2) |
| NM_005720.1 | actin related protein 2/3 complex, subunit 1B, 41 kDa (ARPC1B) |
| NM_003868.1 | fibroblast growth factor 16 (FGF16) |
| NM_004214.3 | fibroblast growth factor (acidic) intracellular binding protein (FIBP), transcript variant 2 |

TABLE 1-continued

| Database ID | Description |
|---|---|
| NM_021079.2 | N-myristoyltransferase 1 (NMT1) |
| NM_015833.1 | adenosine deaminase, RNA-specific, B1 (RED1 homolog rat) (ADARB1), transcript variant 2 |
| PHR5001 | Recombinant human CTLA-4/Fc |
| BC030983.1 | immunoglobulin lambda locus (IGL@) |
| BC030984.1 | cDNA clone MGC: 32654 IMAGE: 4701898, complete cds |
| NM_133494.1 | NIMA (never in mitosis gene a)-related kinase 7 (NEK7) |
| BC010467.1 | cDNA clone MGC: 17410 IMAGE: 4156035, complete cds |
| NM_014060.1 | malignant T cell amplified sequence 1 (MCTS1) |
| NM_016167.3 | nucleolar protein 7, 27 kDa (NOL7) |
| BC015833.1 | cDNA clone MGC: 27152 IMAGE: 4691630, complete cds |
| NM_145063.1 | chromosome 6 open reading frame 130 (C6orf130) |
| BC040106.1 | hypothetical protein HSPC111 (HSPC111) |
| BC010947.1 | signal recognition particle 19 kDa (SRP19) |
| NM_014065.2 | Protein asteroid homolog 1 |
| BC012760.2 | Glycogen synthase kinase-3 beta |
| NM_004088.1 | deoxynucleotidyltransferase, terminal (DNTT), transcript variant 1 |
| BC019337.1 | immunoglobulin heavy constant gamma 1 (G1m marker) (IGHG1) |
| NM_002938.2 | ring finger protein 4 (RNF4) |
| NM_006620.2 | HBS1-like (*S. cerevisiae*) (HBS1L) |
| NM_000992.2 | 60S ribosomal protein L29 |
| NM_024668.2 | ankyrin repeat and KH domain containing 1 (ANKHD1), transcript variant 3 |
| NM_031445.1 | AMME chromosomal region gene 1-like (AMMECR1L) |
| NM_003517.2 | histone cluster 2, H2ac (HIST2H2AC) |
| BC072419.1 | Ig gamma-1 chain C region |
| NM_145174.1 | DnaJ (Hsp40) homolog, subfamily B, member 7 (DNAJB7) |
| BC022361.1 | rRNA-processing protein FCF1 homolog |
| BC006376.1 | N-myristoyltransferase 2 (NMT2) |
| NM_001895.1 | casein kinase 2, alpha 1 polypeptide (CSNK2A1), transcript variant 2 |
| NM_003524.2 | Histone H2B type 1-H |
| BC027951.1 | Cas scaffolding protein family member 4 |
| NM_134427.1 | regulator of G-protein signaling 3 (RGS3), transcript variant 4 |
| NM_052969.1 | ribosomal protein L39-like (RPL39L) |
| NM_023080.1 | chromosome 8 open reading frame 33 (C8orf33) |
| NM_138779.1 | chromosome 13 open reading frame 27 (C13orf27) |
| BC026030.1 | zinc finger protein 239 (ZNF239) |
| BC029760.1 | OTU domain containing 6B (OTUD6B) |
| PHC1475 | C-C motif chemokine 21 |
| NM_133336.1 | Wolf-Hirschhorn syndrome candidate 1 (WHSC1), transcript variant 9 |
| BC034142.1 | immunoglobulin kappa variable 1-5 (IGKV1-5) |
| NM_020235.2 | bobby sox homolog (*Drosophila*) (BBX) |
| NM_198829.1 | Ras-related C3 botulinum toxin substrate 1 |
| BC098112.1 | Histone H2B type 1-N |
| NM_032359.1 | chromosome 3 open reading frame 26 (C3orf26) |
| NM_001966.2 | Peroxisomal bifunctional enzyme |
| BC032451.1 | cDNA clone MGC: 40426 IMAGE: 5178085, complete cds |
| XM_379117.1 | PREDICTED: *Homo sapiens* hypothetical protein LOC150568 (LOC150568) |
| BC033159.1 | DnaJ (Hsp40) homolog, subfamily C, member 8 (DNAJC8) |
| NM_006756.2 | transcription elongation factor A (SII), 1 (TCEA1), transcript variant 1 |
| NM_016940.1 | RWD domain containing 2B (RWDD2B) |
| NM_177559.2 | casein kinase 2, alpha 1 polypeptide (CSNK2A1), transcript variant 1 |
| NM_004178.3 | TAR (HIV-1) RNA binding protein 2 (TARBP2), transcript variant 3 |
| NM_032338.2 | chromosome 12 open reading frame 31 (C12orf31) |
| BC005955.1 | chromosome 8 open reading frame 53 (C8orf53) |
| NM_001009613.1 | Sperm protein associated with the nucleus on the X chromosome N4 |
| BC036723.1 | Fc fragment of IgG, low affinity IIIa, receptor (CD16a) (FCGR3A) |
| NM_003690.3 | Interferon-inducible double stranded RNA-dependent protein kinase activator A |
| NM_014473.2 | DIM1 dimethyladenosine transferase 1-like (*S. cerevisiae*) (DIMT1L) |
| NM_032855.1 | hematopoietic SH2 domain containing (HSH2D) |
| NM_001167.2 | baculoviral IAP repeat-containing 4 (BIRC4) |
| NM_178571.2 | hypothetical protein MGC51025 (MGC51025) |
| NM_003600.1 | aurora kinase A (AURKA), transcript variant 2 |
| NM_006912.3 | Ras-like without CAAX 1 (RIT1) |
| NM_005307.1 | G protein-coupled receptor kinase 4 |
| BC001280.1 | Serine/threonine-protein kinase 6 |

TABLE 1-continued

| Database ID | Description |
|---|---|
| NM_182970.2 | regulating synaptic membrane exocytosis 4 (RIMS4) |
| NM_153332.2 | three prime histone mRNA exonuclease 1 (THEX1) |
| NM_139016.2 | chromosome 20 open reading frame 198 (C20orf198) |
| NM_003677.3 | Density-regulated protein |
| NM_013293.1 | Transformer-2 protein homolog |
| BC033856.1 | La ribonucleoprotein domain family, member 1 (LARP1) |
| NM_000939.1 | proopiomelanocortin (adrenocorticotropin/beta-lipotropin/alpha-melanocyte stimulating hormone/beta-melanocyte stimulating hormone/beta-endorphin) (POMC), transcript variant 2 |
| BC009348.2 | cirrhosis, autosomal recessive 1A (cirhin) (CIRH1A) |
| NM_014508.2 | apolipoprotein B mRNA editing enzyme, catalytic polypeptide-like 3C (APOBEC3C), mRNA. |
| NM_080659.1 | chromosome 11 open reading frame 52 (C11orf52) |
| NM_022755.2 | inositol 1,3,4,5,6-pentakisphosphate 2-kinase (IPPK) |
| NM_002690.1 | polymerase (DNA directed), beta (POLB) |
| BC011668.1 | Casein kinase II subunit alpha |
| NM_002128.2 | high-mobility group box 1 (HMGB1) |
| BC012472.1 | ubiquitin D (UBD) |
| BC030020.2 | DEAD (Asp-Glu-Ala-Asp) box polypeptide 55 (DDX55) |
| BC018060.1 | Ras-like without CAAX 2 (RIT2) |
| NM_003141.2 | tripartite motif-containing 21 (TRIM21) |
| NM_007054.1 | kinesin family member 3A (KIF3A) |
| NM_006924.3 | splicing factor, arginine/serine-rich 1 (splicing factor 2, alternate splicing factor) (SFRS1), transcript variant 1 |
| NM_032563.1 | late cornified envelope 3D (LCE3D) |
| NM_173080.1 | small proline-rich protein 4 (SPRR4) |
| NM_003527.4 | Histone H2B type 1-O |
| BC009762.2 | Tripartite motif-containing protein 41 |
| NM_006861.2 | RAB35, member RAS oncogene family (RAB35) |
| NM_002136.1 | heterogeneous nuclear ribonucleoprotein A1 (HNRNPA1), transcript variant 1 |
| BC009623.1 | nucleophosmin (nucleolar phosphoprotein B23, numatrin) (NPM1) |
| NM_021063.2 | Histone H2B type 1-D |
| BC054021.1 | pterin-4 alpha-carbinolamine dehydratase/dimerization cofactor of hepatocyte nuclear factor 1 alpha (TCF1) 2 (PCBD2) |
| NM_012108.1 | signal transducing adaptor family member 1 (STAP1) |
| NM_023937.1 | mitochondrial ribosomal protein L34 (MRPL34), nuclear gene encoding mitochondrial protein |
| XM_088679.2 | Spermatid nuclear transition protein 4 |
| NM_022720.5 | DiGeorge syndrome critical region gene 8 (DGCR8) |
| NM_016073.2 | hepatoma-derived growth factor, related protein 3 (HDGFRP3) |
| NM_018105.1 | THAP domain containing, apoptosis associated protein 1 (THAP1), transcript variant 1 |
| NM_005371.2 | methyltransferase like 1 (METTL1), transcript variant 1 |
| BC029427.1 | coiled-coil domain containing 23 (CCDC23) |
| NM_032476.1 | mitochondrial ribosomal protein S6 (MRPS6), nuclear gene encoding mitochondrial protein |
| NM_003089.4 | small nuclear ribonucleoprotein 70 kDa polypeptide (RNP antigen) (SNRP70) |
| BC020972.1 | Casein kinase I isoform gamma-2 |
| BC000381.2 | TBP-like 1 (TBPL1) |
| NM_007285.5 | GABA(A) receptor-associated protein-like 2 (GABARAPL2) |
| NM_004060.2 | cyclin G1 (CCNG1), transcript variant 1 |
| BC001780.1 | Uncharacterized methyltransferase WBSCR22 |
| NM_022048.1 | casein kinase 1, gamma 1 (CSNK1G1) |
| BC035256.1 | Putative adenylate kinase 7 |
| NM_175887.2 | proline rich 15 (PRR15) |
| BC010919.1 | ribosomal protein L35 (RPL35) |
| NM_016207.2 | cleavage and polyadenylation specific factor 3, 73 kDa (CPSF3) |
| BC000784.1 | baculoviral IAP repeat-containing 5 (survivin) (BIRC5) |
| NM_002364.1 | melanoma antigen family B, 2 (MAGEB2) |
| NM_022839.2 | mitochondrial ribosomal protein S11 (MRPS11), nuclear gene encoding mitochondrial protein, transcript variant 1 |
| NM_014370.2 | SFRS protein kinase 3 (SRPK3) |
| NM_016505.2 | zinc finger, CCHC domain containing 17 (ZCCHC17) |
| BC030813.1 | cDNA clone MGC: 22645 IMAGE: 4700961, complete cds |
| BC020803.1 | developmentally regulated GTP binding protein 1 (DRG1) |
| NM_205848.1 | synaptotagmin VI (SYT6) |
| NM_006398.2 | Ubiquitin D |
| NM_017646.3 | tRNA isopentenyltransferase 1 (TRIT1) |
| NM_006925.2 | Splicing factor, arginine/serine-rich 5 |
| NM_153822.1 | proteasome (prosome, macropain) 26S subunit, non-ATPase, 4 (PSMD4), transcript variant 2 |
| NM_014321.2 | origin recognition complex, subunit 6 like (yeast) (ORC6L) |
| BC012876.1 | Ig lambda chain C regions |

TABLE 1-continued

| Database ID | Description |
| --- | --- |
| NM_021967.1 | small EDRK-rich factor 1A (telomeric) (SERF1A) |
| NM_003295.1 | tumor protein, translationally-controlled 1 (TPT1) |
| NM_017503.2 | surfeit 2 (SURF2) |
| BC018137.1 | TATA box binding protein (TBP)-associated factor, RNA polymerase I, B, 63 kDa (TAF1B) |
| BC005004.1 | family with sequence similarity 64, member A (FAM64A) |
| NM_152373.2 | zinc finger protein 684 (ZNF684) |
| NM_000989.2 | ribosomal protein L30 (RPL30) |
| NM_000800.2 | fibroblast growth factor 1 (acidic) (FGF1), transcript variant 1 |
| NM_000975.2 | ribosomal protein L11 (RPL11) |
| PHC1695 | C—X—C motif chemokine 11 |
| NM_022140.2 | Band 4.1-like protein 4A |
| NM_016287.2 | heterochromatin protein 1, binding protein 3 (HP1BP3) |
| BC015586.2 | laminin, gamma 1 (formerly LAMB2) (LAMC1) |
| NM_023931.1 | zinc finger protein 747 (ZNF747) |
| NM_153207.2 | AE binding protein 2 (AEBP2) |
| NM_007079.2 | Protein tyrosine phosphatase type IVA 3 |
| NM_004397.3 | Probable ATP-dependent RNA helicase DDX6 |
| NM_012424.2 | Ribosomal protein S6 kinase delta-1 |
| NM_020239.2 | CDC42 small effector 1 (CDC42SE1), transcript variant 2 |
| BC029378.1 | telomeric repeat binding factor (NIMA-interacting) 1 (TERF1) |
| BC000306.1 | hydroxyacyl-Coenzyme A dehydrogenase (HADH) |
| NM_182692.1 | Serine/threonine-protein kinase SRPK2 |
| NM_032350.3 | Uncharacterized protein C7orf50 |
| NM_001022.3 | ribosomal protein S19 (RPS19) |
| NM_001002913.1 | peptidyl-tRNA hydrolase 1 homolog (S. cerevisiae) (PTRH1) |
| BC000535.1 | Suppressor of SWI4 1 homolog |
| NM_017692.1 | aprataxin (APTX), transcript variant 4 |
| NM_000993.2 | ribosomal protein L31 (RPL31), transcript variant 1 |
| NM_152653.1 | ubiquitin-conjugating enzyme E2E 2 (UBC4/5 homolog, yeast) (UBE2E2) |
| NM_014891.1 | PDGFA associated protein 1 (PDAP1) |
| NM_012148.1 | double homeobox, 3 (DUX3) |
| NM_024046.1 | CaM kinase-like vesicle-associated (CAMKV) |
| NM_022063.1 | chromosome 10 open reading frame 84 (C10orf84) |
| BC036434.1 | Serine/threonine-protein kinase VRK2 |
| NM_001396.2 | Dual specificity tyrosine-phosphorylation-regulated kinase 1A |
| NM_004939.1 | DEAD (Asp-Glu-Ala-Asp) box polypeptide 1 (DDX1) |
| NM_001039724.1 | Nostrin |
| NM_138551.1 | thymic stromal lymphopoietin (TSLP), transcript variant 2 |
| XM_379194.1 | PREDICTED: Homo sapiens hypothetical LOC401068 (LOC401068) |
| BC007401.2 | cell division cycle 25 homolog A (S. pombe) (CDC25A) |
| BC008902.2 | GRIP and coiled-coil domain-containing protein 1 |
| BC019039.2 | Regulator of G-protein signaling 3 |
| NM_016050.1 | mitochondrial ribosomal protein L11 (MRPL11), nuclear gene encoding mitochondrial protein, transcript variant 1 |
| NM_002927.3 | regulator of G-protein signaling 13 (RGS13), transcript variant 1 |
| NM_207430.1 | FLJ46266 protein (FLJ46266), mRNA. |
| NM_016508.2 | Cyclin-dependent kinase-like 3 |
| NM_197964.1 | chromosome 7 open reading frame 55 (C7orf55) |
| BC021930.1 | KIAA1530 protein (KIAA1530) |
| NM_145043.1 | nei like 2 (E. coli) (NEIL2) |
| BC030586.2 | signal transducing adaptor molecule (SH3 domain and ITAM motif) 1 (STAM) |
| BC004292.1 | PHD finger protein 15 (PHF15) |
| BC022378.1 | zinc finger with KRAB and SCAN domains 1 (ZKSCAN1) |
| NM_003792.1 | endothelial differentiation-related factor 1 (EDF1), transcript variant alpha |
| BC070154.1 | Non-histone chromosomal protein HMG-14 |
| BC010074.2 | FUS interacting protein (serine/arginine-rich) 1 (FUSIP1) |
| NM_002201.3 | interferon stimulated exonuclease gene 20 kDa (ISG20) |
| BC033621.2 | Pseudouridylate synthase 7 homolog-like protein |
| NM_004114.2 | fibroblast growth factor 13 (FGF13), transcript variant 1A |
| NM_012420.1 | interferon-induced protein with tetratricopeptide repeats 5 (IFIT5) |
| NM_016203.2 | protein kinase, AMP-activated, gamma 2 non-catalytic subunit (PRKAG2), transcript variant a, mRNA. |
| NM_014878.2 | Pumilio domain-containing protein KIAA0020 |
| NM_018664.1 | Jun dimerization protein p21SNFT (SNFT) |
| NM_002402.1 | mesoderm specific transcript homolog (mouse) (MEST), transcript variant 1 |
| NM_003769.2 | splicing factor, arginine/serine-rich 9 (SFRS9) |
| NM_018132.3 | centromere protein Q (CENPQ) |
| NM_006072.4 | chemokine (C-C motif) ligand 26 (CCL26) |
| NM_021029.3 | ribosomal protein L36a (RPL36A) |
| NM_000978.2 | ribosomal protein L23 (RPL23) |
| NM_001023.2 | ribosomal protein S20 (RPS20) |

TABLE 1-continued

| Database ID | Description |
|---|---|
| BC013366.2 | UNC-112 related protein 2 (URP2) |
| BC001327.1 | interferon-related developmental regulator 2 (IFRD2) |
| BC000522.1 | serpin peptidase inhibitor, clade F (alpha-2 antiplasmin, pigment epithelium derived factor), member 1 (SERPINF1) |
| NM_019067.1 | guanine nucleotide binding protein-like 3 (nucleolar)-like (GNL3L) |
| NM_152634.1 | TFS2-M domain-containing protein 1 (MGC17403) |
| BC011842.2 | hypothetical protein FLJ11184 (FLJ11184) |
| BC068514.1 | NF-kappaB repressing factor (NKRF) |
| NM_018063.3 | helicase, lymphoid-specific (HELLS) |
| NM_198467.1 | round spermatid basic protein 1-like (RSBN1L) |
| NM_198517.2 | TBC1 domain family, member 10C (TBC1D10C) |
| NM_001564.1 | inhibitor of growth family, member 2 (ING2) |
| NM_002930.1 | GTP-binding protein Rit2 |
| NM_019058.1 | DNA-damage-inducible transcript 4 protein |
| NM_020661.1 | activation-induced cytidine deaminase (AICDA) |
| NM_173822.1 | family with sequence similarity 126, member B (FAM126B) |
| BC056887.1 | chromosome 5 open reading frame 5 (C5orf5) |
| BC070334.1 | immunoglobulin kappa constant (IGKC) |
| NM_004071.1 | Dual specificity protein kinase CLK1 |
| NM_005801.2 | eukaryotic translation initiation factor 1 (EIF1) |
| BC001487.2 | TAR DNA-binding protein 43 |
| NM_006790.1 | myotilin (MYOT) |
| NM_175923.2 | hypothetical protein MGC42630 (MGC42630) |
| NM_000122.1 | excision repair cross-complementing rodent repair deficiency, complementation group 3 (xeroderma pigmentosum group B complementing) (ERCC3) |
| BC010501.1 | Catenin delta-1 |
| BC005298.1 | cyclin-dependent kinase 7 (MO15 homolog, *Xenopus laevis*, cdk-activating kinase) (CDK7) |
| PHC0076 | interleukin 7 (IL7) |
| NM_138349.2 | Tumor protein p53-inducible protein 13 |
| BC000044.1 | Spindlin-2B |
| NM_014747.2 | regulating synaptic membrane exocytosis 3 (RIMS3) |
| NM_001014.2 | ribosomal protein S10 (RPS10) |
| NM_005678.3 | SNRPN upstream reading frame (SNURF), transcript variant 1 |
| BC010876.1 | nei endonuclease VIII-like 1 (*E. coli*) (NEIL1) |
| BC025281.1 | RNA binding motif protein 9 (RBM9) |
| NM_001013.2 | ribosomal protein S9 (RPS9) |
| NM_015414.2 | ribosomal protein L36 (RPL36), transcript variant 2 |
| NM_017566.2 | kelch domain containing 4 (KLHDC4) |
| BC015818.1 | lectin, galactoside-binding, soluble, 8 (galectin 8) (LGALS8) |
| BC036109.1 | SECIS binding protein 2 (SECISBP2) |
| NM_005738.1 | ADP-ribosylation factor-like 4A (ARL4A), transcript variant 1 |
| BC022816.1 | NA |
| NM_024303.1 | zinc finger and SCAN domain containing 5 (ZSCAN5) |
| BC018823.2 | splicing factor, arginine/serine-rich 5 (SFRS5) |
| NM_024319.1 | chromosome 1 open reading frame 35 (C1orf35) |
| PV3359 | Ephrin receptor A3 (EPHA3), transcript variant 1 |
| NM_145899.1 | high mobility group AT-hook 1 (HMGA1), transcript variant 1 |
| NM_021158.1 | tribbles homolog 3 (*Drosophila*) (TRIB3) |
| NM_005794.2 | dehydrogenase/reductase (SDR family) member 2 (DHRS2), transcript variant 2 |
| BC005807.2 | stearoyl-CoA desaturase (delta-9-desaturase) (SCD) |
| NM_006374.2 | serine/threonine kinase 25 (STE20 homolog, yeast) (STK25) |
| NM_152757.1 | Putative uncharacterized protein C20orf200 |
| NM_001009880.1 | chromosome 22 open reading frame 9 (C22orf9), transcript variant 2 |
| NM_138558.1 | protein phosphatase 1, regulatory (inhibitor) subunit 8 (PPP1R8), transcript variant 2 |
| BC007852.1 | Serine/threonine-protein kinase 25 |
| NM_012396.1 | pleckstrin homology-like domain, family A, member 3 (PHLDA3) |
| NM_012437.2 | SNAP-associated protein (SNAPAP) |
| PHC0205 | interleukin 20 (IL20) |
| NM_016093.2 | ribosomal protein L26-like 1 (RPL26L1) |
| NM_005902.1 | SMAD family member 3 (SMAD3) |
| XM_375456.2 | Ataxin-7-like protein 3 |
| NM_006275.2 | splicing factor, arginine/serine-rich 6 (SFRS6) |
| BC011600.1 | cDNA clone IMAGE: 3050953, **** WARNING: chimeric clone **** |
| NM_014570.2 | ADP-ribosylation factor GTPase activating protein 3 (ARFGAP3) |
| NM_022551.2 | ribosomal protein S18 (RPS18) |
| BC063275.1 | eukaryotic translation initiation factor 2C, 1 (EIF2C1) |
| BC062423.1 | chromosome 7 open reading frame 41 (C7orf41) |
| BC096708.1 | Wilms tumor-associated protein |
| NM_199123.1 | SET domain containing 3 (SETD3), transcript variant 2 |
| BC010907.1 | PAK1 interacting protein 1 (PAK1IP1) |
| NM_004217.1 | aurora kinase B (AURKB) |

TABLE 1-continued

| Database ID | Description |
|---|---|
| NM_005737.3 | ADP-ribosylation factor-like 4C (ARL4C) |
| NM_020467.2 | small trans-membrane and glycosylated protein (LOC57228), transcript variant 2 |
| BC021180.2 | high-mobility group box 4 (HMGB4) |
| NM_004728.2 | DEAD (Asp-Glu-Ala-Asp) box polypeptide 21 (DDX21) |
| BC030702.1 | microcephaly, primary autosomal recessive 1 (MCPH1) |
| NM_003724.1 | jerky homolog (mouse) (JRK), transcript variant 1 |
| NM_016077.1 | peptidyl-tRNA hydrolase 2 (PTRH2), nuclear gene encoding mitochondrial protein |
| NM_014955.2 | KIAA0859 (KIAA0859), transcript variant 2 |
| NM_003503.2 | Cell division cycle 7-related protein kinase |
| BC017212.2 | PHD finger protein 11 (PHF11) |
| NM_019069.3 | WD repeat domain 5B (WDR5B) |
| BC094719.1 | Rho GTPase-activating protein 12 |
| BC021187.1 | DKFZP434K028 protein (DKFZP434K028) |
| NM_003948.2 | Cyclin-dependent kinase-like 2 |
| BC040183.2 | Rap guanine nucleotide exchange factor (GEF) 4 (RAPGEF4) |
| NM_014061.3 | melanoma antigen family H, 1 (MAGEH1) |
| BC032587.1 | tubby like protein 3 (TULP3) |
| BC005332.1 | cDNA clone MGC: 12418 IMAGE: 3934658, complete cds |
| BC033710.2 | RAD54 homolog B (*S. cerevisiae*) (RAD54B) |
| BC010425.1 | acyl-Coenzyme A oxidase 1, palmitoyl (ACOX1) |
| NM_021138.2 | TNF receptor-associated factor 2 (TRAF2) |
| BC093990.1 | Sin3 histone deacetylase corepressor complex component SDS3 |
| NM_014288.2 | Centromere protein R |
| NM_024826.1 | Microtubule-associated protein 9 |
| BC035968.1 | chloride intracellular channel 5 (CLIC5) |
| BC096165.1 | Troponin I, cardiac muscle |
| BC012105.1 | nuclear VCP-like (NVL) |
| BC011924.1 | unkempt homolog (*Drosophila*)-like (UNKL) |
| NM_001311.2 | Cysteine-rich protein 1 |
| NM_014445.2 | stress-associated endoplasmic reticulum protein 1 (SERP1) |
| NM_005979.1 | S100 calcium binding protein A13 (S100A13), transcript variant 2 |
| BC036923.1 | chromosome 9 open reading frame 150 (C9orf150) |
| NM_033671.1 | cyclin B3 (CCNB3), transcript variant 2 |
| BC014441.1 | NOL1/NOP2/Sun domain family, member 4 (NSUN4) |
| BC031549.1 | CDC-like kinase 1 (CLK1) |
| NM_194290.1 | cDNA FLJ42001 fis, clone SPLEN2029912 (LOC153684 protein) [Source: UniProtKB/TrEMBL; Acc: Q6ZVW3] |
| BC053984.1 | immunoglobulin heavy variable 4-31 (IGHV4-31) |
| BC050563.1 | hypothetical protein LOC202051 (LOC202051) |
| BC050718.1 | polymerase (DNA directed) kappa (POLK) |
| BC000896.1 | RAB10, member RAS oncogene family (RAB10) |
| NM_006252.2 | AMP-activated protein_kinase A2/B1/G1: PRKAA2/B1/G1 sequences are seperated by - (in protein list file). |
| BC013630.1 | JTV1 gene (JTV1) |
| BC009108.1 | cDNA clone IMAGE: 3451214 (MCM10) |
| BC002645.1 | syntaxin 5 (STX5) |
| NM_138414.1 | coiled-coil domain containing 101 (CCDC101) |
| NM_002740.1 | protein kinase C, iota (PRKCI) |
| NM_002822.3 | twinfilin, actin-binding protein, homolog 1 (*Drosophila*) (TWF1) |
| BC003566.1 | zinc finger protein 24 (ZNF24) |
| NM_022756.2 | Uncharacterized protein C1orf149 |
| NM_153035.1 | chromosome 1 open reading frame 83 (C1orf83) |
| NM_177524.1 | mesoderm specific transcript homolog (mouse) (MEST), transcript variant 2 |
| NM_004635.2 | mitogen-activated protein kinase-activated protein kinase 3 (MAPKAPK3) |
| NM_005607.1 | Focal adhesion kinase 1 |
| BC010697.1 | RNA-binding protein 40 |
| NM_174942.1 | GAS2-like protein 3 |
| BC038976.1 | Rho GTPase-activating protein 15 |
| NM_012117.1 | chromobox homolog 5 (HP1 alpha homolog, *Drosophila*) (CBX5) |
| NM_013313.3 | yippee-like 1 (*Drosophila*) (YPEL1) |
| NM_148179.1 | chromosome 9 open reading frame 23 (C9orf23), transcript variant 2 |
| BC038105.2 | membrane protein, palmitoylated 7 (MAGUK p55 subfamily member 7) (MPP7) |
| BC091489.1 | zinc finger, MYND domain containing 11, mRNA (cDNA clone MGC: 111056 IMAGE: 6186814), complete cds |
| BC034435.1 | zinc finger CCCH-type containing 3 (ZC3H3) |
| NM_152736.2 | Zinc finger protein 187 |
| NM_015014.1 | RNA binding motif protein 34 (RBM34) |
| NM_003137.2 | SFRS protein kinase 1 (SRPK1) |
| BC016486.1 | lectin, galactoside-binding, soluble, 8 (galectin 8) (LGALS8) |
| BC000238.1 | ankyrin repeat and zinc finger domain containing 1 (ANKZF1) |
| NM_002904.4 | RD RNA binding protein (RDBP) |
| BC009046.1 | neurogenic differentiation 1 (NEUROD1) |
| NM_198965.1 | Parathyroid hormone-related protein |

TABLE 1-continued

| Database ID | Description |
|---|---|
| BC047776.2 | coiled-coil domain containing 43 (CCDC43) |
| NM_001004306.1 | similar to hypothetical protein FLJ36492 (MGC87631) |
| NM_006800.2 | male-specific lethal 3-like 1 (*Drosophila*) (MSL3L1), transcript variant 3 |
| NM_006038.1 | spermatogenesis associated 2 (SPATA2) |
| NM_014477.2 | chromosome 20 open reading frame 10 (C20orf10) |
| BC027612.2 | EP300-interacting inhibitor of differentiation 3 |
| NM_017411.2 | survival of motor neuron 2, centromeric (SMN2), transcript variant d |
| BC004876.1 | Protein MCM10 homolog |
| NM_201516.1 | H2A histone family, member V (H2AFV), transcript variant 4 |
| NM_022156.3 | dihydrouridine synthase 1-like (*S. cerevisiae*) (DUS1L) |
| BC015742.1 | polymerase (DNA directed), eta (POLH) |
| NM_001015509.1 | Peptidyl-tRNA hydrolase 2, mitochondrial |
| NM_014366.1 | guanine nucleotide binding protein-like 3 (nucleolar) (GNL3), transcript variant 1 |
| NM_018357.2 | La ribonucleoprotein domain family, member 6 (LARP6), transcript variant 1 |
| BC020221.1 | SH3 and cysteine rich domain (STAC) |
| NM_005307.1 | G protein-coupled receptor kinase 4 |
| NM_017785.2 | coiled-coil domain containing 99 (CCDC99) |
| BC026101.2 | nudE nuclear distribution gene E homolog (*A. nidulans*)-like 1 (NDEL1) |
| NM_175571.2 | GTPase, IMAP family member 8 (GIMAP8) |
| NM_004286.2 | GTP binding protein 1 (GTPBP1) |
| BC072461.1 | Cysteine and histidine-rich domain-containing protein 1 |
| BC047945.1 | tripartite motif-containing 69 (TRIM69) |
| BC005858.1 | fibronectin 1 (FN1) |
| NM_001722.2 | polymerase (RNA) III (DNA directed) polypeptide D, 44 kDa (POLR3D) |
| NM_024333.1 | Fibronectin type III and SPRY domain-containing protein 1 |
| NM_144595.1 | SLAIN motif family, member 1 (SLAIN1), transcript variant 2 |
| NM_002469.1 | myogenic factor 6 (herculin) (MYF6) |
| BC053866.1 | endothelin 3 (EDN3) |
| NM_001319.5 | casein kinase 1, gamma 2 (CSNK1G2) |
| BC006124.1 | IMP (inosine monophosphate) dehydrogenase 2 (IMPDH2) |
| NM_014667.1 | vestigial like 4 (*Drosophila*) (VGLL4) |
| NM_031465.2 | chromosome 12 open reading frame 32 (C12orf32) |
| NM_182612.1 | Parkinson disease 7 domain containing 1 (PDDC1) |
| PV4803 | epidermal growth factor receptor (erythroblastic leukemia viral (v-erb-b) oncogene homolog, avian) (EGFR); see catalog number for detailed information on wild-type or point mutant status |
| NM_152266.1 | chromosome 19 open reading frame 40 (C19orf40) |
| NM_000997.2 | ribosomal protein L37 (RPL37) |
| BC001728.1 | TCF3 fusion partner |
| BC007015.1 | cyclin E2 (CCNE2) |
| NM_022347.1 | interferon responsive gene 15 (IFRG15) |
| BC031821.1 | Secernin-3 |
| NM_016304.2 | chromosome 15 open reading frame 15 (C15orf15) |
| BC069677.1 | Regulator of G-protein signaling 8 |
| BC013331.1 | H2A histone family, member Y (H2AFY) |
| NM_017838.2 | nucleolar protein family A, member 2 (H/ACA small nucleolar RNPs) (NOLA2), transcript variant 1 |
| BC013796.1 | adaptor-related protein complex 2, mu 1 subunit (AP2M1) |
| NM_080743.2 | serine-arginine repressor protein (35 kDa) (SRrp35) |
| BC000190.1 | zinc finger, C3HC-type containing 1 (ZC3HC1) |
| BC036089.1 | myeloid/lymphoid or mixed-lineage leukemia (trithorax homolog, *Drosophila*); translocated to, 3 (MLLT3) |
| NM_018215.2 | hypothetical protein FLJ10781 (FLJ10781), transcript variant 1 |
| BC095401.1 | AKT-interacting protein |
| NM_001008572.1 | tubulin tyrosine ligase-like family, member 1 (TTLL1), transcript variant 2 |
| BC103812.1 | Alpha-ketoglutarate-dependent dioxygenase alkB homolog 3 |
| BC036365.1 | PH domain-containing protein C10orf81 |
| NM_016047.1 | splicing factor 3B, 14 kDa subunit (SF3B14) |
| BC014949.1 | DEXH (Asp-Glu-X-His) box polypeptide 58 (DHX58) |
| BC047690.1 | Ras-related protein M-Ras |
| NM_001894.2 | casein kinase 1, epsilon (CSNK1E), transcript variant 2 |
| NM_006482.1 | Dual specificity tyrosine-phosphorylation-regulated kinase 2 |
| NM_025104.2 | Protein DBF4 homolog B |
| NM_017819.1 | RNA (guanine-9-)-methyltransferase domain-containing protein 1, mitochondrial |
| NM_199139.1 | XIAP associated factor-1 (XAF1), transcript variant 2 |
| NM_003910.2 | BUD31 homolog (*S. cerevisiae*) (BUD31) |
| BC000442.1 | Serine/threonine-protein kinase 12 |
| BC028711.2 | cancer/testis antigen CT45-3 (CT45-3) |
| NM_018158.1 | solute carrier family 4 (anion exchanger), member 1, adaptor protein (SLC4A1AP) |
| BC034692.1 | anillin, actin binding protein (ANLN) |

TABLE 1-continued

| Database ID | Description |
|---|---|
| NM_173605.1 | potassium channel regulator (KCNRG), transcript variant 1 |
| NM_014047.1 | chromosome 19 open reading frame 53 (C19orf53) |
| BC073791.1 | immunoglobulin kappa constant, mRNA (cDNA clone MGC: 88809 IMAGE: 6279986), complete cds |
| BC014928.1 | MYC-induced nuclear antigen |
| BC053656.1 | EGF-like repeats and discoidin I-like domains 3 (EDIL3) |
| XM_378879.2 | PREDICTED: *Homo sapiens* hypothetical LOC400763 (LOC400763) |
| NM_017817.1 | RAB20, member RAS oncogene family (RAB20) |
| BC031608.1 | REST corepressor 3 (RCOR3) |
| BC047722.1 | hypothetical protein MGC52110 (MGC52110) |
| BC020726.1 | sciellin (SCEL) |
| NM_024039.1 | MIS12, MIND kinetochore complex component, homolog (yeast) (MIS12) |
| BC026213.1 | F-box/WD repeat-containing protein 11 |
| NM_002135.3 | nuclear receptor subfamily 4, group A, member 1 (NR4A1), transcript variant 1 |
| NM_015939.2 | tRNA methyltransferase 6 homolog (*S. cerevisiae*) (TRMT6) |
| NM_018039.2 | jumonji domain containing 2D (JMJD2D) |
| NM_007373.2 | soc-2 suppressor of clear homolog (*C. elegans*) (SHOC2) |
| BC067120.1 | protein tyrosine phosphatase domain containing 1, mRNA (cDNA clone MGC: 70358 IMAGE: 5539182), complete cds |
| NM_015918.2 | processing of precursor 5, ribonuclease P/MRP subunit (*S. cerevisiae*) (POP5), transcript variant 1 |
| NM_152677.1 | zinc finger and SCAN domain containing 4 (ZSCAN4) |
| BC008902.2 | GRIP and coiled-coil domain-containing protein 1 |
| NM_001008239.1 | chromosome 18 open reading frame 25 (C18orf25), transcript variant 2 |
| NM_183397.1 | peroxisomal membrane protein 4, 24 kDa (PXMP4), transcript variant 2 |
| NM_006337.3 | microspherule protein 1 (MCRS1), transcript variant 1 |
| BC034401.1 | cDNA clone IMAGE: 5172086, partial cds |
| NM_006755.1 | transaldolase 1 (TALDO1) |
| NM_004853.1 | syntaxin 8 (STX8) |
| BC036910.1 | hypothetical LOC388882 (LOC388882) |
| BC094687.1 | Elongation factor 1-alpha 1 |
| NM_144608.1 | hexamthylene bis-acetamide inducible 2 (HEXIM2) |
| NM_003831.1 | RIO kinase 3 (yeast) (RIOK3) |
| BC009250.1 | guanine nucleotide binding protein-like 2 (nucleolar) (GNL2) |
| BC032598.1 | NHL repeat containing 2 (NHLRC2) |
| NM_018697.3 | LanC lantibiotic synthetase component C-like 2 (bacterial) (LANCL2) |
| NM_024104.1 | chromosome 19 open reading frame 42 (C19orf42) |
| BC030665.1 | Sulfotransferase 4A1 |
| BC004955.1 | ATPase inhibitory factor 1 (ATPIF1) |
| BC009010.1 | Uncharacterized protein C6orf142 homolog |
| BC012887.1 | Nucleolar and spindle-associated protein 1 |
| BC015066.1 | core-binding factor, runt domain, alpha subunit 2; translocated to, 2 (CBFA2T2) |
| BC052303.1 | Rho GTPase activating protein 4 (ARHGAP4) |
| NM_080414.1 | vacuolar protein sorting 16 homolog (*S. cerevisiae*) (VPS16), transcript variant 2 |
| NM_001790.2 | cell division cycle 25 homolog C (*S. pombe*) (CDC25C), transcript variant 1 |
| PHC0045 | interleukin 4 (IL4), transcript variant 1 |
| NM_145041.1 | transmembrane protein 106A (TMEM106A) |
| NM_021639.2 | GC-rich promoter binding protein 1-like 1 (GPBP1L1) |
| BC028295.1 | peptidase D (PEPD) |
| PV3612 | aurora kinase A (AURKA), transcript variant 2 |
| NM_032321.1 | hypothetical protein MGC13057 (MGC13057), transcript variant 4 |
| BC010033.1 | quinolinate phosphoribosyltransferase (nicotinate-nucleotide pyrophosphorylase (carboxylating)) (QPRT) |
| NM_001064.1 | Transketolase |
| NM_017572.2 | MAP kinase-interacting serine/threonine-protein kinase 2 |
| NM_022650.1 | RAS p21 protein activator (GTPase activating protein) 1 (RASA1), transcript variant 2 |
| NM_020781.2 | zinc finger protein 398 (ZNF398), transcript variant 2 |
| NM_002391.1 | midkine (neurite growth-promoting factor 2) (MDK), transcript variant 3 |
| NM_006298.2 | zinc finger protein 192 (ZNF192) |
| BC047536.1 | sciellin (SCEL) |
| NM_139062.1 | casein kinase 1, delta (CSNK1D), transcript variant 2 |
| NM_005639.1 | synaptotagmin I (SYT1) |
| BC006811.1 | peroxisome proliferator-activated receptor gamma (PPARG) |
| BC008364.1 | heterogeneous nuclear ribonucleoprotein C (C1/C2) (HNRPC) |
| NM_032345.1 | within bgcn homolog (*Drosophila*) (WIBG) |
| BC016825.1 | spire homolog 1 (*Drosophila*) (SPIRE1) |
| NM_020664.3 | 2,4-dienoyl CoA reductase 2, peroxisomal (DECR2) |

TABLE 1-continued

| Database ID | Description |
|---|---|
| NM_017542.3 | pogo transposable element with KRAB domain (POGK) |
| NM_003160.1 | Serine/threonine-protein kinase 13 |
| BC026346.1 | family with sequence similarity 84, member A (FAM84A) |
| BC041037.1 | immunoglobulin heavy constant mu (IGHM) |
| BC033677.1 | Uncharacterized protein C9orf114 |
| BC055427.1 | TRAF2 and NCK interacting kinase (TNIK) |
| NM_016648.1 | La ribonucleoprotein domain family, member 7 (LARP7), transcript variant 1 |
| BC064145.1 | CDK5 regulatory subunit associated protein 1-like 1 (CDKAL1) |
| NM_138565.1 | cortactin (CTTN), transcript variant 2 |
| NM_022823.1 | fibronectin type III domain containing 4 (FNDC4) |
| BC006104.1 | RIO kinase 1 (yeast) (RIOK1) |
| BC014975.1 | family with sequence similarity 136, member A (FAM136A) |
| NM_138730.1 | high mobility group nucleosomal binding domain 3 (HMGN3), transcript variant 2 |
| NM_025004.1 | Coiled-coil domain-containing protein 15 |
| NM_004092.2 | Enoyl-CoA hydratase, mitochondrial |
| NM_021107.1 | mitochondrial ribosomal protein S12 (MRPS12), nuclear gene encoding mitochondrial protein, transcript variant 1 |
| NM_053049.2 | Urocortin-3 |
| NM_001545.1 | immature colon carcinoma transcript 1 (ICT1) |
| NM_148571.1 | mitochondrial ribosomal protein L27 (MRPL27), nuclear gene encoding mitochondrial protein, transcript variant 2 |
| NM_001003799.1 | TCR gamma alternate reading frame protein (TARP), nuclear gene encoding mitochondrial protein, transcript variant 1 |
| BC017227.1 | phosducin-like (PDCL) |
| NM_172159.2 | potassium voltage-gated channel, shaker-related subfamily, beta member 1 (KCNAB1), transcript variant 3 |
| NM_000462.2 | ubiquitin protein ligase E3A (human papilloma virus E6-associated protein, Angelman syndrome) (UBE3A), transcript variant 2 |
| XM_210860.4 | PREDICTED: Homo sapiens hypothetical LOC283034 (LOC283034) |
| BC022344.1 | twinfilin, actin-binding protein, homolog 1 (Drosophila) (TWF1) |
| NM_005037.3 | peroxisome proliferator-activated receptor gamma (PPARG), transcript variant 4 |
| NM_022977.1 | acyl-CoA synthetase long-chain family member 4 (ACSL4), transcript variant 2 |
| NM_006217.2 | serpin peptidase inhibitor, clade I (pancpin), member 2 (SERPINI2) |
| NM_024979.2 | Guanine nucleotide exchange factor DBS |
| NM_016286.1 | dicarbonyl/L-xylulose reductase (DCXR) |
| NM_003160.1 | Serine/threonine-protein kinase 13 |
| NM_015687.2 | filamin A interacting protein 1 (FILIP1) |
| BC005871.2 | chromosome 10 open reading frame 58 (C10orf58) |
| NM_016216.2 | Lariat debranching enzyme |
| NM_017856.1 | gem (nuclear organelle) associated protein 8 (GEMIN8), transcript variant 3 |
| NM_015869.2 | peroxisome proliferator-activated receptor gamma (PPARG), transcript variant 2 |
| NM_001003397.1 | Tumor protein D53 |
| NM_001018061.1 | UPF0544 protein C5orf45 [Source: UniProtKB/Swiss-Prot; Acc: Q6NTE8] |
| BC013900.1 | chromosome 12 open reading frame 41 (C12orf41) |
| BC022988.1 | chromosome 6 open reading frame 65 (C6orf65) |
| NM_006299.2 | zinc finger protein 193 (ZNF193) |
| BC018847.1 | Transaldolase |
| NM_139355.1 | megakaryocyte-associated tyrosine kinase (MATK), transcript variant 1 |
| NM_207356.1 | chromosome 1 open reading frame 174 (C1orf174) |
| NM_001008737.1 | hypothetical LOC401052 (LOC401052) |
| NM_145109.1 | mitogen-activated protein kinase kinase 3 (MAP2K3), transcript variant B |
| BC017114.1 | oligonucleotide/oligosaccharide-binding fold containing 2A (OBFC2A) |
| XM_086879.4 | PREDICTED: Homo sapiens hypothetical LOC150371 (LOC150371) |
| NM_078630.1 | male-specific lethal 3-like 1 (Drosophila) (MSL3L1), transcript variant 2 |
| NM_005197.2 | Forkhead box protein N3 |
| NM_004602.2 | Double-stranded RNA-binding protein Staufen homolog 1 |
| BC017504.1 | Differentially expressed in FDCP 6 homolog |
| NM_003590.2 | cullin 3 (CUL3) |
| NM_145702.1 | tigger transposable element derived 1 (TIGD1) |
| BC001935.1 | cyclin-dependent kinase inhibitor 1A (p21, Cip1) (CDKN1A) |
| NM_004965.3 | high-mobility group nucleosome binding domain 1 (HMGN1) |
| BC032508.1 | PNMA-like 1, mRNA (cDNA clone MGC: 45422 IMAGE: 5246377), complete cds |

TABLE 1-continued

| Database ID | Description |
|---|---|
| BC013966.2 | family with sequence similarity 64, member A (FAM64A) |
| NM_020236.2 | mitochondrial ribosomal protein L1 (MRPL1), nuclear gene encoding mitochondrial protein |
| BC043247.2 | transducin-like enhancer of split 3 (E(sp1) homolog, *Drosophila*) (TLE3) |
| BC057806.1 | insulin-like growth factor binding protein 1 (IGFBP1) |
| NM_006573.2 | tumor necrosis factor (ligand) superfamily, member 13b (TNFSF13B) |
| BC025406.1 | phosphodiesterase 4D interacting protein (myomegalin) (PDE4DIP) |
| BC002559.1 | YTH domain family, member 2 (YTHDF2) |
| NM_052926.1 | Paraneoplastic antigen-like protein 5 |
| NM_006254.3 | protein kinase C, delta (PRKCD), transcript variant 1 |
| BC022003.1 | myotubularin related protein 9 (MTMR9) |
| BC043348.2 | retinitis pigmentosa 2 (X-linked recessive) (RP2) |
| NM_018010.2 | intraflagellar transport 57 homolog (*Chlamydomonas*) (IFT57) |
| BC044851.1 | vacuolar protein sorting 41 homolog (*S. cerevisiae*) (VPS41) |
| BC068094.1 | SH3 domain and tetratricopeptide repeats 1 (SH3TC1) |
| NM_020961.2 | KIAA1627 protein (KIAA1627) |
| PV3757 | myosin light chain kinase 2, skeletal muscle (MYLK2) |
| NM_002451.3 | methylthioadenosine phosphorylase (MTAP), mRNA. |
| NM_000281.1 | pterin-4 alpha-carbinolamine dehydratase/dimerization cofactor of hepatocyte nuclear factor 1 alpha (TCF1) (PCBD1) |
| NM_144982.1 | coiled-coil domain containing 131 (CCDC131) |
| NM_017927.2 | mitofusin 1 (MFN1), nuclear gene encoding mitochondrial protein, transcript variant 2 |
| NM_002150.1 | 4-hydroxyphenylpyruvate dioxygenase |
| NM_016267.1 | vestigial like 1 (*Drosophila*) (VGLL1) |
| BC067299.1 | Mdm4, transformed 3T3 cell double minute 4, p53 binding protein (mouse) (MDM4) |
| XM_378988.2 | PREDICTED: Homo sapiens hypothetical LOC400849 (LOC400849) |
| NM_006466.1 | polymerase (RNA) III (DNA directed) polypeptide F, 39 kDa (POLR3F) |
| BC042608.1 | family with sequence similarity 90, member A1 (FAM90A1) |
| NM_025136.1 | optic atrophy 3 (autosomal recessive, with chorea and spastic paraplegia) (OPA3), transcript variant 2 |
| BC012620.1 | golgi SNAP receptor complex member 1 (GOSR1) |
| NM_139244.2 | syntaxin binding protein 5 (tomosyn) (STXBP5) |
| NM_015929.2 | lipoyltransferase 1 (LIPT1), transcript variant 1 |
| PV3366 | v-erb-b2 erythroblastic leukemia viral oncogene homolog 2, neuro/glioblastoma derived oncogene homolog (avian) (ERBB2), transcript variant 2 |
| NM_133629.1 | RAD51-like 3 (*S. cerevisiae*) (RAD51L3), transcript variant 4 |
| XM_294794.1 | PREDICTED: Homo sapiens similar to putative membrane-bound dipeptidase 2 (LOC339065) |
| BC012289.1 | KIAA0515 (KIAA0515) |
| BC029444.1 | immunoglobulin kappa constant (IGKC) |
| BC015109.1 | 39S ribosomal protein L1, mitochondrial |
| NM_024578.1 | occludin/ELL domain containing 1 (OCEL1) |
| NM_003908.1 | eukaryotic translation initiation factor 2, subunit 2 beta, 38 kDa (EIF2S2) |
| BC001726.1 | Nucleolar protein 11 |
| BC003666.2 | NAD synthetase 1 (NADSYN1) |
| NM_198491.1 | family with sequence similarity 92, member B (FAM92B) |
| PV3817 | WEE1 homolog (*S. pombe*) (WEE1) |
| BC000974.2 | WDR45-like (WDR45L) |
| BC053675.1 | thymopoietin (TMPO) |
| BC033292.1 | interleukin 20 receptor beta (IL20RB) |
| BC002509.1 | PHD finger protein 23 |
| BC006969.1 | dynein, cytoplasmic 2, light intermediate chain 1, mRNA (cDNA clone MGC: 12166 IMAGE: 3828551), complete cds |
| BC069491.1 | Cerberus |
| NM_138559.1 | B-cell CLL/lymphoma 11A (zinc finger protein) (BCL11A), transcript variant 3 |
| BC004376.1 | annexin A8 (ANXA8L1) |
| NM_005620.1 | S100 calcium binding protein A11 (S100A11) |
| PV3872 | epidermal growth factor receptor (erythroblastic leukemia viral (v-erb-b) oncogene homolog, avian) (EGFR); see catalog number for detailed information on wild-type or point mutant status |
| NM_032214.1 | Src-like-adaptor 2 (SLA2), transcript variant 1 |
| NM_002444.1 | moesin (MSN) |
| NM_173796.2 | hypothetical protein MGC24125 (MGC24125) |
| NM_002648.1 | pim-1 oncogene (PIM1) |
| NM_001876.2 | Carnitine O-palmitoyltransferase 1, liver isoform |
| BC014532.1 | decapping enzyme, scavenger (DCPS) |
| NM_001005266.1 | Dresden prostate carcinoma protein 2 |
| NM_007172.2 | nucleoporin 50 kDa (NUP50), transcript variant 2 |
| NM_018326.1 | GTPase, IMAP family member 4 (GIMAP4) |

TABLE 1-continued

| Database ID | Description |
|---|---|
| BC033881.1 | XRCC6 binding protein 1 (XRCC6BP1) |
| NM_020168.3 | p21(CDKN1A)-activated kinase 6 (PAK6) |
| NM_014790.3 | janus kinase and microtubule interacting protein 2 (JAKMIP2) |
| NM_032360.1 | acyl-Coenzyme A binding domain containing 6 (ACBD6) |
| NM_006303.2 | JTV1 gene (JTV1) |
| BC017305.1 | sirtuin (silent mating type information regulation 2 homolog) 7 (S. cerevisiae) (SIRT7) |
| BC051762.1 | Uncharacterized protein C20orf96 |
| NM_145010.1 | chromosome 10 open reading frame 63 (C10orf63) |
| NM_206834.1 | Uncharacterized protein C6orf201 |
| BC009350.1 | Eukaryotic translation initiation factor 2-alpha kinase 4 |
| NM_003720.1 | Proteasome assembly chaperone 1 |
| BC067755.1 | potassium channel tetramerisation domain containing 18 (KCTD18) |
| BC005840.2 | selenoprotein S (SELS) |
| BC000934.2 | eukaryotic translation initiation factor 2, subunit 2 beta, 38 kDa (EIF2S2) |
| NM_020175.1 | dihydrouridine synthase 3-like (S. cerevisiae) (DUS3L) |
| BC014667.1 | immunoglobulin heavy constant gamma 1 (G1m marker) (IGHG1) |
| NM_201403.1 | MOB1, Mps One Binder kinase activator-like 2C (yeast) (MOBKL2C), transcript variant 2 |
| BC010537.1 | SUB1 homolog (S. cerevisiae) (SUB1) |
| NM_170746.2 | Selenoprotein H |
| NM_003092.3 | small nuclear ribonucleoprotein polypeptide B'' (SNRPB2), transcript variant 1 |
| NM_005105.2 | RNA binding motif protein 8A (RBM8A) |
| BC047411.1 | tubulin tyrosine ligase-like family, member 2 (TTLL2) |
| NM_199188.1 | La ribonucleoprotein domain family, member 4 (LARP4), transcript variant 2 |
| BC003551.1 | transglutaminase 2 (C polypeptide, protein-glutamine-gamma-glutamyltransferase) (TGM2) |
| BC020647.1 | coiled-coil domain containing 59 (CCDC59) |
| BC011781.2 | chromosome 9 open reading frame 37 (C9orf37) |
| NM_032858.1 | maelstrom homolog (Drosophila) (MAEL) |
| NM_144971.1 | hypothetical protein MGC26641 (MGC26641) |
| BC017440.1 | trafficking protein particle complex 2-like (TRAPPC2L) |
| BC017018.1 | DnaJ (Hsp40) homolog, subfamily C, member 12 (DNAJC12) |
| NM_144767.3 | A kinase (PRKA) anchor protein 13 (AKAP13), transcript variant 3 |
| NM_018297.2 | N-glycanase 1 (NGLY1) |
| NM_002307.1 | lectin, galactoside-binding, soluble, 7 (galectin 7) (LGALS7) |
| NM_003939.2 | beta-transducin repeat containing (BTRC), transcript variant 2, mRNA. |
| NM_013242.1 | chromosome 16 open reading frame 80 (C16orf80) |
| NM_152285.1 | arrestin domain containing 1 (ARRDC1) |
| NM_178425.1 | histone deacetylase 9 (HDAC9), transcript variant 5 |
| NM_007255.1 | xylosylprotein beta 1,4-galactosyltransferase, polypeptide 7 (galactosyltransferase I) (B4GALT7) |
| NM_205833.1 | immunoglobulin superfamily, member 1 (IGSF1), transcript variant 2 |
| BC040457.1 | calcium/calmodulin-dependent protein kinase (CaM kinase) II alpha (CAMK2A) |
| NM_004732.1 | potassium voltage-gated channel, shaker-related subfamily, beta member 3 (KCNAB3) |
| NM_004450.1 | enhancer of rudimentary homolog (Drosophila) (ERH) |
| XM_378582.2 | PREDICTED: Homo sapiens hypothetical LOC400523 (LOC400523) |
| NM_001006666.1 | apolipoprotein B mRNA editing enzyme, catalytic polypeptide-like 3F (APOBEC3F), transcript variant 2, mRNA. |
| BC041876.1 | tau tubulin kinase 2 (TTBK2) |
| BC036335.1 | BTB (POZ) domain containing 12 (BTBD12) |
| BC036099.1 | aryl-hydrocarbon receptor nuclear translocator 2 (ARNT2) |
| NM_054012.1 | argininosuccinate synthetase 1 (ASS1), transcript variant 2 |
| NM_057749.1 | cyclin E2 (CCNE2) |
| PV3839 | CDC-like kinase 4 (CLK4) |
| BC005026.1 | sirtuin (silent mating type information regulation 2 homolog) 6 (S. cerevisiae) (SIRT6) |
| NM_013975.1 | ligase III, DNA, ATP-dependent (LIG3), nuclear gene encoding mitochondrial protein, transcript variant alpha |
| NM_181509.1 | microtubule-associated protein 1 light chain 3 alpha (MAP1LC3A), transcript variant 2 |
| BC001709.1 | NAD kinase (NADK) |
| NM_002638.1 | peptidase inhibitor 3, skin-derived (SKALP) (PI3) |
| NM_005901.2 | SMAD family member 2 (SMAD2), transcript variant 1 |
| BC046199.1 | family with sequence similarity 72, member B (FAM72B) |
| NM_015417.2 | sperm flagellar 1 (SPEF1) |
| NM_018328.1 | methyl-CpG binding domain protein 5 (MBD5) |
| BC017328.2 | angiotensin II receptor-associated protein (AGTRAP) |
| NM_182739.1 | NADH dehydrogenase (ubiquinone) 1 beta subcomplex, 6, 17 kDa (NDUFB6), nuclear gene encoding mitochondrial protein, transcript variant 2 |

TABLE 1-continued

| Database ID | Description |
|---|---|
| NM_001032293.1 | zinc finger protein 207 (ZNF207), transcript variant 2 |
| NM_012227.1 | Putative GTP-binding protein 6 |
| BC026039.1 | mitochondrial GTPase 1 homolog (*S. cerevisiae*) (MTG1) |
| BC072409.1 | Serine/threonine-protein phosphatase 4 regulatory subunit 3A |
| BC066938.1 | DEAD (Asp-Glu-Ala-Asp) box polypeptide 43 (DDX43) |
| BC000712.1 | kinesin family member C1 (KIFC1) |
| BC000052.1 | peroxisome proliferator-activated receptor alpha (PPARA) |
| NM_004117.2 | FK506 binding protein 5 (FKBP5) |
| NM_002629.2 | phosphoglycerate mutase 1 (brain) (PGAM1) |
| NM_015122.1 | FCH domain only 1 (FCHO1) |
| NM_001021.2 | ribosomal protein S17 (RPS17) |
| NM_013323.1 | sorting nexin 11 (SNX11), transcript variant 2 |
| BC002950.1 | chromosome 18 open reading frame 8 (C18orf8) |
| NM_017612.1 | Zinc finger CCHC domain-containing protein 8 |
| BC035048.2 | neurogenic differentiation 6 (NEUROD6) |
| BC046117.1 | dynein, axonemal, light intermediate chain 1 (DNALI1) |
| NM_005335.3 | Hematopoietic lineage cell-specific protein |
| NM_144679.1 | chromosome 17 open reading frame 56 (C17orf56) |
| NM_004881.1 | tumor protein p53 inducible protein 3 (TP53I3), transcript variant 1 |
| NM_199334.2 | thyroid hormone receptor, alpha (erythroblastic leukemia viral (v-erb-a) oncogene homolog, avian) (THRA), transcript variant 1 |
| NM_201567.1 | cell division cycle 25 homolog A (*S. pombe*) (CDC25A), transcript variant 2 |
| BC012945.1 | Uncharacterized protein C19orf57 |
| BC043394.1 | ankyrin repeat domain 17 (ANKRD17) |
| NM_053005.2 | HCCA2 protein (HCCA2) |
| NM_175065.2 | histone cluster 2, H2ab (HIST2H2AB) |
| NM_004706.3 | Rho guanine nucleotide exchange factor (GEF) 1 (ARHGEF1), transcript variant 2 |
| NM_014346.1 | TBC1 domain family, member 22A (TBC1D22A) |
| NM_133480.1 | transcriptional adaptor 3 (NGG1 homolog, yeast)-like (TADA3L), transcript variant 2 |
| BC048969.1 | TSPY-like 1 (TSPYL1) |
| NM_020319.1 | ankyrin repeat and MYND domain containing 2 (ANKMY2) |
| NM_016046.2 | exosome component 1 (EXOSC1) |
| NM_001003396.1 | tumor protein D52-like 1 (TPD52L1), transcript variant 3 |
| NM_005870.3 | Histone deacetylase complex subunit SAP18 |
| NM_003403.3 | YY1 transcription factor (YY1) |
| BC036096.2 | zinc finger protein 18 (ZNF18) |
| NM_001010844.1 | Interleukin-1 receptor-associated kinase 1-binding protein 1 |
| BC029524.1 | Coiled-coil domain-containing protein 46 |
| NM_152387.2 | BTB/POZ domain-containing protein KCTD18 |
| BC002369.1 | Serine/threonine-protein kinase PLK1 |
| BC092404.1 | Rap guanine nucleotide exchange factor 3 |
| NM_004922.2 | SEC24 related gene family, member C (*S. cerevisiae*) (SEC24C), transcript variant 1 |
| NM_198217.1 | Inhibitor of growth protein 1 |
| BC051911.1 | chromosome 13 open reading frame 24 (C13orf24) |
| NM_006205.1 | phosphodiesterase 6H, cGMP-specific, cone, gamma (PDE6H) |
| NM_006439.3 | Protein mab-21-like 2 |
| NM_173456.1 | phosphodiesterase 8A (PDE8A), transcript variant 4 |
| BC019268.1 | Protein arginine N-methyltransferase 1 |
| NM_173642.1 | family with sequence similarity 80, member A (FAM80A) |
| NM_194299.1 | Synaptonemal complex protein 2-like |
| BC062323.1 | chromosome 21 open reading frame 25 (C21orf25) |
| NM_021709.1 | Apoptosis regulatory protein Siva |
| BC100813.1 | Putative T-complex protein 1 subunit theta-like 2 |
| BC026317.1 | solute carrier family 16, member 1 (monocarboxylic acid transporter 1) (SLC16A1) |
| BC010956.1 | Keratinocyte growth factor |
| NM_005034.2 | polymerase (RNA) II (DNA directed) polypeptide K, 7.0 kDa (POLR2K) |
| BC024291.1 | BR serine/threonine kinase 2 (BRSK2) |
| NM_001001568.1 | phosphodiesterase 9A (PDE9A), transcript variant 3, mRNA. |
| NM_014314.3 | Probable ATP-dependent RNA helicase DDX58 |
| BC047420.1 | UBX domain-containing protein 7 |
| NM_000430.2 | platelet-activating factor acetylhydrolase, isoform Ib, alpha subunit 45 kDa (PAFAH1B1) |
| PV3873 | epidermal growth factor receptor (erythroblastic leukemia viral (v-erb-b) oncogene homolog, avian) (EGFR); see catalog number for detailed information on wild-type or point mutant status |
| NM_001328.1 | C-terminal binding protein 1 (CTBP1), transcript variant 1 |
| NM_001009959.1 | Ermin |
| BC050387.1 | ankyrin repeat and sterile alpha motif domain containing 3 (ANKS3) |
| NM_007194.1 | Serine/threonine-protein kinase Chk2 |
| NM_018492.2 | PDZ binding kinase (PBK) |
| NM_182801.1 | EGF-like, fibronectin type III and laminin G domains (EGFLAM), transcript variant 4 |

TABLE 1-continued

| Database ID | Description |
|---|---|
| BC016615.1 | RAB37, member RAS oncogene family (RAB37) |
| BC008950.2 | Prenylated Rab acceptor protein 1 |
| BC041831.1 | transducin-like enhancer of split 3 (E(sp1) homolog, *Drosophila*) (TLE3) |
| NM_003104.2 | sorbitol dehydrogenase (SORD) |
| BC003555.1 | nucleolar complex associated 2 homolog (*S. cerevisiae*) (NOC2L) |
| NM_001274.2 | CHK1 checkpoint homolog (*S. pombe*) (CHEK1) |
| NM_153645.1 | nucleoporin 50 kDa (NUP50), transcript variant 3 |
| BC017423.1 | mesoderm induction early response 1 homolog (Xenopus laevis) (MIER1) |
| BC007424.2 | PRP4 pre-mRNA processing factor 4 homolog (yeast) (PRPF4) |
| NM_007107.2 | signal sequence receptor, gamma (translocon-associated protein gamma) (SSR3) |
| XM_096472.2 | hypothetical LOC143678 (LOC143678) |
| NM_015698.2 | G patch domain and KOW motifs (GPKOW) |
| NM_018111.1 | Putative uncharacterized protein FLJ10490 |
| NM_006694.1 | jumping translocation breakpoint (JTB) |
| NM_000045.2 | arginase, liver (ARG1) |
| BC074765.2 | POU domain, class 6, transcription factor 1 |
| NM_172028.1 | ankyrin repeat and BTB (POZ) domain containing 1 (ABTB1), transcript variant 3 |
| BC026345.1 | Ermin |
| NM_201262.1 | DnaJ (Hsp40) homolog, subfamily C, member 12 (DNAJC12), transcript variant 2 |
| NM_002966.1 | S100 calcium binding protein A10 (S100A10) |
| BC013352.1 | HpaII tiny fragments locus 9c protein |
| NM_004873.1 | BCL2-associated athanogene 5 (BAG5), transcript variant 2 |
| BC009415.1 | kinesin family member 26A (KIF26A) |
| BC012539.1 | mediator complex subunit 31 (MED31) |
| BC021247.1 | Phosphatase and actin regulator 4 |
| NM_004414.3 | regulator of calcineurin 1 (RCAN1), transcript variant 1 |
| BC028840.1 | ankyrin repeat domain 13C (ANKRD13C) |
| BC025787.1 | alkB, alkylation repair homolog 1 (*E. coli*) (ALKBH1) |
| NM_000459.1 | Angiopoietin-1 receptor |
| NM_000788.1 | Deoxycytidine kinase |
| NM_173859.1 | breast cancer and salivary gland expression gene (RP11-49G10.8) |
| NM_152382.1 | JmjC domain-containing protein C2orf60 |
| NM_002038.2 | interferon, alpha-inducible protein 6 (IFI6), transcript variant 1 |
| BC034984.1 | Kinesin-like protein KIF16B |
| NM_014582.1 | odorant binding protein 2A (OBP2A) |
| BC057760.1 | MORN repeat-containing protein 3 |
| NM_005595.1 | nuclear factor I/A (NFIA) |
| NM_032726.1 | phospholipase C, delta 4 (PLCD4) |
| NM_153276.1 | solute carrier family 22 (organic anion transporter), member 6 (SLC22A6), transcript variant 2 |
| NM_001011538.1 | similar to 60S ribosomal protein L21 (LOC402176) |
| NM_006433.2 | granulysin (GNLY), transcript variant NKG5 |
| NM_024800.1 | Serine/threonine-protein kinase Nek11 |
| NM_015850.2 | Basic fibroblast growth factor receptor 1 |
| NM_006590.2 | ubiquitin specific peptidase 39 (USP39) |
| NM_199054.1 | MAP kinase interacting serine/threonine kinase 2 (MKNK2), transcript variant 2 |
| BC050696.1 | chromosome 12 open reading frame 48 (C12orf48) |
| NM_024563.1 | chromosome 5 open reading frame 23 (C5orf23) |
| NM_004832.1 | glutathione S-transferase omega 1 (GSTO1) |
| NM_003242.2 | transforming growth factor, beta receptor II (70/80 kDa) (TGFBR2), transcript variant 2 |
| BC050444.1 | golgi autoantigen, golgin subfamily a, 4 (GOLGA4) |
| NM_201259.1 | Mitochondrial import inner membrane translocase subunit TIM14 |
| NM_032124.3 | haloacid dehalogenase-like hydrolase domain containing 2 (HDHD2) |
| NM_002870.1 | RAB13, member RAS oncogene family (RAB13) |
| BC000337.2 | glucose-6-phosphate dehydrogenase (G6PD) |
| BC060785.1 | tripartite motif-containing 40 (TRIM40) |
| BC030597.1 | ATR interacting protein (TREX1) |
| BC050551.1 | BCL2-associated athanogene 5 (BAG5) |
| NM_004697.3 | PRP4 pre-mRNA processing factor 4 homolog (yeast) (PRPF4) |
| NM_020990.2 | creatine kinase, mitochondrial 1B (CKMT1B), nuclear gene encoding mitochondrial protein |
| BC039742.1 | poly(rC) binding protein 1 (PCBP1) |
| BC021573.1 | GTP-binding protein 10 |
| NM_015068.1 | paternally expressed 10 (PEG10), transcript variant 1 |
| NM_001827.1 | CDC28 protein kinase regulatory subunit 2 (CKS2) |
| NM_152876.1 | Tumor necrosis factor receptor superfamily member 6 |
| BC015548.1 | RAB3A interacting protein (rabin3) (RAB3IP) |
| BC062359.1 | chromosome 8 open reading frame 47 (C8orf47) |
| BC029424.1 | Probable glutathione peroxidase 8 |

TABLE 1-continued

| Database ID | Description |
|---|---|
| NM_001786.2 | cell division cycle 2, G1 to S and G2 to M (CDC2), transcript variant 1 |
| BC000870.1 | TIMELESS interacting protein (TIPIN) |
| NM_004103.2 | Protein tyrosine kinase 2 beta |
| BC022454.2 | Transient receptor potential cation channel subfamily M member 3 |
| NM_024046.1 | CaM kinase-like vesicle-associated (CAMKV) |
| BC040521.1 | testis expressed 2 (TEX2) |
| BC003164.1 | leukocyte receptor cluster (LRC) member 4 (LENG4) |
| NM_000402.2 | Glucose-6-phosphate 1-dehydrogenase |
| BC069328.1 | Bcl2 modifying factor (BMF) |
| BC063463.1 | coenzyme Q3 homolog, methyltransferase (*S. cerevisiae*) (COQ3) |
| NM_000572.2 | Interleukin-10 |
| NM_006374.2 | serine/threonine kinase 25 (STE20 homolog, yeast) (STK25) |
| NM_017966.1 | vacuolar protein sorting 37 homolog C (*S. cerevisiae*) (VPS37C) |
| BC052602.1 | carbonic anhydrase XIII (CA13) |
| BC018063.1 | potassium channel tetramerisation domain containing 4 (KCTD4) |
| NM_031305.1 | Rho GTPase activating protein 24 (ARHGAP24), transcript variant 2 |
| BC056401.1 | centaurin, delta 2 (CENTD2) |
| BC022459.1 | sulfotransferase family 4A, member 1 (SULT4A1) |
| XM_373630.2 | PREDICTED: *Homo sapiens* hypothetical protein LOC145842 (LOC145842) |
| P3049 | v-abl Abelson murine leukemia viral oncogene homolog 1 (ABL1), transcript variant a; see catalog number for detailed information on wild-type or point mutant status |
| NM_153012.1 | Tumor necrosis factor ligand superfamily member 12 |
| NM_018270.3 | MRG-binding protein |
| BC010739.1 | COP9 signalosome complex subunit 7b |
| NM_015002.2 | F-box protein 21 (FBXO21), transcript variant 2 |
| BC000497.1 | CaM kinase-like vesicle-associated protein |
| NM_001449.2 | four and a half LIM domains 1 (FHL1) |
| BC065912.1 | Tyrosine-protein kinase ABL2 |
| NM_153356.1 | TBC1 domain family, member 21 (TBC1D21) |
| BC032382.1 | similar to pleckstrin homology domain containing, family M (with RUN domain) member 1; adapter protein 162, mRNA, complete cds. |
| BC094800.1 | Jouberin |
| NM_003897.2 | immediate early response 3 (IER3) |
| NM_178821.1 | WD repeat domain 69 (WDR69) |
| NM_198219.1 | Inhibitor of growth protein 1 |
| NM_024805.1 | chromosome 18 open reading frame 22 (C18orf22) |
| NM_001040633.1 | protein kinase, AMP-activated, gamma 2 non-catalytic subunit (PRKAG2), transcript variant c, mRNA. |
| NM_130807.1 | MOB1, Mps One Binder kinase activator-like 2A (yeast) (MOBKL2A) |
| BC008623.1 | roundabout, axon guidance receptor, homolog 3 (*Drosophila*) (ROBO3) |
| NM_001004285.1 | DNA fragmentation factor, 40 kDa, beta polypeptide (caspase-activated DNase) (DFFB), transcript variant 3 |
| BC011885.1 | eukaryotic translation initiation factor 2A, 65 kDa (EIF2A) |

Thus in one embodiment, the present invention provides a method for detecting AD diagnostic biomarkers in a subject in need of such detection comprising obtaining an immunoglobulin-containing biological sample from the subject, and performing an assay to determine the presence or absence of one or more AD diagnostic biomarkers in the biological sample.

In another embodiment, the present invention provides a method for diagnosing Alzheimer's Disease (AD) in a subject in need of such diagnosis comprising obtaining an immunoglobulin-containing biological sample from the subject, performing an assay to determine the presence or absence of one or more AD diagnostic biomarkers in the biological sample, and diagnosing AD if one or more AD diagnostic biomarkers are present.

In a preferred embodiment, the subject is a human subject.

In a preferred embodiment of the invention, the immunoglobulin-containing biological sample is serum, whole blood, CSF, saliva, or sputum. A blood sample may be obtained by methods known in the art including venipuncture or a finger stick. CSF may be obtained by methods known in the art including a lumbar spinal tap. To obtain serum from blood, a sample of blood is received and centrifuged at a speed sufficient to pellet all cells and platelets, and the serum to be analyzed is drawn from the resulting supernatant. Sputum and saliva samples may be collected by methods known in the art. The biological samples may be diluted with a suitable buffer before conducting the assay. In a preferred embodiment, the biological sample is serum or whole blood.

Assays to determine the presence or absence of one or more AD diagnostic biomarkers in the biological sample are performed by contacting the sample with one or more autoantigens that are specific for an AD diagnostic biomarker under conditions that allow an immunocomplex of the autoantigen and the antibody to form, and detecting the presence of the immunocomplex An autoantigen may comprise a protein antigen of Table 1, or a polypeptide or peptide fragment thereof containing one or more epitopes recognized by the AD diagnostic biomarker, or an epitope peptidomimetic that is recognized by the AD diagnostic biomarker. Peptidomimetics include, for example, D-peptides, peptoids, and β-peptides. The autoantigens may be purified from natural sources, or produced recombinantly or synthetically by methods known in the art, and may be in the form of fusion proteins. The autoantigens may be produced in vitro using cell-free translation systems. In one preferred embodiment, the autoantigens are produced in a mammalian or insect expression system to ensure correct folding and function. All of these methods may be automated for high throughput production.

Assays and conditions for the detection of immunocomplexes are known to those of skill in the art. Such assays include, for example, competition assays, direct reaction assays and sandwich-type assays. The assays may be quantitative or qualitative. In one preferred embodiment, the assay utilizes a solid phase or substrate to which the autoantigens are directly or indirectly attached, such as a microtiter or microassay plate, slide, magnetic bead, non-magnetic bead, column, matrix, membrane, or sheet, and may be composed of a synthetic material such as polystyrene, polyvinyl chloride, polyamide, or other synthetic polymers, natural polymers such as cellulose, derivatized natural polymers such as cellulose acetate or nitrocellulose, and glass, for example glass fibers. The substrate preferably comprises a plurality of individually addressable autoantigens immobilized on the surface. The individually addressable autoantigens are preferably immobilized on the surface to form an array. The substrates may be used in suitable shapes, such as films, sheets, or plates, or may be coated onto or bonded or laminated to appropriate inert carriers, such as paper, glass, plastic films, or fabrics. In a preferred embodiment, the substrate is a slide or a bead.

Methods for attaching the autoantigens to the support or substrate are known in the art and include covalent and noncovalent interactions. For example, diffusion of applied proteins into a porous surface such a hydrogel allows noncovalent binding of unmodified protein within hydrogel structures. Covalent coupling methods provide a stable linkage and may be applied to a range of proteins. Biological capture methods utilising a tag (e.g., hexahistidine/Ni-NTA or biotin/avidin) on the protein and a partner reagent immobilized on the surface of the substrate provide a stable linkage and bind the protein specifically and in reproducible orientation.

In one preferred embodiment, the autoantigens are coated or spotted onto the support or substrate such as chemically derivatized glass.

In one preferred embodiment the autoantigens are provided in the form of an array, and preferably a microarray. Protein microarrays are known in the art and reviewed for example by Hall et al. (2007) *Mech Ageing Dev* 128:161-167 and Stoevesandt et al (2009) *Expert Rev Proteomics* 6:145-157, the disclosures of which are incorporated herein by reference. Microarrays may be prepared by immobilizing purified autoantigens on a substrate such as a treated microscope slide using a contact spotter or a non-contact microarrayer. Microarrays may also be produced through in situ cell-free synthesis directly from corresponding DNA arrays.

Suitable methods for external production and purification of autoantigens to be spotted on arrays include expression in bacteria, as disclosed for example by Venkataram et al. (2008) *Biochemistry* 47:6590-6601, in yeast, as disclosed for example by Li et al. (2007) *Appl Biochem Biotechnol.* 142:105-124, in insect cells, as disclosed for example by Altman et al. (1999) *Glycoconj J* 16:109-123, and in mammalian cells, as disclosed for example by Spampinato et al. (2007) *Curr Drug Targets* 8:137-146.

Suitable methods for in situ ("on-chip") protein production are disclosed, for example, by Ramachandran et al. (2006) *Methods Mol. Biol* 2328:1-14 and He et al. (2008) *Curr. Opin Biotechnol* 19:4-9.

Other methods by which proteins are simultaneously expressed and immobilized in parallel on an array surface are also known in the art and may be used in accordance with the present invention. For example, in the Protein In Situ Arrays (PISA) method (He et al. (2001) *Nucleic Acids Res* 29:e73), proteins are made directly from DNA, either in solution or immobilized, and become attached to the array surface as they are made through recognition of a tag sequence. The proteins are expressed in parallel in vitro utilizing a cell free system, commonly rabbit reticulocyte or *E. coli* S30, to perform coupled transcription and translation. In this method, protein expression is performed on a surface which is precoated with an immobilizing agent capable of binding to the tag. Thus after each protein is translated, it becomes fixed simultaneously and specifically to the adjacent surface, while the other materials can subsequently be washed away. Microarrays are produced directly onto glass slides, either by mixing the DNA with the cell free lysate system before spotting or by a multiple spotting technique (MIST) in which DNA is spotted first followed by the expression system.

In the system known as Nucleic Acid Programmable Protein Array (NAPPA) (Ramachandran et al. (2004) *Science* 305:86-90), transcription and translation from an immobilized (as opposed to a solution) DNA template allow conversion of DNA arrays to protein arrays. In this method, biotinylated cDNA plasmids encoding the proteins as GST fusions are printed onto an avidin-coated slide, together with an anti-GST antibody acting as the capture entity. The cDNA array is then covered with rabbit reticulocyte lysate to express the proteins, which become trapped by the antibody adjacent to each DNA spot, the proteins thereby becoming immobilized with the same layout as the cDNA. This technology generates a protein array in which the immobilized proteins are present together with DNA and a capture agent.

Another suitable method for generating a protein array is the DNA Array to Protein Array (DAPA) method. This method for in situ protein arraying uses an immobilized DNA array as the template to generate 'pure' protein arrays on a separate surface from the DNA, and also can produce multiple copies of a protein array from the same DNA template (He et al. (2008) *Nature Methods,* 5:175-7). Cell-free protein synthesis is performed in a membrane held between two surfaces (e.g., glass slides), one of which is arrayed with DNA molecules while the other surface carries a specific reagent to capture the translated proteins. Individual, tagged proteins are synthesized in parallel from the arrayed DNA, diffuse across the gap and are subsequently immobilized through interaction with the tag-capturing reagent on the opposite surface to form a protein array. Discrete spots which accurately reflect the DNA in position and quantity are produced. Replicate copies of the protein array can be obtained by reuse of the DNA.

Array fabrication methods include robotic contact printing, ink-jetting, piezoelectric spotting and photolithography. For example, purified autoantigens of the invention that are produced and purified externally may be spotted onto a microarray substrate using a flexible protein microarray inkjet printing system (e.g., ArrayJet, Roslin, Scotland, UK) to provide high quality protein microarray production. The precise rows and columns of autoantigens may be converted to detectable spots denoting both the presence and amount of serum diagnostic biomarkers that have been bound.

The production of the microarrays is preferably performed with commercially available printing buffers designed to maintain the three-dimensional shape of the autoantigens. In one preferred embodiment, the substrate for the microarray is a nitrocellulose-coated glass slide.

The assays are performed by methods known in the art in which the one or more autoantigens are contacted with the biological sample under conditions that allow the formation of an immunocomplex of an autoantigen and an antibody, and detecting the immunocomplex. The presence and amount of the immunocomplex may be detected by methods known in the art, including label-based and label-free detection. For example, label-based detection methods include addition of a secondary antibody that is coupled to an indicator reagent comprising a signal generating compound. The secondary antibody may be an anti-human IgG antibody. Indicator reagents include chromogenic agents, catalysts such as enzyme conjugates, fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors and magnetic particles. Examples of enzyme conjugates include alkaline phosphatase, horseradish peroxidase and beta-galactosidase. Methods of label-free detection include surface plasmon resonance, carbon nanotubes and nanowires, and interferometry. Label-based and label-free detection methods are known in the art and disclosed, for example, by Hall et al. (2007) and by Ray et al. (2010) Proteomics 10:731-748. Detection may be accomplished by scanning methods known in the art and appropriate for the label used, and associated analytical software.

In one preferred embodiment of the present invention, fluorescence labeling and detection methods are used to detect the immunocomplexes. Commericially available slide scanners (e.g. the Genepix 4000B slide scanner (Molecular Devices, Inc.) with associated analytical software may be used. In one preferred embodiment, the immunocomplex is probed with fluorescent-labeled (e.g., Alexa-Fluor (Invitrogen)) anti-human antibody and the intensity of fluorescence at each protein spot is measured using a microarray scanner. Commercially available software (e.g. GenePix Pro 5.0 software (Axon instruments)) may be used to extract the net median pixel intensities for individual features from the digital images produced by the scanner. Data may be normalized by comparing median values of multiple identical control spots in different regions of the same array.

Detection of diagnostic immunocomplexes is indicative of the presence of AD diagnostic biomarkers in the biological sample, and thus a positive diagnosis of AD.

In another embodiment, the present invention provides a method of generating a patient-specific AD diagnostic biomarker profile comprising obtaining a serum-containing biological sample from a patient, performing an assay to determine the presence or absence of AD diagnostic biomarkers in the biological sample, and generating a patient-specific AD diagnostic biomarker profile of the AD diagnostic biomarkers present in the sample. The assay is performed as described hereinabove.

The results of the assay provide an AD diagnostic biomarker profile for the patient that is useful to diagnose AD and optimize a treatment regimen for AD.

In another embodiment, the present invention provides a method of identifying a subject at risk for developing AD comprising obtaining an immunoglobulin-containing biological sample from the subject, performing an assay to determine the presence or absence of one or more AD diagnostic biomarkers in the biological sample, and identifying the subject as at risk for developing AD if one or more of the AD diagnostic biomarkers is present. The assay is performed as described herein above.

In yet another embodiment, the present invention provides a substrate on which one or more autoantigens that are specific for an AD diagnostic biomarker are immobilized. The present invention also provides, in another embodiment, a microarray comprising a substrate on which one or more autoantigens that are specifically bound by an AD diagnostic biomarker are immobilized. The substrates and microarrays may be made as described hereinabove and are useful for creating AD diagnostic biomarker profiles and for the diagnosis of AD. An autoantigen may comprise a protein antigen of Table 1, or a polypeptide or peptide fragment thereof containing one or more epitopes recognized by the AD diagnostic biomarker, or an epitope peptidomimetic that is recognized by the AD diagnostic biomarker. Peptidomimetics include, for example, D-peptides, peptoids, and β-peptides. The substrate and microarrays may contain, as the autoantigen, at least one of the protein antigens of Table 1 or fragments thereof containing one or more epitopes recognized by the AD diagnostic biomarker.

In another embodiment, the substrate and microarrays may contain, as the autoantigen, at least one of the protein antigens of Table 2, or a polypeptide or peptide fragment thereof containing one or more epitopes recognized by the AD diagnostic biomarker, or an epitope peptidomimetic that is recognized by the AD diagnostic biomarker. Peptidomimetics include, for example, D-peptides, peptoids, and β-peptides. The protein antigens in Tables 2-5 are identified by art-accepted names as well as database identification numbers. The database identification numbers refer to the publically available protein databases of the National Center for Biotechnology Information (NCBI) which are well-known and accessible to those of ordinary skill in the art.

TABLE 2

| Database ID | Description |
| --- | --- |
| BC030984.1 | cDNA clone MGC: 32654 IMAGE: 4701898, complete cds |
| PHR5001 | Recombinant human CTLA-4/Fc |
| BC016380.1 | cDNA clone MGC: 27376 IMAGE: 4688477, complete cds |
| BC015833.1 | cDNA clone MGC: 27152 IMAGE: 4691630, complete cds |
| BC099907.1 | General transcription factor II-I |
| BC051695.1 | FERM domain containing 8 (FRMD8) |
| BC040106.1 | hypothetical protein HSPC111 (HSPC111) |
| NM_003141.2 | tripartite motif-containing 21 (TRIM21) |
| NM_003384.1 | vaccinia related kinase 1 (VRK1) |
| BC004236.2 | ubiquitin-conjugating enzyme E2S (UBE2S) |
| BC001662.1 | MAP kinase-activated protein kinase 3 |
| NM_017588.1 | WD repeat domain 5 (WDR5), transcript variant 1 |
| NM_032377.2 | elongation factor 1 homolog (S. cerevisiae) (ELOF1) |
| NM_021032.2 | fibroblast growth factor 12 (FGF12), transcript variant 1 |
| NM_000984.2 | ribosomal protein L23a (RPL23A) |
| BC064984.1 | additional sex combs like 1 (Drosophila) (ASXL1) |
| NM_012387.1 | peptidyl arginine deiminase, type IV (PADI4) |
| NM_001641.2 | APEX nuclease (multifunctional DNA repair enzyme) 1 (APEX1), transcript variant 1 |
| NM_001896.2 | casein kinase 2, alpha prime polypeptide (CSNK2A2) |
| NM_014481.2 | APEX nuclease (apurinic/apyrimidinic endonuclease) 2 (APEX2), nuclear gene encoding mitochondrial protein |
| NM_014280.1 | DnaJ homolog subfamily C member 8 |
| BC007228.1 | CSAG family, member 3A (CSAG3A) |
| BC021174.1 | Small EDRK-rich factor 1 |
| BC033758.1 | centaurin, alpha 2 (CENTA2) |
| BC005248.1 | eukaryotic translation initiation factor 1A, Y-linked (EIF1AY) |

TABLE 2-continued

| Database ID | Description |
|---|---|
| BC022098.1 | cDNA clone MGC: 31944 IMAGE: 4878869, complete cds |
| NM_024754.2 | pentatricopeptide repeat domain 2 (PTCD2) |
| NM_024316.1 | leukocyte receptor cluster (LRC) member 1 (LENG1) |
| NM_015920.3 | 40S ribosomal protein S27-like protein |
| BC048970.1 | tubulin tyrosine ligase-like family, member 7 (TTLL7) |
| NM_003668.2 | mitogen-activated protein kinase-activated protein kinase 5 (MAPKAPK5), transcript variant 1 |
| NM_007278.1 | GABA(A) receptor-associated protein (GABARAP) |
| NM_006838.1 | methionyl aminopeptidase 2 (METAP2) |
| NM_018439.1 | Impact homolog (mouse) (IMPACT) |
| NM_002013.2 | FK506 binding protein 3, 25 kDa (FKBP3) |
| NM_018956.2 | chromosome 9 open reading frame 9 (C9orf9) |
| NM_004987.3 | LIM and senescent cell antigen-like-containing domain protein 1 |
| BC004292.1 | PHD finger protein 15 (PHF15) |
| NM_133494.1 | NIMA (never in mitosis gene a)- related kinase 7 (NEK7) |
| NM_145063.1 | chromosome 6 open reading frame 130 (C6orf130) |
| NM_021104.2 | ribosomal protein L41 (RPL41), transcript variant 1 |
| NM_006223.1 | protein (peptidylprolyl cis/trans isomerase) NIMA-interacting, 4 (parvulin) (PIN4) |
| NM_003135.1 | Signal recognition particle 19 kDa protein |
| NM_015933.1 | coiled-coil domain containing 72 (CCDC72) |
| NM_001031.4 | 40S ribosomal protein S28 |
| BC022524.1 | fibroblast growth factor 12 (FGF12) |
| NM_001028.2 | ribosomal protein S25 (RPS25) |
| NM_001997.2 | Finkel-Biskis-Reilly murine sarcoma virus (FBR-MuSV) ubiquitously expressed (FAU) |
| NM_080659.1 | chromosome 11 open reading frame 52 (C11orf52) |

In another embodiment, the substrate and microarrays may contain, as the autoantigen, at least one of the protein antigens of Table 3, or a polypeptide or peptide fragment thereof containing one or more epitopes recognized by the AD diagnostic biomarker, or an epitope peptidomimetic that is recognized by the AD diagnostic biomarker. Peptidomimetics include, for example, D-peptides, peptoids, and β-peptides.

TABLE 3

| Database ID | Description |
|---|---|
| BC051695.1 | FERM domain-containing protein 8 (FRMD8) |
| NM_024754.2 | Pentatricopeptide repeat-containing protein 2 (PTCD2) |
| NM_021104.1 | 60S ribosomal protein L41(RPL41) |
| NM_032855.1 | Hematopoietic SH2 domain-containing protein (HSH2D) |

In another embodiment of one aspect of the present invention, the microarray contains autoantigens consisting of FERM domain-containing protein 8 (FRMD8), 60S ribosomal protein L41(RPL41), pentatricopeptide repeat-containing protein 2 (PTCD2), and hematopoietic SH2 domain-containing protein (HSH2D) or fragments thereof containing one or more epitopes recognized by an AD diagnostic biomarker, or epitope peptidomimetics that are recognized by the AD diagnostic biomarker. Peptidomimetics include, for example, D-peptides, peptoids, and β-peptides. In another embodiment, the microarray contains autoantigens consisting of FERM domain-containing protein 8 (FRMD8) and hematopoietic SH2 domain-containing protein (HSH2D) or fragments thereof containing one or more epitopes recognized by an AD diagnostic biomarker.

In one preferred embodiment of the present invention, the substrate and microarrays may contain, as the autoantigen, at least one of the protein antigens of Table 4, or a fragment thereof containing one or more epitopes recognized by an AD diagnostic biomarker, or an epitope peptidomimetic that is recognized by the AD diagnostic biomarker. Peptidomimetics include, for example, D-peptides, peptoids, and β-peptides. In another preferred embodiment of the present invention, the substrate and microarrays contain all of the protein antigens of Table 4.

TABLE 4

| Database ID | Description |
|---|---|
| BC051695.1 | FERM domain containing 8 (FRMD8) |
| NM_015833.1 | adenosine deaminase, RNA-specific, B1 (RED1 homolog rat) (ADARB1), transcript variant 2 |
| NM_002305.2 | lectin, galactoside-binding, soluble, 1 (galectin 1) (LGALS1) |
| NM_001641.2 | APEX nuclease (multifunctional DNA repair enzyme) 1 (APEX1), transcript variant 1 |
| NM_024316.1 | leukocyte receptor cluster (LRC) member 1 (LENG1) |
| NM_014280.1 | DnaJ homolog subfamily C member 8 |
| PHC1244 | chemokine (C-C motif) ligand 19 (CCL19) |
| BC064984.1 | additional sex combs like 1 (Drosophila) (ASXL1) |
| NM_021104.1 | ribosomal protein L41 (RPL41), transcript variant 1 |
| BC004236.2 | ubiquitin-conjugating enzyme E2S (UBE2S) |
| NM_012387.1 | peptidyl arginine deiminase, type IV (PADI4) |
| NM_003384.1 | vaccinia related kinase 1 (VRK1) |
| NM_004113.3 | fibroblast growth factor 12 (FGF12), transcript variant 2 |
| BC021174.1 | Small EDRK-rich factor 1 |
| NM_001001794.1 | family with sequence similarity 116, member B (FAM116B) |
| NM_032377.2 | elongation factor 1 homolog (S. cerevisiae) (ELOF1) |
| NM_024754.2 | pentatricopeptide repeat domain 2 (PTCD2) |
| NM_000984.2 | ribosomal protein L23a (RPL23A) |
| NM_139016.2 | chromosome 20 open reading frame 198 (C20orf198) |
| NM_024668.1 | ankyrin repeat and KH domain containing 1 (ANKHD1), transcript variant 3 |

In another embodiment of the present invention, the microarrays also contain autoantigens that are reactive with biomarkers diagnostic for Parkinson's Disease (PD) but not for AD, and thus permit differentiation of AD from PD. Autoantigens diagnostic for PD but not AD include, for example, the proteins of Table 5, and fragments thereof containing one or more epitopes recognized by a PD diagnostic biomarker and epitope peptidomimetics that are recognized by the PD diagnostic biomarker. Peptidomimetics include, for example, D-peptides, peptoids, and β-peptides.

TABLE 5

| Database ID | Description |
|---|---|
| NM_003177.3 | Spleen tyrosine kinase (SYK) |
| BC_019015.2 | Mediator of RNA polymerase II transcription subunit 29 (MED29) |
| BC003551 | Protein-glutamine gamma-glutamyltransferase 2 (TGM2) |
| PV3851 | MAP/microtubule affinity-regulating kinase-4 (MAPrk4) |
| BC001755.1 | Leiomodin-1 |

In a further embodiment, the present invention provides a kit for detecting AD-specific antibodies in a sample. A kit comprises one or more autoantigens that are specific for an AD diagnostic biomarker and means for determining binding of the autoantigen to an AD diagnostic biomarker in the sample. The kit may also comprise packaging material comprising a label that indicates that the one or more autoantigens of the kit can be used for the identification of AD. Other components such as buffers, controls, detection reagents, and the like known to those of ordinary skill in art may be included in such the kits. The kits are useful for detecting AD diagnostic biomarkers and for diagnosing AD.

The following examples serve to further illustrate the present invention.

EXAMPLE 1

Materials and Methods

Animals

Swiss-Webster mice were obtained from Taconic Farms (Hudson, N.Y.) and used for experiments at 3-6 months of age. Sprague-Dawley rats were also obtained from Taconic Farms and used at 7-9 weeks of age. Both were maintained on ad libitum food and water with 12-hour light/dark cycle in an AALAC-accredited vivarium. Animals use was reviewed and approved by the UMDNJ IACUC.

Human Brain Tissue

Brain tissue from patients with sporadic AD (n=23, age range=71-88) and age-matched, neurologically normal individuals (n=14, age range=69-83) were obtained from the Harvard Brain Tissue Resource Center (Belmont, Mass.), the Cooperative Human Tissue Network (Philadelphia, Pa.), the UCLA Tissue Resource Center (Los Angeles, Calif.) and Slidomics (Cherry Hill, N.J.). Post-mortem intervals were <24 h and pathological confirmation of AD was evaluated according to criteria defined by the National Institute on Aging and the Reagan Institute Working Group on Diagnostic Criteria for the Neuropathological Assessment of AD (Hyman and Trojanowski (1997) *J Neuropathol Exp Neurol.* 56, 1095-7). Formalin-fixed tissues were processed for routine paraffin embedding and sectioning according to established protocols. Control tissues exhibited minimal localized microscopic AD-like neuropathology.

Antibodies

Aβ42 antibodies were obtained from Millipore International (Temecula, Calif.,) (polyclonal, Cat. No. AB5078P, dilution=1:50) and Pharmingen (San Diego, Calif.) (polyclonal Cat. No. 4767, dilution=1:50). Biotinylated anti-human IgG antibodies for immunohistochemistry were obtained from Vector Laboratories (Burlingame, Calif.) (host: goat, Cat. No. PK-6103, dilution=1:100). Peroxidase-conjugated anti-human IgG antibodies for western blotting were obtained from Thermo Scientific (Rockford, Ill.) (host: goat, Cat. No. 31410, dilution=1:200,000). The following antibodies were used for treatments of mouse organotypic brain slice cultures: anti-alpha7 nicotinic acetylcholine receptor (C-20, Santa Cruz Biotechnology, Santa Cruz, Calif.); anti-GluR2 (polyclonal N19, Santa Cruz Biotechnology, Santa Cruz, Calif.); anti-beta tubulin (D-10, Santa Cruz Biotechnology, Santa Cruz, Calif.). The specificity of these antibodies was confirmed by western blotting.

Human Sera

Human serum samples [AD (n=52, age range=61-97 years); age-matched controls (n=28, age range=51-86); and younger healthy controls (n=28, age range=19-30 years)] were obtained from Analytical Biological Services Inc (Wilmington, Del.). Samples were numerically coded and included the following information: age and sex of the patient, the presence or absence of a detectable neurological disease and, if present, an indication of disease severity and estimated post-mortem interval. Use of these samples was approved by the UMDNJ IRB.

Immunohistochemistry

Immunohistochemistry was carried out using paraffin-embedded brain tissues as previously described (D'Andrea et al. (2001) *Histopathology* 38, 120-34; Nagele et al. (2002) *Neuroscience* 110, 199-211). Briefly, tissues were deparaffinized using xylene and rehydrated through a graded series of decreasing concentrations of ethanol. Antigenicity was enhanced by microwaving sections in citrate buffer. Endogenous peroxidase was quenched by treating sections with 0.3% $H_2O_2$ for 30 min. Sections were incubated in blocking serum and then treated with primary antibodies at appropriate dilutions for 1 hr at room temperature. After a thorough rinse in PBS, biotin-labeled secondary antibody was applied for 30 min. Sections were treated with the avidin-peroxidase complex (Vectastain ABC Elite, Vector Laboratories, Inc., Foster City, Calif.) and visualized with 3-3-diaminobenzidine-4-HCL (DAB)/$H_2O_2$ (Imm-Pact-DAB) (Vector). Sections were then lightly counterstained with hematoxylin, dehydrated through increasing concentrations of ethanol, cleared in xylene and mounted in Permount. Controls consisted of brain sections treated with non-immune serum or omission of the primary antibody. Specimens were examined and photographed with a Nikon FXA microscope, and digital images were recorded using a Nikon DXM1200F digital camera and processed and analyzed using Image Pro Plus (Phase 3 Imaging, Glen Mills, Pa.) and Cell Profiler image analysis softwares.

Preparation of Adult Rat Brain Proteins

To prepare rat brain protein fractions, fresh rat brain tissue was removed from storage at −80° C. and placed in a 1 mM phenylmethylsulfonyl fluoride, 50.0 mM Tris-HCL buffer solution, pH 7.4, at a 10.0 ml/g ratio along with protease inhibitor cocktail (Sigma-Aldrich, St. Louis, Mo.) at a 0.5 ml/g ratio. Using a pre-cooled Dounce homogenizer (Arrow Engineering Co., Inc, Hillside, N.J.) at a setting of four, brain samples were subjected to homogenization. Brain samples were then centrifuged at 3,000 rpm using a Beckman CS-6R centrifuge (Beckman Coulter Inc, Brea, Calif.) equipped with a swing-rotor at 4° C. for a period of 10 min to remove intact cells and large debris. The supernatant was retained as whole brain protein fraction. Protein concentrations were determined using the Bradford Assay.

Detection of Autoantibody Targets Via Western Blotting

Western blot analysis was performed to determine the brain membrane targets of serum auto-antibodies. First, 12.5% SDS-polyacrylamide separating gels were cast using the Mini PROTEAN 3 System (165-3302, BioRad, Hercules, Calif.) and overlain with stacking gels (4.0%). 100.0 µg of protein sample was added to sample buffer and applied to the gel alongside PageRuler™ Prestained Protein Ladder Plus (SM1811, Fermentas, Glen Burnie, Md.). Proteins were then fractionated at 130V for 7 minutes, followed by 100V for the remainder of the resolving time. Proteins were then transferred to Hybond-ECL Nitrocellulose Membrane (RPN3032D, Amersham, Piscataway, N.J.) for 75 minutes at 180 mA. Blots were blocked in 5.0% non-fat dried milk dissolved in PBS-Tween (PBS-T) then transferred to human serum samples (primary antibody), diluted 1:500 in blocking solution, for overnight incubation at 4° C. The following morning, blots were thoroughly rinsed in PBS-T then placed in the appropriately diluted peroxidase-conjugated secondary antibody and incubated for one hour at 4° C. Blots were then thoroughly rinsed in PBS-T then quickly rinsed in $dH_2O$ to remove phosphate buffer. Blots were then developed using the Pierce enhanced chemiluminescence (ECL) substrate (32106, Pierce, Rockford, Ill.) and autoradiography film (XAR ALF 1824, Lab Scientific, Livingston, N.J.). Each western blot for a given serum sample was performed in triplicate.

Mouse Organotypic Brain Slice Cultures and Treatments

Organotypic adult mouse brain slice cultures (MBOCs) were prepared using the technique of Stoppini et al. (1991) *J Neurosci Methods.* 37, 173-82. Neurons in these cultures have been shown to accumulate exogenous Aβ42 (detectable within 4 h of exposure to 100 nM Aβ42) (Bahr et al., (1998) *J Comp Neurol.* 397, 139-47; Harris-White et al., (1998) *J Neurosci.* 18, 10366-74; Malouf, (1992) *Neurobiol Aging.* 13, 543-51; Stoppini et al. (1991)). Brains from Swiss-Webster mice (3-6 months old) were isolated under sterile conditions and transverse coronal slices (0.5-0.75 mm thick) through desired brain regions were prepared using a McIlwain tissue chopper, placed on 30 mm Millicell-CM culture inserts (Millicell-C M, Millipore, Bedford, Mass., USA), and allowed to stabilize in serum-free medium (DMEM) briefly (one hour) or in 25% inactivated horse serum, 25% Hanks' BSS, 50% DMEM, 25 mg/l penicillin-streptomycin) overnight prior to treatment. Following stabilization, cultures were exposed to serum-free medium (DMEM alone) or complete medium (25% inactivated horse serum, 25% Hanks' BSS, 50% DMEM, 25 mg/l penicillin-streptomycin) containing Aβ42 peptide (100 nM), anti-GluR2 antibody (diluted 1:250), human serum samples (diluted 1:50), anti-α7nAChR antibody (diluted 1:1000), anti-β-tubulin antibody (diluted 1:200). Control slices received medium only. MBOCs were treated for up to 72 h at 37° C. in a 5% $CO_2$-enriched atmosphere. Aβ42 was solubilized to the monomeric form using the method of (Zagorski et al. (1999) *Methods Enzymol.* 309, 189-204).

Image Analysis

The extent of Aβ42 accumulation in MBOCs treated with 100 nM Aβ42 with or without human serum or antibodies directed against the α7nAChR or GluR2 was determined using quantitative immunohistochemistry. MBOCs treated as described above were first immunostained with anti-Aβ42 antibodies under identical conditions. Images were then recorded under identical illumination and camera settings using a Nikon FXA microscope equipped with a Nikon CCD camera and image analysis softwares (Image Pro Plus and Cell Profiler). Relative amounts of intracellular Aβ42-positive deposit per Aβ42-positive cell were determined and compared among the different treatment groups. The significance of differences in the amount of intracellular Aβ42 within cells were determined by the Student's t-test. Controls for immunohistochemistry included nonimmune serum or detection antibody only.

EXAMPLE 2

Brain Reactive Autoantibodies in Human Sera

Sera from AD patients (n=52, age range 61-97 years), age-matched, non-demented control subjects (n=28, age range 51-86 years) and younger healthy individuals (n=28, age range 19-30 years) were tested for the presence of brain-reactive autoantibodies. For western analyses, individual sera were tested for the presence of brain-reactive autoantibodies by probing proteins obtained from whole cell homogenate derived from adult rat brain. Results confirmed the presence of brain-reactive autoantibodies in all sera from the three groups tested. The number of immunoreactive protein bands generated by each serum sample was similar for all three subject groups: mean=5.1+/−3.1 for AD sera (n=52); 7.4+/−4.0 for age-matched control sera (n=28); and 6.0+/−3.8 for younger healthy control sera (n=28). Comparable results were obtained when human sera were used to probe mouse and human brain proteins. Based on apparent molecular weights in western blots, a few potentially common protein bands were noted within and among the three subject groups.

EXAMPLE 3

IgG-Positive Neurons in Brain Regions Exhibiting AD Pathology

Ig-positive neurons in postmortem AD brains have been reported (Bouras et al. (2005) *Brain Res Brain Res Rev.* 48, 477-87; Clifford et al. (2007) *Brain Res.* 1142, 223-36; Deane and Zlokovic (2007) *Curr Alzheimer Res.* 4, 191-7; Franceschi et al. (1989) *J Gerontol.* 44, M128-30; Kalaria (1999) *Ann NY Acad Sci.* 893, 113-125; Kulmala et al. (1987) *Exp Aging Res* 13:67-72; Loeffler et al. (1997) *Neurochem Res.* 22, 209-14; Mooradian (1988) *Neurobiol Aging.* 9, 31-9; Nandy et al. (1975) *J Gerontol.* 30, 269-74; Stein et al. (2002) *J Neuropathol Exp Neurol.* 61, 1100-8). In this example, immunohistochemistry using anti-human IgG antibodies was employed to test for the presence of IgG-immunopositive brain components in 23 AD and 14 age-matched control brains. IgG-positive neurons with immunolabeled cell bodies and dendrite trunks were found in all brains that were examined. IgG-positive neurons were far more abundant, widespread and intensely immunostained in AD brains than in corresponding age-matched control brains. In the latter, IgG-positive neurons were most often encountered as scattered individual cells and small cell clusters separated by relatively large expanses of brain tissue that were completely devoid of IgG-positive cells. In AD brains, IgG-positive neurons were particularly abundant in brain regions known to be vulnerable to AD-associated pathological changes (e.g., temporal cortex, entorhinal cortex and hippocampus). In both AD and control brains, IgG immunoreactivity was consistently and preferentially associated with pyramidal neurons, and these cells often showed marked individual variations in the intensity of IgG immunolabeling, sometimes with IgG-positive and -negative neurons present in close proximity. Similar variations in neuronal IgG immunostaining intensity were noted in neurons of the hippocampus. In pyramidal neurons, IgG immunoreactivity was most conspicuous in the cell body and proximal segment of the main dendrite trunk. Most of the smaller neurons, astrocytes and microglia that were interspersed among pyramidal cells were IgG-negative. In three of the 23 AD brains examined, both astrocytes and pyramidal neurons were IgG-positive, but this was not observed in age-matched control brains.

EXAMPLE 4

Relationship Between IgG Immunoreactivity and Aβ42 Deposition

Sections of post-mortem AD brain tissue were probed with antibodies specific for human IgG and Aβ42. In regions of the cerebral cortex and hippocampus showing mild AD pathology (i.e., regions with sequestered intraneuronal Aβ42 deposits but few amyloid plaques), Aβ42-immunopositive neurons also exhibited intense IgG immunostaining. Two sets of consecutive sections were immunostained to reveal the relative distribution of Aβ42 and IgG in the cerebral cortex of AD brains. In regions exhibiting mild AD pathology, both IgG and Aβ42 were colocalized to the same neurons appearing in both sections. Likewise, in cortical regions showing more advanced pathology (as judged by the increased deposition of Aβ42 within neurons and amyloid plaques), the amount of interstitial and intraneuronal IgG was substantially increased. In addition to the typical large juxtanuclear deposits of Aβ42-rich material in pyramidal neurons, the main dendrite trunks of these cells frequently contained abundant small Aβ42-positive granules of uniform size. These results demonstrate the temporal and spatial coincidence of intraneuronal Aβ42 deposition and IgG immunolabeling within pyramidal neurons.

EXAMPLE 5

Reactivity of Human Serum Antibodies with Living Neurons

To test for the reactivity (i.e., binding) of human serum antibodies with the surfaces of living neurons, adult mouse brain organotypic (brain slice) cultures (MBOCs) were maintained in medium with or without diluted human serum for up to 72 h. MBOCs retain the adult brain histological architecture for up to several weeks under proper conditions and have been shown to contain neurons that internalize and accumulate exogenous, soluble Aβ42 peptide (Bahr et al. (1998); Harris-White et al. (1998); Malouf (1992); Stoppini et al. (1991). The binding of human IgG to neurons in MBOCs was detected by immunohistochemistry using anti-human IgG antibodies. Addition of human serum to the culture medium resulted in intense and selective IgG immunolabeling of living adult mouse neurons, whereas controls not treated with serum showed no inherent IgG immunoreactivity. The pattern of background IgG immunostaining in human serum-treated MBOCs suggests that dendrites and/or synaptic connections may also be IgG-positive. As was shown in postmortem human AD brains described above, pyramidal neurons of the cerebral cortex of MBOCs were consistently the most intensely immunopositive cells.

EXAMPLE 6

Effect of Autoantibodies on Internalization of Exogenous Aβ42

This example utilizes the property of cross-reactivity of the antibodies in human serum with rodent brain proteins as demonstrated above in western blots and in brain tissue as shown above in immunohistochemical preparations. MBOCs were treated with 100 nM Aβ42 in the presence or absence of individual human serum samples diluted 1:50 in otherwise serum-free medium for 1, 3, 24, 48 and 72 h and the relative amounts of intraneuronal Aβ42 were quantified using image analysis for MBOCs treated for 24 h. MBOCs treated with 100 nM Aβ42 alone for 24 h showed no human IgG immunostaining and only minimal Aβ42 immunoreactivity. On the other hand, when MBOCs were exposed to human serum autoantibodies and Aβ42 peptide for 24 h, pyramidal neurons selectively showed a dramatic increase in intracellular Aβ42 accumulation over that of controls treated with Aβ42 peptide or serum alone for the same time period. Within these neurons, Aβ42-positive material was localized to dense cytoplasmic granules that were concentrated in the neuronal perikaryon and proximal dendrite trunk. Measurements of the relative amounts of intraneuronal Aβ42 in MBOCs using image analysis after 24 h of treatment revealed that the addition of human serum to medium containing 100 nM Aβ42 caused a many-fold increase in neuronal Aβ42 immunoreactivity over that in cells treated with Aβ42 alone. Morphological evidence of significant cell death and loss of Aβ42-burdened neurons in MBOCs was not observed

EXAMPLE 7

Effect of Purified Antibodies Targeting Neural Surface Proteins on Internalization of Exogenous Aβ42

MBOCs were treated for 24 h with commercially available antibodies directed against two neuronal receptors that are known to be abundantly expressed on neuronal cell surfaces, the alpha7 nicotinic acetylcholine receptor (α7nAChR) and the glutamate R2 (GluR2) receptor. Both antibodies were found to be effective in increasing intraneuronal Aβ42 accumulation, again selectively in pyramidal neurons and well above levels seen in cultures treated with Aβ42 alone. To explore whether neuronal cell surface reactivity of IgG is required for enhancement of exogenous Aβ42 internalization, MBOCs were also treated with an antibody directed against the common intracellular protein, beta-tubulin, along with 100 nM Aβ42. Treatment with beta-tubulin antibody resulted in levels of neuronal Aβ42 accumulation that were comparable to treatment with 100 nM Aβ42 alone.

EXAMPLE 8

Identification of Biomarkers Diagnostic for AD

Western Analysis

As disclosed hereinabove, biochemical confirmation of the presence of brain-reactive autoantibodies in individual human sera was carried out using western analysis. In addition, total rat brain protein, which is immunoreactive to human autoantibodies as shown hereinabove, was used to compare sera from patients with AD, age-matched neurologically normal controls and younger healthy individuals. Based on estimated molecular weights alone, the resulting distributions of molecular weights for individual target proteins were analyzed using the pattern recognition computer program called A.I. Solver (Silversoft Solutions).

Based on the recognition of specific patterns of distribution of molecular weights of autoantibody target proteins, A.I. Solver was able to distinguish western blots derived from AD patient's sera from that of age-matched controls and younger healthy subjects 98% of the time. This example demonstrates the existence of AD-specific protein antibodies in the blood that bind to brain protein target antigens. Next, a protein microarray platform was used identify the specific subset of autoantibodies and their target proteins that are useful to effectively diagnose AD.

Microarray Procedure

The protein microarray platform used to identify diagnostic antibodies and prove the efficacy of a protein microarray diagnostic was Invitrogen's ProtoArray® Human Protein Microarray v5.0. It is a high-density protein microarray containing thousands of purified human proteins for protein interaction screening. Each human open reading frame (ORF) is expressed as an N-terminal GST fusion protein using a baculovirus expression system, purified from insect cells, and printed in duplicate on a nitrocellulose-coated glass slide. The Immune Response Biomarker Profiling application was used as it is best suited the needs of a diagnostic. All reagents and materials were purchased directly through Invitrogen. The recommended Invitrogen ProtoArray® protocol was strictly adhered to at all times and is incorporated herein by reference in its entirety. The array was probed with diluted (1:500) human serum or plasma.

Microarray Scanning

The protein microarrays were scanned using the recommended Axon Genepix 4000b imager. Individual slides were inserted into the imager and then scanned using 100% laser power, 635 nm excitation wavelength, PMT 600, and Sum pixel size. Data was extracted from the image by syncing it with a Genepix Array List (.GAL) file obtained from Invitrogen. GAL files describe the location and identity of all spots on the protein microarray and are used by Genepix Pro software (by Molecular Devices) to generate files that contain pixel intensity information for all features on the array. Genepix Pro then creates a .GPR (Genepix Pixel Results) file that lists all of the pixel intensity data for each protein spot on the microarray in text-only spreadsheet format. It is the GPR file that is imported into Prospector for data analysis.

Normalization

After acquiring the individual microarray data by scanning the microarrays with an Axon Genepix 4000b imager and performing the initial quantification with Genepix Pro software, the resulting data were normalized so as to allow microarray-to-microarray comparison. For this, Invitrogen's proprietary software, Prospector; more specifically, the Immune Response Biomarker Profiling Toolbox application, was used. Each microarray's gpr file was imported into the program, analyzed, and normalized to a linear model.

Fitting the data to a linear model was performed through a robust regression by means of an iteratively re-weighted least-square procedure with an M-estimator, like the median. The linear model uses log-transformed signals to estimate and correct the variations. For each spot replicate r (=1,2) of protein feature k 1, ..., $n_f$) in sub-array j (=1, ..., 48) on slide i (1, ..., $n_s$,) the following model was fit:

$$y_{ijkr} = \alpha_i + \beta_j + \tau_k \varepsilon_{ijkr}$$

where $y_{ijkr}$ is the observed signal in log 2 scale, $\alpha$ is the slide effect, $\beta_j$ is the sub-array/block effect (including printing pin effect), $\tau_k$ is the "true" signal of the protein feature (different protein content printed in different concentration), and $\varepsilon_{ijkr}$ is the error, assuming $\varepsilon_{ijkr} \sim N(0,\sigma^2)$. After the coefficients of these effects were estimated using control proteins, the normalized signal in its original scale for each spot was calculated as:

$$S_{ijkr} = 2^{(y_{ijkr} - \alpha_i - \beta_j)}$$

After normalization, the microarray data was fully adjusted for error and individual variation; formal analysis was begun. It was this adjusted data from which diagnostic significance was determined.

Data Analysis

There are multiple accepted methods of determining the diagnostic significance of microarray fluorescence data. To ensure the reproducibility and accuracy of our results, data were analyzed three separate times using three independent and distinct methods. The methods chosen are among the most reliable and consistent available, and are commonly used in similar studies. The methods are: M-Statistical Prevalence, Nearest Shrunken Centroid Analysis, and Random Forest Decision-Making Trees. To harness each of these unbiased statistical quantification schemes, Prospector, PAM, and R's Random Forest, respectively, were utilized. Each of these programs evaluated the protein microarray data to determine which proteins were most significant to diagnose Alzheimer's Disease. The lists reflected one another almost exactly, thus demonstrating that protein microarrays are useful as a successful diagnostic. The statistical methods, programs involved, and results generated are described below.

M-Statistical Analysis

As well as interpreting and normalizing the raw fluorescence data generated by Genepix Pro, Prospector was used to generate M-Statistics that were, in turn, used to evaluate each protein's diagnostic significance. Briefly, M-statistics were used to determine the number of assays in one group (e.g. Alzheimer's or Control) that have a signal value for a protein greater than the highest observed signal value of this probe in the comparison group. The M order statistic for the group y of size $n_y$ compared to group x of size $n_x$ is given by the formula:

$$M^i{}_{i,above,between} = \Sigma 1_{\{yk > x(i) + between\}} 1_{\{yk > above\}}$$

where $x_{(i)}$ is the $i_{th}$ largest value of the group x, and above and between are the calculation parameters. A p-value was calculated as the probability of having M value greater or equal than $M_i$. Prospector selected the M statistic with the lowest p-value and reported this $M_{max}$ value and order, as well as a corresponding p-value and protein prevalence estimate. The values were viewed as a spreadsheet in Microsoft Excel Workbook format, and filtered to provide a list of the most effective indicators of group differences, i.e., the proteins that are the best diagnostic markers.

PAM (Prediction Analysis of Microarrays)

Another method of interpreting protein microarray results and yielding protein significance is PAM, or Prediction Analysis of Microarrays. PAM is a statistical technique for class prediction that uses nearest shrunken centroids. It is run as a Microsoft Excel Macro and has been used extensively in characterizing microarray results (Tibshirani et al. (2002) *Proc Natl Acad Sci USA* 99:6567-6572). The program was used to identify specific subsets of fluorescence data that best characterize each class and thus serve as significant diagnostic indicators. Briefly, the method computed a standardized centroid for each class. This is the average fluorescence for protein in each class divided by the within-class standard deviation for that protein. Centroids were "shrunken"—reduced by a threshold value—to reduce error and outlier effect. The microarray fluorescence of each new sample was then compared to each shrunken class centroid; the class whose centroid that it was closest to, in squared distance, was the predicted class for that new sample. Using this information, PAM generated a list of proteins presented in order of diagnostic significance.

PAM was used to produce a list of the top fifty most important proteins for distinguishing Alzheimer's Disease sera from Control Sera which is shown below in Table 6.

TABLE 6

| Protein database ID | Description | AD score | Control score |
|---|---|---|---|
| BC030984.1 | cDNA clone MGC: 32654 IMAGE: 4701898, complete cds | 0.2132 | −0.2665 |
| PHR5001 | Recombinant human CTLA-4/Fc | 0.2108 | −0.2635 |
| BC016380.1 | cDNA clone MGC: 27376 IMAGE: 4688477, complete cds | 0.1766 | −0.2208 |

TABLE 6-continued

| Protein database ID | Description | AD score | Control score |
|---|---|---|---|
| BC015833.1 | cDNA clone MGC: 27152 IMAGE: 4691630, complete cds | 0.1621 | −0.2026 |
| BC099907.1 | General transcription factor II-I | −0.156 | 0.195 |
| BC051695.1 | FERM domain containing 8 (FRMD8) | 0.1452 | −0.1816 |
| BC040106.1 | hypothetical protein HSPC111 (HSPC111) | 0.1429 | −0.1787 |
| NM_003141.2 | tripartite motif-containing 21 (TRIM21) | 0.1388 | −0.1735 |
| NM_003384.1 | vaccinia related kinase 1 (VRK1) | 0.1268 | −0.1585 |
| BC004236.2 | ubiquitin-conjugating enzyme E2S (UBE2S) | 0.1244 | −0.1555 |
| BC001662.1 | MAP kinase-activated protein kinase 3 | 0.1183 | −0.1479 |
| NM_017588.1 | WD repeat domain 5 (WDR5), transcript variant 1 | 0.1176 | −0.147 |
| NM_032377.2 | elongation factor 1 homolog (S. cerevisiae) (ELOF1) | 0.1158 | −0.1448 |
| NM_021032.2 | fibroblast growth factor 12 (FGF12), transcript variant 1 | 0.1144 | −0.143 |
| NM_000984.2 | ribosomal protein L23a (RPL23A) | 0.1123 | −0.1403 |
| BC064984.1 | additional sex combs like 1 (Drosophila) (ASXL1) | 0.1106 | −0.1383 |
| NM_012387.1 | peptidyl arginine deiminase, type IV (PADI4) | 0.1082 | −0.1353 |
| NM_001641.2 | APEX nuclease (multifunctional DNA repair enzyme) 1 (APEX1), transcript variant 1 | 0.1062 | −0.1327 |
| NM_001896.2 | casein kinase 2, alpha prime polypeptide (CSNK2A2) | 0.1045 | −0.1306 |
| NM_014481.2 | APEX nuclease (apurinic/apyrimidinic endonuclease) 2 (APEX2), nuclear gene encoding mitochondrial protein | −0.1009 | 0.1261 |
| NM_014280.1 | DnaJ homolog subfamily C member 8 | 0.0993 | −0.1242 |
| BC007228.1 | CSAG family, member 3A (CSAG3A) | 0.0952 | −0.119 |
| BC021174.1 | Small EDRK-rich factor 1 | 0.0924 | −0.1155 |
| BC021174.1 | Small EDRK-rich factor 1 | 0.0924 | −0.1155 |
| BC033758.1 | centaurin, alpha 2 (CENTA2) | 0.0894 | −0.1118 |
| BC005248.1 | eukaryotic translation initiation factor 1A, Y-linked (EIF1AY) | 0.0876 | −0.1096 |
| BC022098.1 | cDNA clone MGC: 31944 IMAGE: 4878869, complete cds | 0.0853 | −0.1066 |
| NM_024754.2 | pentatricopeptide repeat domain 2 (PTCD2) | 0.0845 | −0.1057 |
| NM_024316.1 | leukocyte receptor cluster (LRC) member 1 (LENG1) | −0.0836 | 0.1044 |
| NM_015920.3 | 40S ribosomal protein S27-like protein | 0.0798 | −0.0997 |
| BC048970.1 | tubulin tyrosine ligase-like family, member 7 (TTLL7) | 0.0792 | −0.099 |
| NM_003668.2 | mitogen-activated protein kinase-activated protein kinase 5 (MAPKAPK5), transcript variant 1 | 0.0789 | −0.0986 |
| NM_007278.1 | GABA(A) receptor-associated protein (GABARAP) | 0.0787 | −0.0984 |
| NM_006838.1 | methionyl aminopeptidase 2 (METAP2) | 0.0779 | −0.0974 |
| NM_018439.1 | Impact homolog (mouse) (IMPACT) | 0.0772 | −0.0965 |
| NM_002013.2 | FK506 binding protein 3, 25 kDa (FKBP3) | 0.0749 | −0.0937 |
| NM_018956.2 | chromosome 9 open reading frame 9 (C9orf9) | 0.0744 | −0.093 |
| NM_004987.3 | LIM and senescent cell antigen-like-containing domain protein 1 | −0.0741 | 0.0926 |
| BC004292.1 | PHD finger protein 15 (PHF15) | −0.0709 | 0.0886 |
| NM_133494.1 | NIMA (never in mitosis gene a)- related kinase 7 (NEK7) | 0.0699 | −0.0874 |
| NM_145063.1 | chromosome 6 open reading frame 130 (C6orf130) | 0.0646 | −0.0808 |
| NM_021104.1 | ribosomal protein L41 (RPL41), transcript variant 1 | 0.0645 | −0.0807 |
| NM_006223.1 | protein (peptidylprolyl cis/trans isomerase) NIMA-interacting, 4 (parvulin) (PIN4) | 0.0633 | −0.0791 |
| NM_003135.1 | Signal recognition particle 19 kDa protein | 0.0622 | −0.0777 |
| NM_015933.1 | coiled-coil domain containing 72 (CCDC72) | 0.0615 | −0.0769 |
| NM_001031.4 | 40S ribosomal protein S28 | 0.0606 | −0.0758 |
| BC022524.1 | fibroblast growth factor 12 (FGF12) | 0.0594 | −0.0743 |
| NM_001028.2 | ribosomal protein S25 (RPS25) | 0.0578 | −0.0722 |
| NM_001997.2 | Finkel-Biskis-Reilly murine sarcoma virus (FBR-MuSV) ubiquitously expressed (FAU) | 0.0572 | −0.0715 |
| NM_080659.1 | chromosome 11 open reading frame 52 (C11orf52) | 0.0566 | −0.0707 |

Random Forest

The third quantitative method that was used to corroborate the results was Random Forest. This is an open-source classification algorithm, run through R, that uses an ensemble of decision-making trees. Each of these classification trees was built using a bootstrap sample of the data, and at each split the candidate set of variables was a random subset. Random Forest directly returned several measures of variable significance, which were related to the relevance of the variable in the classification. Hence, in this case, it provided an evaluation of each protein's relative importance to proper diagnosis.

The most reliable measure was based on the decrease of classification accuracy when values of a variable in a node of a tree were permuted randomly and this was the measure of variable importance. Another estimation of significance of a variable was based on Gini impurity. Every time a split of a node was made on variable m the Gini impurity criterion for the two descendent nodes was less than the parent node. Adding up the Gini decreases for each individual variable over all trees in the forest gave a fast variable importance that is often very consistent with the permutation importance measure.

The Relative Fluorescence Unit value for each protein spot on the microarray, as calculated by Genepix Pro and Prospector, was imported into Random Forest. The prediction model was performed using the R package and all default settings—as is proscribed for the best microarray analysis results. Calculating an average Out-Of-Bag Error of only 6.67%, the algorithm was able to quickly evaluate protein significance based on the evaluation methods described above.

Results

Three different, unbiased statistical methods were used to evaluate the diagnostic significance of individual autoantibodies in the microarray data and they reflected one another almost perfectly. The three resultant lists considered the same autoantibodies diagnostically important, and assigned them similar significance. The shared conclusions of all three lend the results great confidence. The list of all of the protein antigens determined by these methods that have autoantibodies that can be used as indicators for Alzheimer's disease is shown below in Table 7. Included is the protein database identification number, the open reading frame number, the common name for each protein, its disease-state indication, and the relevant p-value as calculated by the M-statistic.

TABLE 7

| Database ID | Ultimate ORF ID | Description | Indication | P-Value |
|---|---|---|---|---|
| NM_024754.2 | IOH12500 | pentatricopeptide repeat domain 2 (PTCD2) | AD | 8.03E−14 |
| BC051695.1 | IOH26532 | FERM domain containing 8 (FRMD8) | AD | 4.06E−13 |
| NM_014280.1 | IOH42939 | DnaJ homolog subfamily C member 8 | AD | 9.49E−12 |
| BC064984.1 | IOH40665 | additional sex combs like 1 (*Drosophila*) (ASXL1) | AD | 6.02E−11 |
| BC030814.1 | IOH23035 | immunoglobulin kappa variable 1-5 (IGKV1-5) | Control | 7.00E−11 |
| NM_003384.1 | IOH41408 | vaccinia related kinase 1 (VRK1) | AD | 2.03E−10 |
| NM_001544.2 | IOH23172 | intercellular adhesion molecule 4 (Landsteiner-Wiener blood group) (ICAM4), transcript variant 1 | AD | 2.03E−10 |
| NM_001896.2 | IOH6369 | casein kinase 2, alpha prime polypeptide (CSNK2A2) | AD | 2.51E−10 |
| NM_021104.1 | IOH13630 | ribosomal protein L41 (RPL41), transcript variant 1 | AD | 4.61E−10 |
| BC016380.1 | IOH23077 | cDNA clone MGC: 27376 IMAGE: 4688477, complete cds | AD | 5.14E−10 |
| NM_012387.1 | IOH11317 | peptidyl arginine deiminase, type IV (PADI4) | AD | 6.53E−10 |
| NM_003135.1 | IOH59899 | Signal recognition particle 19 kDa protein | AD | 8.77E−10 |
| BC022524.1 | IOH10757 | fibroblast growth factor 12 (FGF12) | AD | 8.77E−10 |
| BC000758.1 | IOH3735 | Coiled-coil domain-containing protein 28A | AD | 1.45E−09 |
| NM_021032.2 | IOH35339 | fibroblast growth factor 12 (FGF12), transcript variant 1 | AD | 1.45E−09 |
| NM_022343.2 | IOH59950 | Golgi-associated plant pathogenesis-related protein 1 | AD | 1.49E−09 |
| BC004236.2 | IOH3887 | ubiquitin-conjugating enzyme E2S (UBE2S) | AD | 2.00E−09 |
| NM_000983.3 | IOH58958 | 60S ribosomal protein L22 | AD | 2.05E−09 |
| NM_017588.1 | IOH4895 | WD repeat domain 5 (WDR5), transcript variant 1 | AD | 2.88E−09 |
| NM_018956.2 | IOH11209 | chromosome 9 open reading frame 9 (C9orf9) | AD | 3.30E−09 |
| BC033178.1 | IOH23236 | immunoglobulin heavy constant gamma 3 (G3m marker) (IGHG3) | AD | 4.07E−09 |
| NM_006628.4 | IOH3044 | cyclic AMP phosphoprotein, 19 kD (ARPP-19) | AD | 4.19E−09 |
| BC022098.1 | IOH14790 | cDNA clone MGC: 31944 IMAGE: 4878869, complete cds | AD | 4.19E−09 |
| NM_001641.2 | IOH5081 | APEX nuclease (multifunctional DNA repair enzyme) 1 (APEX1), transcript variant 1 | AD | 5.85E−09 |
| NM_003668.2 | | mitogen-activated protein kinase-activated protein kinase 5 (MAPKAPK5), transcript variant 1 | AD | 8.91E−09 |
| NM_015933.1 | IOH3769 | coiled-coil domain containing 72 (CCDC72) | AD | 8.91E−09 |
| PHC1244 | | chemokine (C-C motif) ligand 19 (CCL19) | AD | 9.85E−09 |
| BC099907.1 | IOH62625 | General transcription factor II-I | Control | 1.09E−08 |
| BC007782.2 | IOH6514 | immunoglobulin lambda constant 1 (Mcg marker) (IGLC1) | AD | 1.09E−08 |

TABLE 7-continued

| Database ID | Ultimate ORF ID | Description | Indication | P-Value |
|---|---|---|---|---|
| BC006423.1 | | Serine/threonine-protein kinase 6 | AD | 1.34E−08 |
| BC042628.1 | IOH27650 | serpin peptidase inhibitor, clade E (nexin, plasminogen activator inhibitor type 1), member 2 (SERPINE2) | AD | 1.34E−08 |
| BC021561.1 | IOH14131 | FACT complex subunit SPT16 | AD | 1.34E−08 |
| BC005248.1 | IOH7358 | eukaryotic translation initiation factor 1A, Y-linked (EIF1AY) | AD | 1.34E−08 |
| NM_006223.1 | IOH7192 | protein (peptidylprolyl cis/trans isomerase) NIMA-interacting, 4 (parvulin) (PIN4) | AD | 1.34E−08 |
| NM_032377.2 | IOH6191 | elongation factor 1 homolog (*S. cerevisiae*) (ELOF1) | AD | 1.34E−08 |
| BC057774.1 | IOH29168 | RNA (guanine-9-)-methyltransferase domain-containing protein 3 | AD | 1.52E−08 |
| NM_004196.2 | | Cyclin-dependent kinase-like 1 | AD | 1.64E−08 |
| BC001662.1 | | MAP kinase-activated protein kinase 3 | AD | 2.32E−08 |
| NM_015920.3 | IOH57353 | 40S ribosomal protein S27-like protein | AD | 2.32E−08 |
| NM_001031.4 | IOH58930 | 40S ribosomal protein S28 | AD | 2.62E−08 |
| NM_003688.1 | | Peripheral plasma membrane protein CASK | AD | 2.62E−08 |
| BC048970.1 | IOH26893 | tubulin tyrosine ligase-like family, member 7 (TTLL7) | AD | 3.23E−08 |
| NM_000984.2 | IOH13591 | ribosomal protein L23a (RPL23A) | AD | 3.23E−08 |
| NM_018439.1 | IOH23069 | Impact homolog (mouse) (IMPACT) | AD | 3.76E−08 |
| NM_002305.2 | IOH3861 | lectin, galactoside-binding, soluble, 1 (galectin 1) (LGALS1) | AD | 3.76E−08 |
| BC056508.1 | IOH29456 | variable charge, Y-linked 1B (VCY) | AD | 4.13E−08 |
| BC090938.1 | IOH62696 | Ig gamma-1 chain C region | AD | 4.45E−08 |
| NM_002013.2 | IOH14109 | FK506 binding protein 3, 25 kDa (FKBP3) | AD | 4.51E−08 |
| NM_007278.1 | IOH41289 | GABA(A) receptor-associated protein (GABARAP) | AD | 4.51E−08 |
| BC007228.1 | IOH6059 | CSAG family, member 3A (CSAG3A) | AD | 4.51E−08 |
| BC033758.1 | IOH21879 | centaurin, alpha 2 (CENTA2) | AD | 5.27E−08 |
| BC092518.1 | IOH62695 | Ig gamma-1 chain C region | AD | 6.86E−08 |
| BC019598.1 | IOH10613 | Zinc finger matrin-type protein 4 | AD | 7.00E−08 |
| NM_145909.1 | IOH45888 | Zinc finger protein 323 | AD | 7.00E−08 |
| NM_003516.2 | IOH4867 | histone cluster 2, H2aa3 (HIST2H2AA3) | AD | 7.22E−08 |
| NM_006838.1 | IOH11106 | methionyl aminopeptidase 2 (METAP2) | AD | 7.36E−08 |
| BC026038.1 | IOH13982 | Ig gamma-1 chain C region | AD | 1.01E−07 |
| NM_002129.2 | IOH3826 | high-mobility group box 2 (HMGB2) | AD | 1.01E−07 |
| NM_002677.1 | IOH27101 | peripheral myelin protein 2 (PMP2) | AD | 1.16E−07 |
| BC001132.1 | IOH3853 | DEAD (Asp-Glu-Ala-Asp) box polypeptide 54 (DDX54) | AD | 1.27E−07 |
| NM_001001794.1 | IOH27259 | family with sequence similarity 116, member B (FAM116B) | AD | 1.27E−07 |
| NM_001997.2 | IOH1655 | Finkel-Biskis-Reilly murine sarcoma virus (FBR-MuSV) ubiquitously expressed (FAU) | AD | 1.27E−07 |
| BC021174.1 | IOH10706 | Small EDRK-rich factor 1 | AD | 1.27E−07 |
| NM_001028.2 | IOH5471 | ribosomal protein S25 (RPS25) | AD | 1.27E−07 |
| NM_003512.3 | IOH14485 | Histone H2A type 1-C | AD | 1.78E−07 |
| NM_002095.1 | IOH22963 | general transcription factor IIE, polypeptide 2, beta 34 kDa (GTF2E2) | AD | 1.97E−07 |
| NM_005720.1 | IOH3992 | actin related protein 2/3 complex, subunit 1B, 41 kDa (ARPC1B) | AD | 1.97E−07 |
| NM_003868.1 | IOH42157 | fibroblast growth factor 16 (FGF16) | AD | 1.97E−07 |
| NM_004214.3 | IOH2103 | fibroblast growth factor (acidic) intracellular binding protein (FIBP), transcript variant 2 | AD | 1.97E−07 |
| NM_021079.2 | IOH14141 | N-myristoyltransferase 1 (NMT1) | AD | 1.99E−07 |
| NM_015833.1 | IOH38242 | adenosine deaminase, RNA-specific, B1 (RED1 homolog rat) (ADARB1), transcript variant 2 | AD | 2.62E−07 |
| PHR5001 | | Recombinant human CTLA-4/Fc | AD | 2.62E−07 |

TABLE 7-continued

| Database ID | Ultimate ORF ID | Description | Indication | P-Value |
|---|---|---|---|---|
| BC030983.1 | IOH23183 | immunoglobulin lambda locus (IGL@) | AD | 2.62E−07 |
| BC030984.1 | IOH23182 | cDNA clone MGC: 32654 IMAGE: 4701898, complete cds | AD | 2.62E−07 |
| BC002733.2 | IOH5365 | chromosome 1 open reading frame 77 (C1orf77) | Control | 2.62E−07 |
| NM_133494.1 | IOH45126 | NIMA (never in mitosis gene a)-related kinase 7 (NEK7) | AD | 2.65E−07 |
| BC010467.1 | IOH11119 | cDNA clone MGC: 17410 IMAGE: 4156035, complete cds | AD | 3.42E−07 |
| NM_014060.1 | IOH4208 | malignant T cell amplified sequence 1 (MCTS1) | AD | 3.42E−07 |
| NM_016167.3 | IOH40609 | nucleolar protein 7, 27 kDa (NOL7) | AD | 3.81E−07 |
| BC015833.1 | IOH14840 | cDNA clone MGC: 27152 IMAGE: 4691630, complete cds | AD | 4.30E−07 |
| NM_145063.1 | IOH13839 | chromosome 6 open reading frame 130 (C6orf130) | AD | 5.08E−07 |
| BC040106.1 | IOH26285 | hypothetical protein HSPC111 (HSPC111) | AD | 5.08E−07 |
| BC010947.1 | IOH14455 | signal recognition particle 19 kDa (SRP19) | AD | 5.08E−07 |
| NM_014065.2 | IOH43942 | Protein asteroid homolog 1 | AD | 5.31E−07 |
| BC012760.2 | IOH62834 | Glycogen synthase kinase-3 beta | AD | 5.38E−07 |
| NM_004088.1 | IOH11297 | deoxynucleotidyltransferase, terminal (DNTT), transcript variant 1 | AD | 6.41E−07 |
| BC019337.1 | IOH12297 | immunoglobulin heavy constant gamma 1 (G1m marker) (IGHG1) | AD | 7.15E−07 |
| NM_024316.1 | IOH12150 | leukocyte receptor cluster (LRC) member 1 (LENG1) | Control | 7.80E−07 |
| NM_002938.2 | IOH41414 | ring finger protein 4 (RNF4) | AD | 7.80E−07 |
| NM_006620.2 | IOH4029 | HBS1-like (*S. cerevisiae*) (HBS1L) | AD | 8.79E−07 |
| NM_000992.2 | IOH1702 | 60S ribosomal protein L29 | AD | 1.05E−06 |
| NM_024668.2 | IOH46162 | ankyrin repeat and KH domain containing 1 (ANKHD1), transcript variant 3 | AD | 1.05E−06 |
| NM_031445.1 | IOH5185 | AMME chromosomal region gene 1-like (AMMECR1L) | AD | 1.26E−06 |
| NM_003517.2 | IOH29296 | histone cluster 2, H2ac (HIST2H2AC) | AD | 1.38E−06 |
| BC072419.1 | IOH62555 | Ig gamma-1 chain C region | AD | 1.50E−06 |
| NM_145174.1 | IOH44767 | DnaJ (Hsp40) homolog, subfamily B, member 7 (DNAJB7) | AD | 1.57E−06 |
| BC022361.1 | IOH14170 | rRNA-processing protein FCF1 homolog | AD | 1.57E−06 |
| BC006376.1 | IOH6481 | N-myristoyltransferase 2 (NMT2) | AD | 1.60E−06 |
| NM_001895.1 | | casein kinase 2, alpha 1 polypeptide (CSNK2A1), transcript variant 2 | AD | 1.60E−06 |
| NM_003524.2 | IOH58715 | Histone H2B type 1-H | AD | 1.69E−06 |
| BC027951.1 | IOH11889 | Cas scaffolding protein family member 4 | AD | 1.93E−06 |
| NM_134427.1 | IOH45474 | regulator of G-protein signaling 3 (RGS3), transcript variant 4 | AD | 2.02E−06 |
| NM_052969.1 | IOH12514 | ribosomal protein L39-like (RPL39L) | AD | 2.02E−06 |
| NM_023080.1 | IOH13369 | chromosome 8 open reading frame 33 (C8orf33) | AD | 2.17E−06 |
| NM_138779.1 | IOH10711 | chromosome 13 open reading frame 27 (C13orf27) | AD | 2.17E−06 |
| BC026030.1 | IOH14611 | zinc finger protein 239 (ZNF239) | AD | 2.32E−06 |
| BC029760.1 | IOH22119 | OTU domain containing 6B (OTUD6B) | AD | 2.76E−06 |
| PHC1475 | | C-C motif chemokine 21 | AD | 3.00E−06 |
| NM_133336.1 | IOH42549 | Wolf-Hirschhorn syndrome candidate 1 (WHSC1), transcript variant 9 | AD | 3.44E−06 |
| BC034142.1 | IOH23177 | immunoglobulin kappa variable 1-5 (IGKV1-5) | AD | 3.67E−06 |
| NM_020235.2 | IOH44025 | bobby sox homolog (*Drosophila*) (BBX) | AD | 3.67E−06 |
| NM_198829.1 | IOH58974 | Ras-related C3 *botulinum* toxin substrate 1 | AD | 3.89E−06 |
| BC098112.1 | IOH63324 | Histone H2B type 1-N | AD | 3.89E−06 |
| NM_032359.1 | IOH5762 | chromosome 3 open reading frame 26 (C3orf26) | AD | 4.32E−06 |

TABLE 7-continued

| Database ID | Ultimate ORF ID | Description | Indication | P-Value |
|---|---|---|---|---|
| NM_001966.2 | IOH62346 | Peroxisomal bifunctional enzyme | AD | 4.32E−06 |
| BC032451.1 | IOH21663 | cDNA clone MGC: 40426 IMAGE: 5178085, complete cds | AD | 4.76E−06 |
| XM_379117.1 | IOH43619 | PREDICTED: Homo sapiens hypothetical protein LOC150568 (LOC150568) | AD | 4.98E−06 |
| BC033159.1 | IOH23223 | DnaJ (Hsp40) homolog, subfamily C, member 8 (DNAJC8) | AD | 4.98E−06 |
| NM_006756.2 | IOH42106 | transcription elongation factor A (SII), 1 (TCEA1), transcript variant 1 | AD | 4.98E−06 |
| NM_016940.1 | IOH12821 | RWD domain containing 2B (RWDD2B) | AD | 5.00E−06 |
| NM_177559.2 | IOH13704 | casein kinase 2, alpha 1 polypeptide (CSNK2A1), transcript variant 1 | AD | 5.00E−06 |
| NM_004178.3 | IOH45867 | TAR (HIV-1) RNA binding protein 2 (TARBP2), transcript variant 3 | AD | 5.13E−06 |
| NM_032338.2 | IOH7537 | chromosome 12 open reading frame 31 (C12orf31) | AD | 5.22E−06 |
| BC005955.1 | IOH7485 | chromosome 8 open reading frame 53 (C8orf53) | AD | 5.50E−06 |
| NM_001009613.1 | IOH58584 | Sperm protein associated with the nucleus on the X chromosome N4 | AD | 5.50E−06 |
| BC036723.1 | IOH22599 | Fc fragment of IgG, low affinity IIIa, receptor (CD16a) (FCGR3A) | AD | 5.50E−06 |
| NM_003690.3 | IOH57108 | Interferon-inducible double stranded RNA-dependent protein kinase activator A | AD | 6.84E−06 |
| NM_014473.2 | IOH9851 | DIM1 dimethyladenosine transferase 1-like (S. cerevisiae) (DIMT1L) | AD | 6.91E−06 |
| NM_032855.1 | IOH14623 | hematopoietic SH2 domain containing (HSH2D) | AD | 7.69E−06 |
| NM_001167.2 | IOH21984 | baculoviral IAP repeat-containing 4 (BIRC4) | AD | 7.69E−06 |
| NM_178571.2 | IOH26524 | hypothetical protein MGC51025 (MGC51025) | AD | 7.69E−06 |
| NM_003600.1 | | aurora kinase A (AURKA), transcript variant 2 | AD | 7.69E−06 |
| NM_006912.3 | IOH29584 | Ras-like without CAAX 1 (RIT1) | AD | 8.05E−06 |
| NM_005307.1 | | G protein-coupled receptor kinase 4 | AD | 8.29E−06 |
| BC001280.1 | IOH21165 | Serine/threonine-protein kinase 6 | AD | 8.71E−06 |
| NM_182970.2 | IOH43687 | regulating synaptic membrane exocytosis 4 (RIMS4) | AD | 8.71E−06 |
| NM_153332.2 | IOH27323 | three prime histone mRNA exonuclease 1 (THEX1) | AD | 8.71E−06 |
| NM_139016.2 | IOH27635 | chromosome 20 open reading frame 198 (C20orf198) | AD | 8.88E−06 |
| NM_003677.3 | IOH56971 | Density-regulated protein | AD | 1.15E−05 |
| NM_013293.1 | IOH9999 | Transformer-2 protein homolog | AD | 1.15E−05 |
| NM_014481.2 | IOH4887 | APEX nuclease (apurinic/apyrimidinic endonuclease) 2 (APEX2), nuclear gene encoding mitochondrial protein | Control | 1.17E−05 |
| BC033856.1 | IOH21797 | La ribonucleoprotein domain family, member 1 (LARP1) | AD | 1.18E−05 |
| NM_000939.1 | IOH40048 | proopiomelanocortin (adrenocorticotropin/beta-lipotropin/alpha-melanocyte stimulating hormone/beta-melanocyte stimulating hormone/beta-endorphin) (POMC), transcript variant 2 | AD | 1.18E−05 |
| BC009348.2 | IOH12064 | cirrhosis, autosomal recessive 1A (cirhin) (CIRH1A) | AD | 1.29E−05 |
| NM_014508.2 | IOH54737 | apolipoprotein B mRNA editing enzyme, catalytic polypeptide-like 3C (APOBEC3C), mRNA. | AD | 1.46E−05 |
| NM_080659.1 | IOH7410 | chromosome 11 open reading frame 52 (C11orf52) | AD | 1.48E−05 |
| NM_022755.2 | IOH10937 | inositol 1,3,4,5,6-pentakisphosphate 2-kinase (IPPK) | AD | 1.54E−05 |

TABLE 7-continued

| Database ID | Ultimate ORF ID | Description | Indication | P-Value |
|---|---|---|---|---|
| NM_002690.1 | IOH41443 | polymerase (DNA directed), beta (POLE) | AD | 1.57E−05 |
| BC011668.1 | | Casein kinase II subunit alpha | AD | 1.57E−05 |
| NM_002128.2 | IOH2937 | high-mobility group box 1 (HMGB1) | AD | 1.62E−05 |
| BC012472.1 | IOH11069 | ubiquitin D (UBD) | AD | 1.62E−05 |
| BC030020.2 | IOH22410 | DEAD (Asp-Glu-Ala-Asp) box polypeptide 55 (DDX55) | AD | 1.62E−05 |
| BC018060.1 | IOH11303 | Ras-like without CAAX 2 (RIT2) | AD | 1.62E−05 |
| NM_003141.2 | IOH9948 | tripartite motif-containing 21 (TRIM21) | AD | 1.62E−05 |
| NM_007054.1 | IOH26900 | kinesin family member 3A (KIF3A) | AD | 1.62E−05 |
| NM_006924.3 | IOH11039 | splicing factor, arginine/serine-rich 1 (splicing factor 2, alternate splicing factor) (SFRS1), transcript variant 1 | AD | 1.67E−05 |
| NM_032563.1 | IOH40397 | late cornified envelope 3D (LCE3D) | AD | 1.67E−05 |
| NM_173080.1 | IOH34934 | small proline-rich protein 4 (SPRR4) | AD | 1.67E−05 |
| NM_003527.4 | IOH58710 | Histone H2B type 1-O | AD | 1.82E−05 |
| BC009762.2 | IOH14113 | Tripartite motif-containing protein 41 | AD | 1.82E−05 |
| NM_006861.2 | IOH10011 | RAB35, member RAS oncogene family (RAB35) | AD | 1.83E−05 |
| NM_002136.1 | IOH3526 | heterogeneous nuclear ribonucleoprotein A1 (HNRNPA1), transcript variant 1 | AD | 1.90E−05 |
| BC009623.1 | IOH9844 | nucleophosmin (nucleolar phosphoprotein B23, numatrin) (NPM1) | AD | 2.11E−05 |
| NM_021063.2 | IOH58956 | Histone H2B type 1-D | AD | 2.11E−05 |
| BC054021.1 | IOH29457 | pterin-4 alpha-carbinolamine dehydratase/dimerization cofactor of hepatocyte nuclear factor 1 alpha (TCF1) 2 (PCBD2) | AD | 2.29E−05 |
| NM_012108.1 | IOH13463 | signal transducing adaptor family member 1 (STAP1) | AD | 2.63E−05 |
| NM_023937.1 | IOH4594 | mitochondrial ribosomal protein L34 (MRPL34), nuclear gene encoding mitochondrial protein | AD | 3.15E−05 |
| XM_088679.2 | IOH43003 | Spermatid nuclear transition protein 4 | AD | 3.33E−05 |
| NM_022720.5 | IOH52788 | DiGeorge syndrome critical region gene 8 (DGCR8) | AD | 3.33E−05 |
| NM_016073.2 | IOH10649 | hepatoma-derived growth factor, related protein 3 (HDGFRP3) | AD | 3.33E−05 |
| NM_018105.1 | IOH10776 | THAP domain containing, apoptosis associated protein 1 (THAP1), transcript variant 1 | AD | 3.41E−05 |
| NM_005371.2 | IOH4172 | methyltransferase like 1 (METTL1), transcript variant 1 | AD | 3.56E−05 |
| BC029427.1 | IOH23192 | coiled-coil domain containing 23 (CCDC23) | AD | 3.61E−05 |
| NM_032476.1 | IOH13845 | mitochondrial ribosomal protein S6 (MRPS6), nuclear gene encoding mitochondrial protein | AD | 3.66E−05 |
| NM_014110.3 | IOH39485 | protein phosphatase 1, regulatory (inhibitor) subunit 8 (PPP1R8), transcript variant 1 | Control | 3.66E−05 |
| NM_003089.4 | IOH40192 | small nuclear ribonucleoprotein 70 kDa polypeptide (RNP antigen) (SNRP70) | AD | 3.88E−05 |
| BC020972.1 | | Casein kinase I isoform gamma-2 | AD | 3.88E−05 |
| BC000381.2 | IOH3454 | TBP-like 1 (TBPL1) | AD | 3.88E−05 |
| NM_007285.5 | IOH7450 | GABA(A) receptor-associated protein-like 2 (GABARAPL2) | AD | 3.99E−05 |
| NM_004060.2 | IOH4393 | cyclin G1 (CCNG1), transcript variant 1 | AD | 4.02E−05 |
| BC001780.1 | IOH4955 | Uncharacterized methyltransferase WBSCR22 | AD | 4.02E−05 |
| NM_022048.1 | IOH21026 | casein kinase 1, gamma 1 (CSNK1G1) | AD | 4.02E−05 |
| BC035256.1 | IOH27660 | Putative adenylate kinase 7 | AD | 4.19E−05 |
| NM_175887.2 | IOH27336 | proline rich 15 (PRR15) | AD | 4.22E−05 |
| BC010919.1 | IOH27800 | ribosomal protein L35 (RPL35) | AD | 4.79E−05 |

TABLE 7-continued

| Database ID | Ultimate ORF ID | Description | Indication | P-Value |
|---|---|---|---|---|
| NM_016207.2 | IOH14059 | cleavage and polyadenylation specific factor 3, 73 kDa (CPSF3) | AD | 5.24E−05 |
| BC000784.1 | IOH4711 | baculoviral IAP repeat-containing 5 (survivin) (BIRC5) | AD | 5.50E−05 |
| NM_002364.1 | IOH11315 | melanoma antigen family B, 2 (MAGEB2) | AD | 5.50E−05 |
| NM_022839.2 | IOH1783 | mitochondrial ribosomal protein S11 (MRPS11), nuclear gene encoding mitochondrial protein, transcript variant 1 | AD | 6.97E−05 |
| NM_014370.2 | IOH60262 | SFRS protein kinase 3 (SRPK3) | AD | 6.97E−05 |
| NM_016505.2 | IOH6093 | zinc finger, CCHC domain containing 17 (ZCCHC17) | AD | 7.25E−05 |
| BC030813.1 | IOH23055 | cDNA clone MGC: 22645 IMAGE: 4700961, complete cds | AD | 7.42E−05 |
| BC020803.1 | IOH14817 | developmentally regulated GTP binding protein 1 (DRG1) | AD | 7.42E−05 |
| NM_205848.1 | IOH43389 | synaptotagmin VI (SYT6) | AD | 7.94E−05 |
| NM_006398.2 | IOH59996 | Ubiquitin D | AD | 7.94E−05 |
| NM_017646.3 | IOH37769 | tRNA isopentenyltransferase 1 (TRIT1) | AD | 8.04E−05 |
| NM_006925.2 | IOH58606 | Splicing factor, arginine/serine-rich 5 | AD | 8.04E−05 |
| NM_153822.1 | IOH41107 | proteasome (prosome, macropain) 26S subunit, non-ATPase, 4 (PSMD4), transcript variant 2 | AD | 8.43E−05 |
| NM_014321.2 | IOH39827 | origin recognition complex, subunit 6 like (yeast) (ORC6L) | AD | 0.000103 |
| BC012876.1 | IOH10177 | Ig lambda chain C regions | AD | 0.000104 |
| NM_021967.1 | IOH45915 | small EDRK-rich factor 1A (telomeric) (SERF1A) | AD | 0.000104 |
| NM_003295.1 | IOH25767 | tumor protein, translationally-controlled 1 (TPT1) | AD | 0.000104 |
| NM_017503.2 | IOH12519 | surfeit 2 (SURF2) | AD | 0.000105 |
| BC018137.1 | IOH10369 | TATA box binding protein (TBP)-associated factor, RNA polymerase I, B, 63 kDa (TAF1B) | AD | 0.000108 |
| BC005004.1 | IOH4814 | family with sequence similarity 64, member A (FAM64A) | AD | 0.000114 |
| NM_152373.2 | IOH14361 | zinc finger protein 684 (ZNF684) | AD | 0.000114 |
| NM_000989.2 | IOH3809 | ribosomal protein L30 (RPL30) | AD | 0.000121 |
| NM_000800.2 | IOH21917 | fibroblast growth factor 1 (acidic) (FGF1), transcript variant 1 | AD | 0.000121 |
| NM_000975.2 | IOH1740 | ribosomal protein L11 (RPL11) | AD | 0.000142 |
| BC064144.1 | IOH40037 | spermatogenesis associated 1 (SPATA1) | Control | 0.000142 |
| PHC1695 | | C-X-C motif chemokine 11 | AD | 0.000151 |
| NM_022140.2 | IOH38016 | Band 4.1-like protein 4A | AD | 0.000159 |
| NM_016287.2 | IOH43530 | heterochromatin protein 1, binding protein 3 (HP1BP3) | AD | 0.000162 |
| BC015586.2 | IOH46065 | laminin, gamma 1 (formerly LAMB2) (LAMC1) | AD | 0.000162 |
| NM_023931.1 | IOH3950 | zinc finger protein 747 (ZNF747) | AD | 0.000168 |
| NM_153207.2 | IOH14301 | AE binding protein 2 (AEBP2) | AD | 0.000168 |
| NM_007079.2 | IOH4497 | Protein tyrosine phosphatase type IVA 3 | AD | 0.000168 |
| NM_004397.3 | IOH45655 | Probable ATP-dependent RNA helicase DDX6 | AD | 0.000172 |
| NM_012424.2 | | Ribosomal protein S6 kinase delta-1 | AD | 0.000172 |
| CCP_1BSA | NA | | Control | 0.000177 |
| NM_020239.2 | IOH21482 | CDC42 small effector 1 (CDC42SE1), transcript variant 2 | AD | 0.000186 |
| BC029378.1 | IOH23186 | telomeric repeat binding factor (NIMA-interacting) 1 (TERF1) | AD | 0.000186 |
| BC062732.1 | IOH62856 | Ig kappa chain C region | Control | 0.000211 |
| BC000306.1 | IOH3456 | hydroxyacyl-Coenzyme A dehydrogenase (HADH) | AD | 0.000216 |
| BC031650.1 | IOH22742 | Putative E3 ubiquitin-protein ligase SH3RF2 | Control | 0.000221 |
| NM_182692.1 | IOH38187 | Serine/threonine-protein kinase SRPK2 | AD | 0.000227 |
| NM_032350.3 | IOH6347 | Uncharacterized protein C7orf50 | AD | 0.000227 |
| NM_001022.3 | IOH4572 | ribosomal protein S19 (RPS19) | AD | 0.000227 |
| NM_001002913.1 | IOH26561 | peptidyl-tRNA hydrolase 1 homolog (S. cerevisiae) (PTRH1) | AD | 0.000227 |
| BC000535.1 | IOH4145 | Suppressor of SWI4 1 homolog | AD | 0.000227 |

TABLE 7-continued

| Database ID | Ultimate ORF ID | Description | Indication | P-Value |
|---|---|---|---|---|
| NM_017692.1 | IOH4894 | ataxin (APTX), transcript variant 4 | AD | 0.000233 |
| NM_000993.2 | IOH14051 | ribosomal protein L31 (RPL31), transcript variant 1 | AD | 0.000245 |
| NM_152653.1 | IOH13176 | ubiquitin-conjugating enzyme E2E 2 (UBC4/5 homolog, yeast) (UBE2E2) | AD | 0.000245 |
| NM_014891.1 | IOH4282 | PDGFA associated protein 1 (PDAP1) | AD | 0.000245 |
| NM_012148.1 | IOH39321 | double homeobox, 3 (DUX3) | AD | 0.000252 |
| NM_024046.1 | | CaM kinase-like vesicle-associated (CAMKV) | AD | 0.00028 |
| NM_022063.1 | IOH27864 | chromosome 10 open reading frame 84 (C10orf84) | AD | 0.00028 |
| BC036434.1 | IOH62212 | Serine/threonine-protein kinase VRK2 | AD | 0.00032 |
| NM_001396.2 | | Dual specificity tyrosine-phosphorylation-regulated kinase 1A | AD | 0.00032 |
| NM_004939.1 | IOH14578 | DEAD (Asp-Glu-Ala-Asp) box polypeptide 1 (DDX1) | AD | 0.00032 |
| NM_001039724.1 | IOH63165 | Nostrin | AD | 0.000331 |
| NM_138551.1 | IOH13700 | thymic stromal lymphopoietin (TSLP), transcript variant 2 | AD | 0.000332 |
| XM_379194.1 | IOH43490 | PREDICTED: Homo sapiens hypothetical LOC401068 (LOC401068) | AD | 0.000332 |
| BC007401.2 | IOH5852 | cell division cycle 25 homolog A (S. pombe) (CDC25A) | AD | 0.00034 |
| BC008902.2 | IOH46064 | GRIP and coiled-coil domain-containing protein 1 | AD | 0.00034 |
| BC019039.2 | IOH46089 | Regulator of G-protein signaling 3 | AD | 0.000407 |
| NM_016050.1 | IOH4903 | mitochondrial ribosomal protein L11 (MRPL11), nuclear gene encoding mitochondrial protein, transcript variant 1 | AD | 0.000432 |
| NM_002927.3 | IOH11040 | regulator of G-protein signaling 13 (RGS13), transcript variant 1 | AD | 0.000432 |
| NM_207430.1 | IOH59509 | FLJ46266 protein (FLJ46266), mRNA. | AD | 0.000432 |
| NM_016508.2 | IOH21339 | Cyclin-dependent kinase-like 3 | AD | 0.000432 |
| NM_197964.1 | IOH7576 | chromosome 7 open reading frame 55 (C7orf55) | AD | 0.000442 |
| BC021930.1 | IOH13703 | KIAA1530 protein (KIAA1530) | AD | 0.000442 |
| NM_145043.1 | IOH13260 | nei like 2 (E. coli) (NEIL2) | AD | 0.000442 |
| BC030586.2 | IOH22241 | signal transducing adaptor molecule (SH3 domain and ITAM motif) 1 (STAM) | AD | 0.000442 |
| BC004292.1 | IOH22899 | PHD finger protein 15 (PHF15) | Control | 0.000442 |
| BC022378.1 | IOH13502 | zinc finger with KRAB and SCAN domains 1 (ZKSCAN1) | AD | 0.000443 |
| NM_003792.1 | IOH10852 | endothelial differentiation-related factor 1 (EDF1), transcript variant alpha | AD | 0.000448 |
| BC070154.1 | IOH63011 | Non-histone chromosomal protein HMG-14 | AD | 0.000448 |
| BC010074.2 | IOH13694 | FUS interacting protein (serine/arginine-rich) 1 (FUSIP1) | AD | 0.000479 |
| NM_002201.3 | IOH6793 | interferon stimulated exonuclease gene 20 kDa (ISG20) | AD | 0.000479 |
| BC033621.2 | IOH21688 | Pseudouridylate synthase 7 homolog-like protein | AD | 0.000481 |
| NM_004114.2 | IOH13832 | fibroblast growth factor 13 (FGF13), transcript variant 1A | AD | 0.00054 |
| NM_016483.3 | IOH22255 | PHD finger protein 7 (PHF7), transcript variant 1 | AD | 0.00054 |
| NM_012420.1 | IOH22625 | interferon-induced protein with tetratricopeptide repeats 5 (IFIT5) | AD | 0.000543 |
| NM_016203.2 | IOH42382 | protein kinase, AMP-activated, gamma 2 non-catalytic subunit (PRKAG2), mRNA, transcript variant a, mRNA. | AD | 0.000543 |
| NM_014878.2 | IOH10030 | Pumilio domain-containing protein KIAA0020 | AD | 0.000544 |
| NM_018664.1 | IOH44746 | Jun dimerization protein p21SNFT (SNFT) | AD | 0.000593 |

TABLE 7-continued

| Database ID | Ultimate ORF ID | Description | Indication | P-Value |
|---|---|---|---|---|
| NM_002402.1 | IOH3706 | mesoderm specific transcript homolog (mouse) (MEST), transcript variant 1 | AD | 0.000613 |
| NM_003769.2 | IOH41184 | splicing factor, arginine/serine-rich 9 (SFRS9) | AD | 0.000613 |
| NM_018132.3 | IOH45979 | centromere protein Q (CENPQ) | AD | 0.000613 |
| NM_006072.4 | IOH40395 | chemokine (C-C motif) ligand 26 (CCL26) | AD | 0.000613 |
| NM_021029.3 | IOH4423 | ribosomal protein L36a (RPL36A) | AD | 0.000638 |
| NM_000978.2 | IOH13951 | ribosomal protein L23 (RPL23) | AD | 0.000638 |
| NM_001023.2 | IOH6083 | ribosomal protein S20 (RPS20) | AD | 0.000638 |
| BC013366.2 | IOH27815 | UNC-112 related protein 2 (URP2) | AD | 0.000638 |
| BC001327.1 | IOH3125 | interferon-related developmental regulator 2 (IFRD2) | AD | 0.000644 |
| BC000522.1 | IOH3622 | serpin peptidase inhibitor, clade F (alpha-2 antiplasmin, pigment epithelium derived factor), member 1 (SERPINF1) | AD | 0.000644 |
| NM_019067.1 | IOH13693 | guanine nucleotide binding protein-like 3 (nucleolar)-like (GNL3L) | AD | 0.000644 |
| NM_152634.1 | IOH21490 | TFS2-M domain-containing protein 1 (MGC17403) | AD | 0.000644 |
| BC011842.2 | IOH14099 | hypothetical protein FLJ11184 (FLJ11184) | AD | 0.00065 |
| BC068514.1 | IOH40543 | NF-kappaB repressing factor (NKRF) | AD | 0.00065 |
| NM_018063.3 | IOH44165 | helicase, lymphoid-specific (HELLS) | AD | 0.000661 |
| NM_198467.1 | IOH40427 | round spermatid basic protein 1-like (RSBN1L) | AD | 0.000739 |
| NM_198517.2 | IOH25922 | TBC1 domain family, member 10C (TBC1D10C) | AD | 0.000835 |
| NM_001564.1 | IOH22913 | inhibitor of growth family, member 2 (ING2) | AD | 0.000835 |
| NM_002930.1 | IOH54792 | GTP-binding protein Rit2 | AD | 0.000835 |
| NM_019058.1 | IOH6497 | DNA-damage-inducible transcript 4 protein | AD | 0.000835 |
| NM_020661.1 | IOH6382 | activation-induced cytidine deaminase (AICDA) | AD | 0.000868 |
| NM_144659.1 | IOH21795 | t-complex 10 (mouse)-like (TCP10L) | Control | 0.000868 |
| NM_173822.1 | IOH27491 | family with sequence similarity 126, member B (FAM126B) | AD | 0.000898 |
| BC056887.1 | IOH29097 | chromosome 5 open reading frame 5 (C5orf5) | AD | 0.000898 |
| BC070334.1 | IOH40810 | immunoglobulin kappa constant (IGKC) | AD | 0.000898 |
| NM_004071.1 | | Dual specificity protein kinase CLK1 | AD | 0.000898 |
| XM_378514.1 | IOH42688 | PREDICTED: *Homo sapiens* hypothetical protein LOC283663 (LOC283663), mRNA | Control | 0.000901 |
| NM_005801.2 | IOH6916 | eukaryotic translation initiation factor 1 (EIF1) | AD | 0.000906 |
| BC001487.2 | IOH12155 | TAR DNA-binding protein 43 | AD | 0.000906 |
| NM_006790.1 | IOH7249 | myotilin (MYOT) | AD | 0.000906 |
| NM_175923.2 | IOH22051 | hypothetical protein MGC42630 (MGC42630) | AD | 0.000906 |
| NM_000122.1 | IOH6320 | excision repair cross-complementing rodent repair deficiency, complementation group 3 (xeroderma pigmentosum group B complementing) (ERCC3) | AD | 0.000918 |
| NM_001819.1 | IOH3444 | chromogranin B (secretogranin 1) (CHGB) | Control | 0.000992 |
| BC010501.1 | IOH10253 | Catenin delta-1 | AD | 0.001011 |
| BC005298.1 | IOH7271 | cyclin-dependent kinase 7 (MO15 homolog, *Xenopus laevis*, cdk-activating kinase) (CDK7) | AD | 0.001015 |
| PHC0076 | | interleukin 7 (IL7) | AD | 0.001041 |
| NM_138349.2 | IOH45741 | Tumor protein p53-inducible protein 13 | AD | 0.001041 |

TABLE 7-continued

| Database ID | Ultimate ORF ID | Description | Indication | P-Value |
|---|---|---|---|---|
| BC000044.1 | IOH4604 | Spindlin-2B | AD | 0.001041 |
| NM_014747.2 | IOH4568 | regulating synaptic membrane exocytosis 3 (RIMS3) | AD | 0.001117 |
| NM_001014.2 | IOH4063 | ribosomal protein S10 (RPS10) | AD | 0.001122 |
| NM_005678.3 | IOH45840 | SNRPN upstream reading frame (SNURF), transcript variant 1 | AD | 0.001122 |
| BC010876.1 | IOH9862 | nei endonuclease VIII-like 1 (*E. coli*) (NEIL1) | AD | 0.001122 |
| BC025281.1 | IOH14071 | RNA binding motif protein 9 (RBM9) | AD | 0.001147 |
| NM_001013.2 | IOH5840 | ribosomal protein S9 (RPS9) | AD | 0.001147 |
| NM_015414.2 | IOH4985 | ribosomal protein L36 (RPL36), transcript variant 2 | AD | 0.001201 |
| NM_017566.2 | IOH11408 | kelch domain containing 4 (KLHDC4) | AD | 0.001209 |
| BC015818.1 | IOH14254 | lectin, galactoside-binding, soluble, 8 (galectin 8) (LGALS8) | AD | 0.001262 |
| BC036109.1 | IOH27253 | SECIS binding protein 2 (SECISBP2) | AD | 0.001265 |
| NM_005738.1 | IOH5077 | ADP-ribosylation factor-like 4A (ARL4A), transcript variant 1 | AD | 0.001498 |
| BC022816.1 | IOH14672 | NA | AD | 0.001498 |
| NM_024303.1 | IOH5245 | zinc finger and SCAN domain containing 5 (ZSCAN5) | AD | 0.001533 |
| BC018823.2 | IOH14860 | splicing factor, arginine/serine-rich 5 (SFRS5) | AD | 0.001533 |
| NM_024319.1 | IOH5397 | chromosome 1 open reading frame 35 (C1orf35) | AD | 0.001533 |
| PV3359 | | Ephrin receptor A3 (EPHA3), transcript variant 1 | AD | 0.00166 |
| BC006318.1 | IOH6433 | erythrocyte membrane protein band 4.9 (dematin) (EPB49) | Control | 0.001674 |
| NM_145899.1 | IOH6516 | high mobility group AT-hook 1 (HMGA1), transcript variant 1 | AD | 0.001732 |
| NM_021158.1 | | tribbles homolog 3 (*Drosophila*) (TRIB3) | AD | 0.001796 |
| NM_005794.2 | IOH41302 | dehydrogenase/reductase (SDR family) member 2 (DHRS2), transcript variant 2 | AD | 0.001796 |
| BC005807.2 | IOH6261 | stearoyl-CoA desaturase (delta-9-desaturase) (SCD) | AD | 0.001796 |
| NM_006374.2 | IOH6735 | serine/threonine kinase 25 (STE20 homolog, yeast) (STK25) | AD | 0.001796 |
| NM_152757.1 | IOH43336 | Putative uncharacterized protein C20orf200 | AD | 0.001796 |
| NM_001009880.1 | IOH42078 | chromosome 22 open reading frame 9 (C22orf9), transcript variant 2 | AD | 0.001796 |
| NM_138558.1 | IOH13759 | protein phosphatase 1, regulatory (inhibitor) subunit 8 (PPP1R8), transcript variant 2 | AD | 0.001796 |
| BC007852.1 | | Serine/threonine-protein kinase 25 | AD | 0.001796 |
| NM_012396.1 | IOH12626 | pleckstrin homology-like domain, family A, member 3 (PHLDA3) | AD | 0.001845 |
| NM_012437.2 | IOH3724 | SNAP-associated protein (SNAPAP) | AD | 0.001845 |
| PHC0205 | | interleukin 20 (IL20) | AD | 0.001845 |
| NM_016093.2 | IOH14674 | ribosomal protein L26-like 1 (RPL26L1) | AD | 0.001845 |
| NM_005902.1 | IOH27044 | SMAD family member 3 (SMAD3) | AD | 0.001845 |
| XM_375456.2 | IOH43380 | Ataxin-7-like protein 3 | AD | 0.001925 |
| NM_006275.2 | IOH3168 | splicing factor, arginine/serine-rich 6 (SFRS6) | AD | 0.00196 |
| NM_018037.1 | IOH45458 | Ral GEF with PH domain and SH3 binding motif 2 (RALGPS2), transcript variant 1 | Control | 0.001993 |
| BC011600.1 | IOH13680 | cDNA clone IMAGE: 3050953, **** WARNING: chimeric clone **** | AD | 0.002095 |
| NM_014570.2 | IOH5693 | ADP-ribosylation factor GTPase activating protein 3 (ARFGAP3) | AD | 0.002095 |
| NM_022551.2 | IOH41520 | ribosomal protein S18 (RPS18) | AD | 0.002095 |
| BC063275.1 | IOH40423 | eukaryotic translation initiation factor 2C, 1 (EIF2C1) | AD | 0.002095 |
| BC062423.1 | IOH40739 | chromosome 7 open reading frame 41 (C7orf41) | AD | 0.0021 |

TABLE 7-continued

| Database ID | Ultimate ORF ID | Description | Indication | P-Value |
|---|---|---|---|---|
| NM_170676.2 | IOH26710 | Meis homeobox 2 (MEIS2), transcript variant d | Control | 0.002174 |
| BC096708.1 | IOH63336 | Wilms tumor-associated protein | AD | 0.002181 |
| NM_199123.1 | IOH42083 | SET domain containing 3 (SETD3), transcript variant 2 | AD | 0.002181 |
| BC010907.1 | IOH12088 | PAK1 interacting protein 1 (PAK1IP1) | AD | 0.002181 |
| NM_004217.1 | | aurora kinase B (AURKB) | AD | 0.002181 |
| NM_005737.3 | IOH44753 | ADP-ribosylation factor-like 4C (ARL4C) | AD | 0.002186 |
| NM_020467.2 | IOH3994 | small trans-membrane and glycosylated protein (LOC57228), transcript variant 2 | AD | 0.002186 |
| BC021180.2 | IOH11041 | high-mobility group box 4 (HMGB4) | AD | 0.002209 |
| NM_004728.2 | IOH46173 | DEAD (Asp-Glu-Ala-Asp) box polypeptide 21 (DDX21) | AD | 0.002209 |
| BC030702.1 | IOH22356 | microcephaly, primary autosomal recessive 1 (MCPH1) | AD | 0.002281 |
| NM_003724.1 | IOH26418 | jerky homolog (mouse) (JRK), transcript variant 1 | AD | 0.002281 |
| NM_016077.1 | IOH3153 | peptidyl-tRNA hydrolase 2 (PTRH2), nuclear gene encoding mitochondrial protein | AD | 0.002329 |
| BC022362.1 | IOH14191 | cDNA clone MGC: 23888 IMAGE: 4704496, complete cds | Control | 0.002364 |
| NM_014955.2 | IOH45543 | KIAA0859 (KIAA0859), transcript variant 2 | AD | 0.002364 |
| NM_001834.2 | IOH43456 | clathrin, light chain (Lcb) (CLTB), transcript variant 1, mRNA. | Control | 0.002495 |
| NM_002045.1 | IOH6708 | growth associated protein 43 (GAP43) | Control | 0.002495 |
| NM_003503.2 | | Cell division cycle 7-related protein kinase | AD | 0.00252 |
| NM_022491.2 | IOH62643 | Sin3 histone deacetylase corepressor complex component SDS3 | Control | 0.002538 |
| NM_004987.3 | IOH55033 | LIM and senescent cell antigen-like-containing domain protein 1 | Control | 0.002538 |
| BC017212.2 | IOH13041 | PHD finger protein 11 (PHF11) | AD | 0.0027 |
| NM_019069.3 | IOH26403 | WD repeat domain 5B (WDR5B) | AD | 0.00274 |
| BC094719.1 | IOH62673 | Rho GTPase-activating protein 12 | AD | 0.002753 |
| BC021187.1 | IOH10893 | DKFZP434K028 protein (DKFZP434K028) | AD | 0.00278 |
| NM_003948.2 | | Cyclin-dependent kinase-like 2 | AD | 0.00278 |
| BC040183.2 | IOH27627 | Rap guanine nucleotide exchange factor (GEF) 4 (RAPGEF4) | AD | 0.00278 |
| NM_014061.3 | IOH10824 | melanoma antigen family H, 1 (MAGEH1) | AD | 0.00278 |
| BC032587.1 | IOH21953 | tubby like protein 3 (TULP3) | AD | 0.002953 |
| BC005332.1 | IOH7177 | cDNA clone MGC: 12418 IMAGE: 3934658, complete cds | AD | 0.003171 |
| BC033710.2 | IOH45968 | RAD54 homolog B (S. cerevisiae) (RAD54B) | AD | 0.003171 |
| BC010425.1 | IOH27813 | acyl-Coenzyme A oxidase 1, palmitoyl (ACOX1) | AD | 0.003171 |
| NM_021138.2 | IOH21846 | TNF receptor-associated factor 2 (TRAF2) | AD | 0.003171 |
| BC093990.1 | IOH62017 | Sin3 histone deacetylase corepressor complex component SDS3 | AD | 0.003185 |
| NM_014288.2 | IOH13691 | Centromere protein R | AD | 0.003283 |
| NM_024826.1 | IOH42194 | Microtubule-associated protein 9 | AD | 0.003283 |
| BC035968.1 | IOH27970 | chloride intracellular channel 5 (CLIC5) | AD | 0.003283 |
| BC096165.1 | IOH59027 | Troponin I, cardiac muscle | AD | 0.003432 |
| BC012105.1 | IOH14609 | nuclear VCP-like (NVL) | AD | 0.003548 |
| BC011924.1 | IOH12682 | unkempt homolog (Drosophila)-like (UNKL) | AD | 0.003548 |
| NM_001311.2 | IOH5361 | Cysteine-rich protein 1 | AD | 0.003548 |
| NM_014445.2 | IOH41298 | stress-associated endoplasmic reticulum protein 1 (SERP1) | AD | 0.003548 |
| NM_005979.1 | IOH1589 | S100 calcium binding protein A13 (S100A13), transcript variant 2 | AD | 0.003548 |
| BC036923.1 | IOH25928 | chromosome 9 open reading frame 150 (C9orf150) | AD | 0.003733 |

TABLE 7-continued

| Database ID | Ultimate ORF ID | Description | Indication | P-Value |
|---|---|---|---|---|
| NM_033671.1 | IOH43039 | cyclin B3 (CCNB3), transcript variant 2 | AD | 0.003733 |
| NM_201998.1 | IOH56887 | Splicing factor 1 | Control | 0.003827 |
| BC014441.1 | IOH13328 | NOL1/NOP2/Sun domain family, member 4 (NSUN4) | AD | 0.003841 |
| BC031549.1 | IOH21007 | CDC-like kinase 1 (CLK1) | AD | 0.003841 |
| NM_194290.1 | IOH42276 | cDNA FLJ42001 fis, clone SPLEN2029912 (LOC153684 protein) [Source: UniProtKB/TrEMBL; Acc: Q6ZVW3] | AD | 0.003841 |
| BC053984.1 | IOH29361 | immunoglobulin heavy variable 4-31 (IGHV4-31) | AD | 0.003841 |
| BC050563.1 | IOH26951 | hypothetical protein LOC202051 (LOC202051) | AD | 0.003841 |
| BC050718.1 | IOH27017 | polymerase (DNA directed) kappa (POLK) | AD | 0.00385 |
| BC000896.1 | IOH3226 | RAB10, member RAS oncogene family (RAB10) | AD | 0.00385 |
| NM_006252.2 | IOH29876 | AMP-activated protein_kinase A2/B1/G1: PRKAA2/B1/G1 sequences are seperated by -- (in protein list file). | AD | 0.00385 |
| BC013630.1 | IOH10193 | JTV1 gene (JTV1) | AD | 0.00385 |
| BC009108.1 | IOH10191 | cDNA clone IMAGE: 3451214 (MCM10) | AD | 0.003975 |
| BC002645.1 | IOH5243 | syntaxin 5 (STX5) | AD | 0.003975 |
| NM_138414.1 | IOH10524 | coiled-coil domain containing 101 (CCDC101) | AD | 0.004133 |
| NM_002740.1 | | protein kinase C, iota (PRKCI) | AD | 0.004133 |
| NM_002822.3 | IOH40883 | twinfilin, actin-binding protein, homolog 1 (Drosophila) (TWF1) | AD | 0.004234 |
| BC003566.1 | IOH4871 | zinc finger protein 24 (ZNF24) | AD | 0.004412 |
| NM_022756.2 | IOH13235 | Uncharacterized protein C1orf149 | AD | 0.004679 |
| NM_153035.1 | IOH27410 | chromosome 1 open reading frame 83 (C1orf83) | AD | 0.004754 |
| NM_177524.1 | IOH45900 | mesoderm specific transcript homolog (mouse) (MEST), transcript variant 2 | AD | 0.004766 |
| NM_004635.2 | IOH3889 | mitogen-activated protein kinase-activated protein kinase 3 (MAPKAPK3) | AD | 0.004766 |
| NM_005607.1 | | Focal adhesion kinase 1 | AD | 0.004766 |
| BC010697.1 | IOH9799 | RNA-binding protein 40 | AD | 0.004766 |
| NM_174942.1 | IOH26291 | GAS2-like protein 3 | AD | 0.004766 |
| BC038976.1 | IOH28763 | Rho GTPase-activating protein 15 | AD | 0.004867 |
| NM_012117.1 | IOH3162 | chromobox homolog 5 (HP1 alpha homolog, Drosophila) (CBX5) | AD | 0.004867 |
| NM_013313.3 | IOH43282 | yippee-like 1 (Drosophila) (YPEL1) | AD | 0.005052 |
| NM_148179.1 | IOH23094 | chromosome 9 open reading frame 23 (C9orf23), transcript variant 2 | AD | 0.0051 |
| BC038105.2 | IOH27173 | membrane protein, palmitoylated 7 (MAGUK p55 subfamily member 7) (MPP7) | AD | 0.0051 |
| BC091489.1 | IOH62570 | zinc finger, MYND domain containing 11, mRNA (cDNA clone MGC: 111056 IMAGE: 6186814), complete cds | AD | 0.0051 |
| BC034435.1 | IOH21500 | zinc finger CCCH-type containing 3 (ZC3H3) | AD | 0.0051 |
| NM_152736.2 | IOH14153 | Zinc finger protein 187 | AD | 0.0051 |
| NM_015014.1 | IOH23193 | RNA binding motif protein 34 (RBM34) | AD | 0.005622 |
| NM_003137.2 | | SFRS protein kinase 1 (SRPK1) | AD | 0.005622 |
| BC016486.1 | IOH21471 | lectin, galactoside-binding, soluble, 8 (galectin 8) (LGALS8) | AD | 0.005695 |
| BC000238.1 | IOH4394 | ankyrin repeat and zinc finger domain containing 1 (ANKZF1) | AD | 0.005695 |
| NM_002904.4 | IOH14621 | RD RNA binding protein (RDBP) | AD | 0.005695 |
| BC009046.1 | IOH3394 | neurogenic differentiation 1 (NEUROD1) | AD | 0.005695 |
| NM_198965.1 | IOH44500 | Parathyroid hormone-related protein | AD | 0.005695 |
| BC047776.2 | IOH26688 | coiled-coil domain containing 43 (CCDC43) | AD | 0.005695 |

TABLE 7-continued

| Database ID | Ultimate ORF ID | Description | Indication | P-Value |
|---|---|---|---|---|
| BC002914.1 | IOH5733 | WAS/WASL-interacting protein family member 1 | Control | 0.005832 |
| NM_001004306.1 | IOH40085 | similar to hypothetical protein FLJ36492 (MGC87631) | AD | 0.005898 |
| NM_006800.2 | IOH45528 | male-specific lethal 3-like 1 (Drosophila) (MSL3L1), transcript variant 3 | AD | 0.005898 |
| NM_006038.1 | IOH14383 | spermatogenesis associated 2 (SPATA2) | AD | 0.005898 |
| NM_014477.2 | IOH22106 | chromosome 20 open reading frame 10 (C20orf10) | AD | 0.005898 |
| BC027612.2 | IOH11844 | EP300-interacting inhibitor of differentiation 3 | AD | 0.005898 |
| NM_017411.2 | IOH10903 | survival of motor neuron 2, centromeric (SMN2), transcript variant d | AD | 0.005898 |
| BC004876.1 | IOH5626 | Protein MCM10 homolog | AD | 0.005898 |
| NM_201516.1 | IOH45833 | H2A histone family, member V (H2AFV), transcript variant 4 | AD | 0.005917 |
| NM_199290.2 | IOH40757 | Nascent polypeptide-associated complex subunit alpha-2 | Control | 0.006165 |
| BC006273.1 | IOH6379 | T-cell activation NFKB-like protein (TA-NFKBH) | Control | 0.006165 |
| NM_014012.2 | IOH26198 | RAS (RAD and GEM)-like GTP-binding 1 (REM1) | Control | 0.006165 |
| BC012499.1 | IOH11855 | NAD-dependent deacetylase sirtuin-1 | Control | 0.006165 |
| NM_022156.3 | IOH39856 | dihydrouridine synthase 1-like (S. cerevisiae) (DUS1L) | AD | 0.006165 |
| BC015742.1 | IOH12050 | polymerase (DNA directed), eta (POLH) | AD | 0.006497 |
| NM_001015509.1 | IOH54713 | Peptidyl-tRNA hydrolase 2, mitochondrial | AD | 0.006497 |
| NM_014366.1 | IOH4189 | guanine nucleotide binding protein-like 3 (nucleolar) (GNL3), transcript variant 1 | AD | 0.006531 |
| NM_018357.2 | IOH6558 | La ribonucleoprotein domain family, member 6 (LARP6), transcript variant 1 | AD | 0.006544 |
| BC020221.1 | IOH13291 | SH3 and cysteine rich domain (STAC) | AD | 0.006912 |
| NM_005307.1 | | G protein-coupled receptor kinase 4 | AD | 0.006912 |
| NM_017785.2 | IOH12118 | coiled-coil domain containing 99 (CCDC99) | AD | 0.006926 |
| BC026101.2 | IOH10652 | nudE nuclear distribution gene E homolog (A. nidulans)-like 1 (NDEL1) | AD | 0.006926 |
| NM_175571.2 | IOH44212 | GTPase, IMAP family member 8 (GIMAP8) | AD | 0.006926 |
| NM_004286.2 | IOH14552 | GTP binding protein 1 (GTPBP1) | AD | 0.006926 |
| BC072461.1 | IOH62565 | Cysteine and histidine-rich domain-containing protein 1 | AD | 0.006926 |
| BC047945.1 | IOH26362 | tripartite motif-containing 69 (TRIM69) | AD | 0.006926 |
| BC005858.1 | IOH5967 | fibronectin 1 (FN1) | AD | 0.006926 |
| NM_001722.2 | IOH4103 | polymerase (RNA) III (DNA directed) polypeptide D, 44 kDa (POLR3D) | AD | 0.006926 |
| NM_024333.1 | IOH4546 | Fibronectin type III and SPRY domain-containing protein 1 | AD | 0.006926 |
| NM_144595.1 | IOH25832 | SLAIN motif family, member 1 (SLAIN1), transcript variant 2 | AD | 0.006926 |
| NM_002469.1 | IOH13806 | myogenic factor 6 (herculin) (MYF6) | AD | 0.006926 |
| BC053866.1 | IOH28947 | endothelin 3 (EDN3) | AD | 0.006926 |
| NM_001319.5 | IOH10417 | casein kinase 1, gamma 2 (CSNK1G2) | AD | 0.006926 |
| BC006124.1 | IOH6586 | IMP (inosine monophosphate) dehydrogenase 2 (IMPDH2) | AD | 0.006926 |
| NM_014667.1 | IOH29305 | vestigial like 4 (Drosophila) (VGLL4) | AD | 0.006926 |
| NM_031465.2 | IOH6623 | chromosome 12 open reading frame 32 (C12orf32) | AD | 0.006926 |
| NM_182612.1 | IOH42453 | Parkinson disease 7 domain containing 1 (PDDC1) | AD | 0.006926 |

TABLE 7-continued

| Database ID | Ultimate ORF ID | Description | Indication | P-Value |
|---|---|---|---|---|
| PV4803 | | epidermal growth factor receptor (erythroblastic leukemia viral (v-erb-b) oncogene homolog, avian) (EGFR); see catalog number for detailed information on wild-type or point mutant status | AD | 0.006926 |
| NM_152266.1 | IOH13579 | chromosome 19 open reading frame 40 (C19orf40) | AD | 0.006926 |
| NM_000997.2 | IOH1585 | ribosomal protein L37 (RPL37) | AD | 0.00699 |
| BC001728.1 | IOH4430 | TCF3 fusion partner | AD | 0.00699 |
| BC007015.1 | IOH29312 | cyclin E2 (CCNE2) | AD | 0.00699 |
| NM_022347.1 | IOH41552 | interferon responsive gene 15 (IFRG15) | AD | 0.00699 |
| BC031821.1 | IOH22188 | Secernin-3 | AD | 0.007845 |
| NM_016304.2 | IOH7552 | chromosome 15 open reading frame 15 (C15orf15) | AD | 0.007845 |
| BC069677.1 | IOH61907 | Regulator of G-protein signaling 8 | AD | 0.008076 |
| BC013331.1 | IOH13858 | H2A histone family, member Y (H2AFY) | AD | 0.008076 |
| NM_017838.2 | IOH4642 | nucleolar protein family A, member 2 (H/ACA small nucleolar RNPs) (NOLA2), transcript variant 1 | AD | 0.008076 |
| BC013796.1 | IOH21478 | adaptor-related protein complex 2, mu 1 subunit (AP2M1) | AD | 0.008076 |
| NM_080743.2 | IOH10836 | serine-arginine repressor protein (35 kDa) (SRrp35) | AD | 0.008076 |
| BC000190.1 | IOH4410 | zinc finger, C3HC-type containing 1 (ZC3HC1) | AD | 0.008141 |
| BC036089.1 | IOH27267 | myeloid/lymphoid or mixed-lineage leukemia (trithorax homolog, *Drosophila*); translocated to, 3 (MLLT3) | AD | 0.008141 |
| NM_018215.2 | IOH40888 | hypothetical protein FLJ10781 (FLJ10781), transcript variant 1 | AD | 0.008141 |
| BC095401.1 | IOH62645 | AKT-interacting protein | AD | 0.008141 |
| BC006456.1 | IOH5963 | family with sequence similarity 21, member C (FAM21C) | Control | 0.008294 |
| BC033777.2 | IOH21769 | amyotrophic lateral sclerosis 2 (juvenile) chromosome region, candidate 8 (ALS2CR8) | Control | 0.008368 |
| NM_001008572.1 | IOH45757 | tubulin tyrosine ligase-like family, member 1 (TTLL1), transcript variant 2 | AD | 0.008509 |
| BC103812.1 | IOH63363 | Alpha-ketoglutarate-dependent dioxygenase alkB homolog 3 | AD | 0.008559 |
| BC036365.1 | IOH22309 | PH domain-containing protein C10orf81 | AD | 0.008559 |
| NM_024718.2 | IOH40918 | chromosome 9 open reading frame 86 (C9orf86) | Control | 0.009125 |
| BC013031.1 | IOH13433 | Pleckstrin homology-like domain family B member 1 | Control | 0.009125 |
| NM_022110.2 | IOH10458 | FK506 binding protein like (FKBPL) | Control | 0.009125 |
| NM_016047.1 | IOH11089 | splicing factor 3B, 14 kDa subunit (SF3B14) | AD | 0.009549 |
| BC014949.1 | IOH13331 | DEXH (Asp-Glu-X-His) box polypeptide 58 (DHX58) | AD | 0.009549 |
| BC047690.1 | IOH28834 | Ras-related protein M-Ras | AD | 0.009633 |
| NM_001894.2 | IOH21160 | casein kinase 1, epsilon (CSNK1E), transcript variant 2 | AD | 0.009633 |
| NM_006482.1 | | Dual specificity tyrosine-phosphorylation-regulated kinase 2 | AD | 0.009633 |
| NM_025104.2 | IOH59472 | Protein DBF4 homolog B | AD | 0.009633 |
| BC004410.1 | IOH5586 | Zinc finger protein castor homolog 1 | Control | 0.009819 |
| NM_017819.1 | IOH45746 | RNA (guanine-9-)-methyltransferase domain-containing protein 1, mitochondrial | AD | 0.009872 |
| BC029382.1 | IOH23139 | Angiogenic factor with G patch and FHA domains 1 | Control | 0.010166 |
| NM_199139.1 | IOH44783 | XIAP associated factor-1 (XAF1), transcript variant 2 | AD | 0.010291 |
| NM_003910.2 | IOH23209 | BUD31 homolog (*S. cerevisiae*) (BUD31) | AD | 0.010291 |

TABLE 7-continued

| Database ID | Ultimate ORF ID | Description | Indication | P-Value |
|---|---|---|---|---|
| BC000442.1 | | Serine/threonine-protein kinase 12 | AD | 0.010291 |
| BC028711.2 | IOH11814 | cancer/testis antigen CT45-3 (CT45-3) | AD | 0.010291 |
| NM_018158.1 | IOH38323 | solute carrier family 4 (anion exchanger), member 1, adaptor protein (SLC4A1AP) | AD | 0.010774 |
| BC034692.1 | IOH22176 | anillin, actin binding protein (ANLN) | AD | 0.010774 |
| NM_173605.1 | IOH21690 | potassium channel regulator (KCNRG), transcript variant 1 | AD | 0.010774 |
| NM_014047.1 | IOH11187 | chromosome 19 open reading frame 53 (C19orf53) | AD | 0.010774 |
| BC073791.1 | IOH63073 | immunoglobulin kappa constant, mRNA (cDNA clone MGC: 88809 IMAGE: 6279986), complete cds | AD | 0.010774 |
| BC014928.1 | IOH10102 | MYC-induced nuclear antigen | AD | 0.010774 |
| BC053656.1 | IOH28981 | EGF-like repeats and discoidin I-like domains 3 (EDIL3) | AD | 0.010774 |
| XM_378879.2 | IOH42915 | PREDICTED: *Homo sapiens* hypothetical LOC400763 (LOC400763) | AD | 0.010774 |
| NM_017817.1 | IOH12515 | RAB20, member RAS oncogene family (RAB20) | AD | 0.010774 |
| BC031608.1 | IOH22796 | REST corepressor 3 (RCOR3) | AD | 0.010774 |
| BC047722.1 | IOH26651 | hypothetical protein MGC52110 (MGC52110) | AD | 0.010774 |
| BC020726.1 | IOH12969 | sciellin (SCEL) | AD | 0.010774 |
| NM_024039.1 | IOH4379 | MIS12, MIND kinetochore complex component, homolog (yeast) (MIS12) | AD | 0.010774 |
| BC026213.1 | IOH11042 | F-box/WD repeat-containing protein 11 | AD | 0.010774 |
| NM_002135.3 | IOH10133 | nuclear receptor subfamily 4, group A, member 1 (NR4A1), transcript variant 1 | AD | 0.010822 |
| NM_015939.2 | IOH3137 | tRNA methyltransferase 6 homolog (*S. cerevisiae*) (TRMT6) | AD | 0.010846 |
| NM_018039.2 | IOH43857 | jumonji domain containing 2D (JMJD2D) | AD | 0.010846 |
| NM_007373.2 | IOH26711 | soc-2 suppressor of clear homolog (*C. elegans*) (SHOC2) | AD | 0.010846 |
| BC022996.1 | IOH10666 | SH3 domain-binding protein 2 | Control | 0.011036 |
| BC067120.1 | IOH40451 | protein tyrosine phosphatase domain containing 1, mRNA (cDNA clone MGC: 70358 IMAGE: 5539182), complete cds | AD | 0.011036 |
| BC027729.1 | IOH14530 | tetra-peptide repeat homeobox-like (TPRXL) | Control | 0.01201 |
| BC054520.1 | IOH28900 | myocyte enhancer factor 2D (MEF2D) | Control | 0.01201 |
| NM_015918.2 | IOH10987 | processing of precursor 5, ribonuclease P/MRP subunit (*S. cerevisiae*) (POP5), transcript variant 1 | AD | 0.012016 |
| NM_152677.1 | IOH34851 | zinc finger and SCAN domain containing 4 (ZSCAN4) | AD | 0.012016 |
| BC008902.2 | IOH7022 | GRIP and coiled-coil domain-containing protein 1 | AD | 0.012016 |
| NM_001008239.1 | IOH45708 | chromosome 18 open reading frame 25 (C18orf25), transcript variant 2 | AD | 0.012016 |
| NM_183397.1 | IOH44678 | peroxisomal membrane protein 4, 24 kDa (PXMP4), transcript variant 2 | AD | 0.012016 |
| NM_006337.3 | IOH12378 | microspherule protein 1 (MCRS1), transcript variant 1 | AD | 0.012016 |
| NM_203305.1 | IOH26383 | family with sequence similarity 102, member A (FAM102A), transcript variant 2 | Control | 0.012091 |
| BC034401.1 | IOH22782 | cDNA clone IMAGE: 5172086, partial cds | AD | 0.012151 |
| NM_006755.1 | IOH2052 | transaldolase 1 (TALDO1) | AD | 0.012151 |
| NM_004853.1 | IOH9940 | syntaxin 8 (STX8) | AD | 0.012151 |
| BC036910.1 | IOH25910 | hypothetical LOC388882 (LOC388882) | AD | 0.012151 |

TABLE 7-continued

| Database ID | Ultimate ORF ID | Description | Indication | P-Value |
|---|---|---|---|---|
| BC094687.1 | IOH62581 | Elongation factor 1-alpha 1 | AD | 0.012151 |
| BC011713.2 | IOH22973 | tRNA methyltransferase 12 homolog (*S. cerevisiae*) (TRMT12) | Control | 0.013018 |
| NM_006263.1 | IOH3647 | proteasome (prosome, macropain) activator subunit 1 (PA28 alpha) (PSME1), transcript variant 1 | Control | 0.013018 |
| NM_144608.1 | IOH14178 | hexamthylene bis-acetamide inducible 2 (HEXIM2) | AD | 0.013303 |
| NM_024038.2 | IOH5926 | chromosome 19 open reading frame 43 (C19orf43) | Control | 0.013303 |
| NM_003831.1 | IOH20968 | RIO kinase 3 (yeast) (RIOK3) | AD | 0.013332 |
| BC020555.1 | IOH10305 | SERPINE1 mRNA binding protein 1 (SERBP1) | Control | 0.013333 |
| BC009250.1 | IOH27775 | guanine nucleotide binding protein-like 2 (nucleolar) (GNL2) | AD | 0.013333 |
| BC032598.1 | IOH21976 | NHL repeat containing 2 (NHLRC2) | AD | 0.013369 |
| NM_018697.3 | IOH37734 | LanC lantibiotic synthetase component C-like 2 (bacterial) (LANCL2) | AD | 0.013369 |
| NM_024104.1 | IOH3754 | chromosome 19 open reading frame 42 (C19orf42) | AD | 0.013369 |
| BC030665.1 | IOH22451 | Sulfotransferase 4A1 | AD | 0.013369 |
| BC004955.1 | IOH5528 | ATPase inhibitory factor 1 (ATPIF1) | AD | 0.013369 |
| BC009010.1 | IOH3292 | Uncharacterized protein C6orf142 homolog | AD | 0.013369 |
| BC012887.1 | IOH25768 | Nucleolar and spindle-associated protein 1 | AD | 0.013369 |
| BC015066.1 | IOH13784 | core-binding factor, runt domain, alpha subunit 2; translocated to, 2 (CBFA2T2) | AD | 0.013369 |
| BC052303.1 | IOH28113 | Rho GTPase activating protein 4 (ARHGAP4) | AD | 0.013369 |
| NM_080414.1 | IOH42243 | vacuolar protein sorting 16 homolog (*S. cerevisiae*) (VPS16), transcript variant 2 | AD | 0.013369 |
| NM_001790.2 | IOH14569 | cell division cycle 25 homolog C (*S. pombe*) (CDC25C), transcript variant 1 | AD | 0.013369 |
| PHC0045 | | interleukin 4 (IL4), transcript variant 1 | AD | 0.013369 |
| NM_145041.1 | IOH13199 | transmembrane protein 106A (TMEM106A) | AD | 0.013369 |
| NM_021639.2 | IOH10045 | GC-rich promoter binding protein 1-like 1 (GPBP1L1) | AD | 0.013369 |
| BC028295.1 | IOH25815 | peptidase D (PEPD) | AD | 0.013369 |
| PV3612 | | aurora kinase A (AURKA), transcript variant 2 | AD | 0.013369 |
| NM_032321.1 | IOH6608 | hypothetical protein MGC13057 (MGC13057), transcript variant 4 | AD | 0.013369 |
| BC010033.1 | IOH27835 | quinolinate phosphoribosyltransferase (nicotinate-nucleotide pyrophosphorylase (carboxylating)) (QPRT) | AD | 0.013369 |
| NM_001064.1 | IOH61026 | Transketolase | AD | 0.013369 |
| NM_017572.2 | IOH53775 | MAP kinase-interacting serine/threonine-protein kinase 2 | AD | 0.013967 |
| NM_022650.1 | IOH41794 | RAS p21 protein activator (GTPase activating protein) 1 (RASA1), transcript variant 2 | AD | 0.013967 |
| NM_020781.2 | IOH45442 | zinc finger protein 398 (ZNF398), transcript variant 2 | AD | 0.013967 |
| NM_182597.1 | IOH44503 | Coiled-coil domain-containing transmembrane protein C7orf53 | Control | 0.014519 |
| NM_001008211.1 | IOH57143 | Optineurin | Control | 0.014972 |
| NM_006246.2 | IOH29856 | protein phosphatase 2, regulatory subunit B', epsilon isoform (PPP2R5E) | Control | 0.014972 |
| NM_148912.2 | IOH40097 | abhydrolase domain containing 11 (ABHD11) | Control | 0.014972 |
| BC053617.1 | IOH29004 | B-cell CLL/lymphoma 10 (BCL10) | Control | 0.014972 |
| NM_021643.1 | IOH21149 | tribbles homolog 2 (*Drosophila*) (TRIB2) | Control | 0.014972 |

TABLE 7-continued

| Database ID | Ultimate ORF ID | Description | Indication | P-Value |
|---|---|---|---|---|
| NM_024313.1 | IOH5392 | nucleolar protein 12 (NOL12) | Control | 0.014972 |
| NM_002735.1 | IOH42254 | cAMP-dependent protein kinase type I-beta regulatory subunit | Control | 0.014972 |
| NM_032929.1 | IOH7540 | ubiquitin specific protease 45 (USP45) | Control | 0.014972 |
| NM_024692.3 | IOH42634 | CAP-GLY domain containing linker protein family, member 4 (CLIP4) | Control | 0.015635 |
| NM_002391.1 | IOH13794 | midkine (neurite growth-promoting factor 2) (MDK), transcript variant 3 | AD | 0.015891 |
| NM_006298.2 | IOH34757 | zinc finger protein 192 (ZNF192) | AD | 0.015891 |
| BC047536.1 | IOH27737 | sciellin (SCEL) | AD | 0.015891 |
| NM_139062.1 | IOH23025 | casein kinase 1, delta (CSNK1D), transcript variant 2 | AD | 0.015891 |
| NM_005639.1 | IOH29114 | synaptotagmin I (SYT1) | AD | 0.015891 |
| BC006811.1 | IOH3174 | peroxisome proliferator-activated receptor gamma (PPARG) | AD | 0.015961 |
| BC008364.1 | IOH5969 | heterogeneous nuclear ribonucleoprotein C (C1/C2) (HNRPC) | AD | 0.015961 |
| NM_032345.1 | IOH6625 | within bgcn homolog (Drosophila) (WIBG) | AD | 0.015961 |
| BC040949.1 | IOH26268 | myocyte enhancer factor 2D (MEF2D) | Control | 0.016176 |
| NM_005522.3 | IOH21992 | homeobox A1 (HOXA1), transcript variant 1 | Control | 0.016176 |
| BC016825.1 | IOH14707 | spire homolog 1 (Drosophila) (SPIRE1) | AD | 0.016623 |
| NM_020664.3 | IOH9825 | 2,4-dienoyl CoA reductase 2, peroxisomal (DECR2) | AD | 0.017399 |
| NM_173547.2 | IOH11612 | tripartite motif-containing 65 (TRIM65) | Control | 0.017399 |
| NM_017542.3 | IOH43680 | pogo transposable element with KRAB domain (POGK) | AD | 0.017399 |
| NM_003160.1 | | Serine/threonine-protein kinase 13 | AD | 0.017399 |
| NM_032550.1 | IOH10814 | actin filament associated protein 1-like 2 (AFAP1L2), transcript variant 2 | Control | 0.017478 |
| NM_004527.2 | IOH40231 | mesenchyme homeobox 1 (MEOX1), transcript variant 1 | Control | 0.017478 |
| BC031687.1 | IOH21501 | drebrin-like (DBNL) | Control | 0.017478 |
| BC026346.1 | IOH10816 | family with sequence similarity 84, member A (FAM84A) | AD | 0.017478 |
| BC041037.1 | IOH28003 | immunoglobulin heavy constant mu (IGHM) | AD | 0.017478 |
| BC028039.1 | IOH11511 | hypothetical protein MGC39900 (MGC39900) | Control | 0.01748 |
| BC033677.1 | IOH40219 | Uncharacterized protein C9orf114 | AD | 0.017534 |
| BC055427.1 | IOH28811 | TRAF2 and NCK interacting kinase (TNIK) | AD | 0.017534 |
| NM_016648.1 | IOH41297 | La ribonucleoprotein domain family, member 7 (LARP7), transcript variant 1 | AD | 0.017664 |
| BC064145.1 | IOH40031 | CDK5 regulatory subunit associated protein 1-like 1 (CDKAL1) | AD | 0.017664 |
| NM_138565.1 | IOH6227 | cortactin (CTTN), transcript variant 2 | AD | 0.017664 |
| NM_018441.2 | IOH4050 | peroxisomal trans-2-enoyl-CoA reductase (PECR) | Control | 0.018299 |
| NM_022823.1 | IOH21980 | fibronectin type III domain containing 4 (FNDC4) | AD | 0.018299 |
| NM_015871.2 | IOH4113 | zinc finger protein 593 (ZNF593) | Control | 0.01832 |
| NM_024096.1 | IOH3203 | XTP3-transactivated protein A (XTP3TPA) | Control | 0.01863 |
| BC023546.2 | IOH29323 | LIM and calponin homology domains 1 (LIMCH1) | Control | 0.018757 |
| NM_015621.2 | IOH43603 | coiled-coil domain containing 69 (CCDC69) | Control | 0.018757 |
| BC006104.1 | IOH6588 | RIO kinase 1 (yeast) (RIOK1) | AD | 0.018757 |
| BC014975.1 | IOH14285 | family with sequence similarity 136, member A (FAM136A) | AD | 0.018844 |
| NM_138730.1 | IOH9857 | high mobility group nucleosomal binding domain 3 (HMGN3), transcript variant 2 | AD | 0.018844 |

TABLE 7-continued

| Database ID | Ultimate ORF ID | Description | Indication | P-Value |
|---|---|---|---|---|
| BC000226.1 | IOH4362 | ubiquitin specific peptidase 47 (USP47) | Control | 0.019006 |
| NM_007242.3 | IOH3925 | DEAD (Asp-Glu-Ala-As) box polypeptide 19B (DDX19B), transcript variant 1 | Control | 0.019006 |
| NM_025004.1 | IOH43200 | Coiled-coil domain-containing protein 15 | AD | 0.019314 |
| NM_004092.2 | IOH54943 | Enoyl-CoA hydratase, mitochondrial | AD | 0.019314 |
| NM_021107.1 | IOH6073 | mitochondrial ribosomal protein S12 (MRPS12), nuclear gene encoding mitochondrial protein, transcript variant 1 | AD | 0.019314 |
| NM_053049.2 | IOH54667 | Urocortin-3 | AD | 0.019314 |
| NM_001545.1 | IOH11951 | immature colon carcinoma transcript 1 (ICT1) | AD | 0.019314 |
| NM_148571.1 | IOH41376 | mitochondrial ribosomal protein L27 (MRPL27), nuclear gene encoding mitochondrial protein, transcript variant 2 | AD | 0.019314 |
| NM_001003799.1 | IOH45702 | TCR gamma alternate reading frame protein (TARP), nuclear gene encoding mitochondrial protein, transcript variant 1 | AD | 0.019314 |
| BC017227.1 | IOH12094 | phosducin-like (PDCL) | AD | 0.019314 |
| NM_172159.2 | IOH25842 | potassium voltage-gated channel, shaker-related subfamily, beta member 1 (KCNAB1), transcript variant 3 | AD | 0.019314 |
| NM_000462.2 | IOH38426 | ubiquitin protein ligase E3A (human papilloma virus E6-associated protein, Angelman syndrome) (UBE3A), transcript variant 2 | AD | 0.019314 |
| XM_210860.4 | IOH44696 | PREDICTED: *Homo sapiens* hypothetical LOC283034 (LOC283034) | AD | 0.019314 |
| BC022344.1 | IOH14799 | twinfilin, actin-binding protein, homolog 1 (*Drosophila*) (TWF1) | AD | 0.019314 |
| NM_005037.3 | IOH39661 | peroxisome proliferator-activated receptor gamma (PPARG), transcript variant 4 | AD | 0.019314 |
| NM_022977.1 | IOH42656 | acyl-CoA synthetase long-chain family member 4 (ACSL4), transcript variant 2 | AD | 0.019314 |
| NM_006217.2 | IOH11838 | serpin peptidase inhibitor, clade I (pancpin), member 2 (SERPINI2) | AD | 0.019314 |
| NM_024979.2 | IOH23111 | Guanine nucleotide exchange factor DBS | AD | 0.019314 |
| NM_016286.1 | IOH4017 | dicarbonyl/L-xylulose reductase (DCXR) | AD | 0.019314 |
| NM_003160.1 | | Serine/threonine-protein kinase 13 | AD | 0.019314 |
| NM_015687.2 | IOH38763 | filamin A interacting protein 1 (FILIP1) | AD | 0.019314 |
| BC005871.2 | IOH46098 | chromosome 10 open reading frame 58 (C10orf58) | AD | 0.019314 |
| NM_016216.2 | IOH57112 | Lariat debranching enzyme | AD | 0.019314 |
| NM_017856.1 | IOH3877 | gem (nuclear organelle) associated protein 8 (GEMIN8), transcript variant 3 | AD | 0.019314 |
| NM_015869.2 | IOH36704 | peroxisome proliferator-activated receptor gamma (PPARG), transcript variant 2 | AD | 0.019314 |
| NM_001003397.1 | IOH58745 | Tumor protein D53 | AD | 0.019314 |
| NM_001018061.1 | IOH57329 | UPF0544 protein C5orf45 [Source: UniProtKB/Swiss-Prot; Acc: Q6NTE8] | AD | 0.019314 |
| NM_173060.1 | IOH52621 | Calpastatin | Control | 0.019703 |
| BC013900.1 | IOH27818 | chromosome 12 open reading frame 41 (C12orf41) | AD | 0.020182 |
| BC022988.1 | IOH22366 | chromosome 6 open reading frame 65 (C6orf65) | AD | 0.020182 |
| NM_006299.2 | IOH12838 | zinc finger protein 193 (ZNF193) | AD | 0.020182 |
| BC018847.1 | IOH14862 | Transaldolase | AD | 0.020182 |
| BC052805.1 | IOH29378 | erythrocyte membrane protein band 4.9 (dematin) (EPB49) | Control | 0.020182 |

TABLE 7-continued

| Database ID | Ultimate ORF ID | Description | Indication | P-Value |
|---|---|---|---|---|
| NM_139355.1 | IOH4506 | megakaryocyte-associated tyrosine kinase (MATK), transcript variant 1 | AD | 0.0209 |
| NM_207356.1 | IOH40044 | chromosome 1 open reading frame 174 (C1orf174) | AD | 0.0209 |
| NM_001008737.1 | IOH42047 | hypothetical LOC401052 (LOC401052) | AD | 0.0209 |
| NM_145109.1 | IOH21715 | mitogen-activated protein kinase kinase 3 (MAP2K3), transcript variant B | AD | 0.0209 |
| BC017114.1 | IOH9995 | oligonucleotide/oligosaccharide-binding fold containing 2A (OBFC2A) | AD | 0.0209 |
| XM_086879.4 | IOH43381 | PREDICTED: *Homo sapiens* hypothetical LOC150371 (LOC150371) | AD | 0.0209 |
| NM_078630.1 | IOH37755 | male-specific lethal 3-like 1 (*Drosophila*) (MSL3L1), transcript variant 2 | AD | 0.0209 |
| NM_005197.2 | IOH56874 | Forkhead box protein N3 | AD | 0.0209 |
| NM_004602.2 | IOH62672 | Double-stranded RNA-binding protein Staufen homolog 1 | AD | 0.021101 |
| BC017504.1 | IOH12256 | Differentially expressed in FDCP 6 homolog | AD | 0.021101 |
| NM_014763.2 | IOH23003 | mitochondrial ribosomal protein L19 (MRPL19), nuclear gene encoding mitochondrial protein | Control | 0.021448 |
| NM_003590.2 | IOH26262 | cullin 3 (CUL3) | AD | 0.021703 |
| NM_145702.1 | IOH40861 | tigger transposable element derived 1 (TIGD1) | AD | 0.021703 |
| BC001935.1 | IOH5068 | cyclin-dependent kinase inhibitor 1A (p21, Cip1) (CDKN1A) | AD | 0.022172 |
| NM_031472.1 | IOH5640 | tRNA phosphotransferase 1 (TRPT1), transcript variant 2 | Control | 0.023801 |
| NM_032141.1 | IOH43707 | coiled-coil domain containing 55 (CCDC55), transcript variant 1 | Control | 0.024725 |
| NM_004965.3 | IOH4772 | high-mobility group nucleosome binding domain 1 (HMGN1) | AD | 0.024725 |
| BC032508.1 | IOH62199 | PNMA-like 1, mRNA (cDNA clone MGC: 45422 IMAGE: 5246377), complete cds | AD | 0.025032 |
| BC013966.2 | IOH12372 | family with sequence similarity 64, member A (FAM64A) | AD | 0.025523 |
| NM_020236.2 | IOH13751 | mitochondrial ribosomal protein L1 (MRPL1), nuclear gene encoding mitochondrial protein | AD | 0.025523 |
| BC043247.2 | IOH28730 | transducin-like enhancer of split 3 (E(sp1) homolog, *Drosophila*) (TLE3) | AD | 0.025523 |
| BC057806.1 | IOH29150 | insulin-like growth factor binding protein 1 (IGFBP1) | AD | 0.025523 |
| NM_006573.2 | IOH12947 | tumor necrosis factor (ligand) superfamily, member 13b (TNFSF13B) | AD | 0.025523 |
| BC025406.1 | IOH11226 | phosphodiesterase 4D interacting protein (myomegalin) (PDE4DIP) | AD | 0.025523 |
| BC002559.1 | IOH4053 | YTH domain family, member 2 (YTHDF2) | AD | 0.025523 |
| NM_052926.1 | IOH35779 | Paraneoplastic antigen-like protein 5 | AD | 0.025523 |
| NM_006254.3 | IOH26352 | protein kinase C, delta (PRKCD), transcript variant 1 | AD | 0.025523 |
| BC022003.1 | IOH11205 | myotubularin related protein 9 (MTMR9) | AD | 0.025523 |
| BC043348.2 | IOH26348 | retinitis pigmentosa 2 (X-linked recessive) (RP2) | AD | 0.025523 |
| NM_018010.2 | IOH12676 | intraflagellar transport 57 homolog (*Chlamydomonas*) (IFT57) | AD | 0.025523 |
| BC044851.1 | IOH27643 | vacuolar protein sorting 41 homolog (*S. cerevisiae*) (VPS41) | AD | 0.025523 |
| BC068094.1 | IOH40788 | SH3 domain and tetratricopeptide repeats 1 (SH3TC1) | AD | 0.025523 |
| NM_020961.2 | IOH6104 | KIAA1627 protein (KIAA1627) | AD | 0.025523 |
| PV3757 | | myosin light chain kinase 2, skeletal muscle (MYLK2) | AD | 0.025523 |
| NM_002451.3 | IOH54928 | methylthioadenosine phosphorylase (MTAP), mRNA. | AD | 0.025523 |

TABLE 7-continued

| Database ID | Ultimate ORF ID | Description | Indication | P-Value |
|---|---|---|---|---|
| NM_000281.1 | IOH6468 | pterin-4 alpha-carbinolamine dehydratase/dimerization cofactor of hepatocyte nuclear factor 1 alpha (TCF1) (PCBD1) | AD | 0.025523 |
| NM_144982.1 | IOH12275 | coiled-coil domain containing 131 (CCDC131) | AD | 0.025523 |
| NM_017927.2 | IOH43690 | mitofusin 1 (MFN1), nuclear gene encoding mitochondrial protein, transcript variant 2 | AD | 0.025523 |
| NM_002150.1 | IOH14718 | 4-hydroxyphenylpyruvate dioxygenase | AD | 0.025523 |
| NM_016267.1 | IOH2890 | vestigial like 1 (*Drosophila*) (VGLL1) | AD | 0.025523 |
| BC067299.1 | IOH40040 | Mdm4, transformed 3T3 cell double minute 4, p53 binding protein (mouse) (MDM4) | AD | 0.025523 |
| XM_378988.2 | IOH41598 | PREDICTED: *Homo sapiens* hypothetical LOC400849 (LOC400849) | AD | 0.025523 |
| NM_006466.1 | IOH14273 | polymerase (RNA) III (DNA directed) polypeptide F, 39 kDa (POLR3F) | AD | 0.025523 |
| BC042608.1 | IOH27462 | family with sequence similarity 90, member A1 (FAM90A1) | AD | 0.025523 |
| NM_025136.1 | IOH6524 | optic atrophy 3 (autosomal recessive, with chorea and spastic paraplegia) (OPA3), transcript variant 2 | AD | 0.025523 |
| BC012620.1 | IOH12299 | golgi SNAP receptor complex member 1 (GOSR1) | AD | 0.025523 |
| NM_139244.2 | IOH44877 | syntaxin binding protein 5 (tomosyn) (STXBP5) | AD | 0.025523 |
| NM_015929.2 | IOH7138 | lipoyltransferase 1 (LIPT1), transcript variant 1 | AD | 0.025523 |
| PV3366 | | v-erb-b2 erythroblastic leukemia viral oncogene homolog 2, neuro/glioblastoma derived oncogene homolog (avian) (ERBB2), transcript variant 2 | AD | 0.025523 |
| NM_133629.1 | IOH43384 | RAD51-like 3 (*S. cerevisiae*) (RAD51L3), transcript variant 4 | AD | 0.025523 |
| XM_294794.1 | IOH42923 | PREDICTED: *Homo sapiens* similar to putative membrane-bound dipeptidase 2 (LOC339065) | AD | 0.025523 |
| BC012289.1 | IOH11447 | KIAA0515 (KIAA0515) | AD | 0.025523 |
| BC029444.1 | IOH23178 | immunoglobulin kappa constant (IGKC) | AD | 0.025523 |
| BC015109.1 | IOH14036 | 39S ribosomal protein L1, mitochondrial | AD | 0.025523 |
| NM_024578.1 | IOH23128 | occludin/ELL domain containing 1 (OCEL1) | AD | 0.025523 |
| NM_003908.1 | IOH3554 | eukaryotic translation initiation factor 2, subunit 2 beta, 38 kDa (EIF2S2) | AD | 0.025523 |
| BC001726.1 | IOH4820 | Nucleolar protein 11 | AD | 0.025523 |
| BC003666.2 | IOH6106 | NAD synthetase 1 (NADSYN1) | AD | 0.025523 |
| NM_198491.1 | IOH41015 | family with sequence similarity 92, member B (FAM92B) | AD | 0.025523 |
| PV3817 | | WEE1 homolog (*S. pombe*) (WEE1) | AD | 0.025523 |
| BC000974.2 | IOH3026 | WDR45-like (WDR45L) | AD | 0.025523 |
| BC053675.1 | IOH29030 | thymopoietin (TMPC) | AD | 0.025523 |
| BC033292.1 | IOH26782 | interleukin 20 receptor beta (IL20RB) | AD | 0.025523 |
| BC002509.1 | IOH3968 | PHD finger protein 23 | AD | 0.025523 |
| BC006969.1 | IOH7343 | dynein, cytoplasmic 2, light intermediate chain 1, mRNA (cDNA clone MGC: 12166 IMAGE: 3828551), complete cds | | |
| BC069491.1 | IOH40249 | Cerberus | AD | 0.025523 |
| NM_138559.1 | IOH43559 | B-cell CLL/lymphoma 11A (zinc finger protein) (BCL11A), transcript variant 3 | AD | 0.025523 |
| BC004376.1 | IOH5584 | annexin A8 (ANXA8L1) | AD | 0.025523 |
| NM_005620.1 | IOH4079 | S100 calcium binding protein A11 (S100A11) | AD | 0.025523 |

TABLE 7-continued

| Database ID | Ultimate ORF ID | Description | Indication | P-Value |
|---|---|---|---|---|
| PV3872 | | epidermal growth factor receptor (erythroblastic leukemia viral (v-erb-b) oncogene homolog, avian) (EGFR); see catalog number for detailed information on wild-type or point mutant status | AD | 0.025523 |
| NM_032214.1 | IOH26309 | Src-like-adaptor 2 (SLA2), transcript variant 1 | AD | 0.025523 |
| NM_002444.1 | IOH2457 | moesin (MSN) | AD | 0.025523 |
| NM_173796.2 | IOH23049 | hypothetical protein MGC24125 (MGC24125) | AD | 0.025523 |
| NM_002648.1 | | pim-1 oncogene (PIM1) | AD | 0.025523 |
| NM_001876.2 | IOH52786 | Carnitine O-palmitoyltransferase 1, liver isoform | AD | 0.025523 |
| BC014532.1 | IOH12798 | decapping enzyme, scavenger (DCPS) | AD | 0.025523 |
| NM_001005266.1 | IOH59477 | Dresden prostate carcinoma protein 2 | AD | 0.025523 |
| NM_007172.2 | IOH40805 | nucleoporin 50 kDa (NUP50), transcript variant 2 | AD | 0.025523 |
| NM_018326.1 | IOH14251 | GTPase, IMAP family member 4 (GIMAP4) | AD | 0.025523 |
| BC033881.1 | IOH22099 | XRCC6 binding protein 1 (XRCC6BP1) | AD | 0.025523 |
| NM_020168.3 | IOH20961 | p21(CDKN1A)-activated kinase 6 (PAK6) | AD | 0.025523 |
| NM_014790.3 | IOH14698 | janus kinase and microtubule interacting protein 2 (JAKMIP2) | AD | 0.025562 |
| NM_032360.1 | IOH6003 | acyl-Coenzyme A binding domain containing 6 (ACBD6) | AD | 0.025562 |
| NM_006303.2 | IOH5395 | JTV1 gene (JTV1) | AD | 0.025562 |
| BC017305.1 | IOH12450 | sirtuin (silent mating type information regulation 2 homolog) 7 (*S. cerevisiae*) (SIRT7) | AD | 0.025562 |
| BC051762.1 | IOH28838 | Uncharacterized protein C20orf96 | AD | 0.025562 |
| NM_145010.1 | IOH10871 | chromosome 10 open reading frame 63 (C10orf63) | AD | 0.025589 |
| NM_206834.1 | IOH40081 | Uncharacterized protein C6orf201 | AD | 0.027186 |
| BC009350.1 | IOH14087 | Eukaryotic translation initiation factor 2-alpha kinase 4 | AD | 0.027186 |
| NM_003720.1 | IOH3819 | Proteasome assembly chaperone 1 | AD | 0.027186 |
| NM_001906.1 | IOH7194 | chymotrypsinogen B1 (CTRB1) | Control | 0.027437 |
| BC037900.2 | IOH27758 | C-terminal binding protein 2 (CTBP2) | Control | 0.027437 |
| NM_138960.3 | IOH59763 | Homeobox protein TGIF2LX | Control | 0.027437 |
| BC067755.1 | IOH40120 | potassium channel tetramerisation domain containing 18 (KCTD18) | AD | 0.027437 |
| BC005840.2 | IOH46093 | selenoprotein S (SELS) | AD | 0.027437 |
| BC000934.2 | IOH2996 | eukaryotic translation initiation factor 2, subunit 2 beta, 38 kDa (EIF2S2) | AD | 0.027601 |
| BC038838.1 | IOH28760 | Proline-rich protein 16 | Control | 0.027601 |
| NM_020175.1 | IOH13452 | dihydrouridine synthase 3-like (*S. cerevisiae*) (DUS3L) | AD | 0.027808 |
| BC002695.1 | IOH5262 | AP2 associated kinase 1 (AAK1) | Control | 0.028183 |
| NM_032472.3 | IOH44558 | Peptidyl-prolyl cis-trans isomerase-like 3 | Control | 0.028183 |
| NM_016185.1 | IOH4078 | hematological and neurological expressed 1 (HN1), transcript variant 1 | Control | 0.028183 |
| BC032372.1 | IOH21643 | Ral GEF with PH domain and SH3 binding motif 1 (RALGPS1) | Control | 0.028183 |
| NM_002994.2 | IOH7295 | chemokine (C-X-C motif) ligand 5 (CXCL5) | Control | 0.028183 |
| NM_176783.1 | IOH40962 | proteasome (prosome, macropain) activator subunit 1 (PA28 alpha) (PSME1), transcript variant 2 | Control | 0.028183 |
| BC053872.1 | IOH28961 | copine V (CPNE5) | Control | 0.028183 |
| BC017236.1 | IOH14401 | Casein kinase I isoform gamma-1 | Control | 0.028183 |
| BC014667.1 | IOH14303 | immunoglobulin heavy constant gamma 1 (G1m marker) (IGHG1) | AD | 0.028183 |
| NM_201403.1 | IOH42184 | MOB1, Mps One Binder kinase activator-like 2C (yeast) (MOBKL2C), transcript variant 2 | AD | 0.028996 |
| NM_006640.2 | IOH12164 | septin 9 (SEPT9) | Control | 0.028996 |
| BC010537.1 | IOH10170 | SUB1 homolog (*S. cerevisiae*) (SUB1) | AD | 0.029607 |

TABLE 7-continued

| Database ID | Ultimate ORF ID | Description | Indication | P-Value |
|---|---|---|---|---|
| NM_170746.2 | IOH58679 | Selenoprotein H | AD | 0.029607 |
| NM_031296.1 | IOH43454 | RAB33B, member RAS oncogene family (RAB33B) | Control | 0.030052 |
| NM_032459.1 | IOH21413 | embryonal Fyn-associated substrate (EFS), transcript variant 2 | Control | 0.030431 |
| NM_003092.3 | IOH21977 | small nuclear ribonucleoprotein polypeptide B" (SNRPB2), transcript variant 1 | AD | 0.030431 |
| NM_005105.2 | IOH10383 | RNA binding motif protein 8A (RBM8A) | AD | 0.030921 |
| BC022571.1 | IOH22219 | prune homolog 2 (*Drosophila*) (PRUNE2) | Control | 0.031626 |
| NM_002714.2 | IOH39632 | protein phosphatase 1, regulatory (inhibitor) subunit 10 (PPP1R10) | Control | 0.031794 |
| NM_153450.1 | IOH27352 | mediator complex subunit 19 (MED19) | Control | 0.031794 |
| BC104468.1 | IOH63630 | Outer dense fiber protein 3-like protein 2 | Control | 0.031794 |
| BC047411.1 | IOH26516 | tubulin tyrosine ligase-like family, member 2 (TTLL2) | AD | 0.031794 |
| NM_199188.1 | IOH38224 | La ribonucleoprotein domain family, member 4 (LARP4), transcript variant 2 | AD | 0.031794 |
| BC003551.1 | IOH4964 | transglutaminase 2 (C polypeptide, protein-glutamine-gamma-glutamyltransferase) (TGM2) | AD | 0.032518 |
| BC020647.1 | IOH12765 | coiled-coil domain containing 59 (CCDC59) | AD | 0.032518 |
| BC048301.1 | IOH26612 | zinc finger, CCHC domain containing 11 (ZCCHC11) | Control | 0.032529 |
| BC011781.2 | IOH13131 | chromosome 9 open reading frame 37 (C9orf37) | AD | 0.032529 |
| NM_001033551.1 | IOH26533 | TOM1-like protein 2 | Control | 0.032802 |
| NM_177973.1 | IOH22150 | sulfotransferase family, cytosolic, 2B, member 1 (SULT2B1), transcript variant 2 | Control | 0.032802 |
| NM_006907.2 | IOH59071 | Pyrroline-5-carboxylate reductase 1, mitochondrial | Control | 0.032802 |
| NM_032858.1 | IOH12001 | maelstrom homolog (*Drosophila*) (MAEL) | AD | 0.033103 |
| NM_144971.1 | IOH10719 | hypothetical protein MGC26641 (MGC26641) | AD | 0.033103 |
| BC017440.1 | IOH14659 | trafficking protein particle complex 2-like (TRAPPC2L) | AD | 0.033103 |
| BC017018.1 | IOH11265 | DnaJ (Hsp40) homolog, subfamily C, member 12 (DNAJC12) | AD | 0.033103 |
| NM_144767.3 | IOH44040 | A kinase (PRKA) anchor protein 13 (AKAP13), transcript variant 3 | AD | 0.033103 |
| NM_018297.2 | IOH6809 | N-glycanase 1 (NGLY1) | AD | 0.033103 |
| NM_031845.1 | IOH37776 | microtubule-associated protein 2 (MAP2), transcript variant 2 | Control | 0.033103 |
| NM_002307.1 | IOH40009 | lectin, galactoside-binding, soluble, 7 (galectin 7) (LGALS7) | AD | 0.03362 |
| NM_003939.2 | IOH42069 | beta-transducin repeat containing (BTRC), transcript variant 2, mRNA. | AD | 0.03362 |
| NM_013242.1 | IOH5166 | chromosome 16 open reading frame 80 (C16orf80) | AD | 0.03362 |
| NM_152285.1 | IOH21698 | arrestin domain containing 1 (ARRDC1) | AD | 0.033955 |
| NM_178425.1 | IOH38634 | histone deacetylase 9 (HDAC9), transcript variant 5 | AD | 0.033955 |
| NM_007255.1 | IOH5828 | xylosylprotein beta 1,4-galactosyltransferase, polypeptide 7 (galactosyltransferase I) (B4GALT7) | AD | 0.033955 |
| NM_205833.1 | IOH41224 | immunoglobulin superfamily, member 1 (IGSF1), transcript variant 2 | AD | 0.033955 |
| BC040457.1 | IOH26807 | calcium/calmodulin-dependent protein kinase (CaM kinase) II alpha (CAMK2A) | AD | 0.033955 |
| NM_004732.1 | IOH29581 | potassium voltage-gated channel, shaker-related subfamily, beta member 3 (KCNAB3) | AD | 0.033955 |
| NM_004450.1 | IOH14288 | enhancer of rudimentary homolog (*Drosophila*) (ERH) | AD | 0.033955 |

TABLE 7-continued

| Database ID | Ultimate ORF ID | Description | Indication | P-Value |
|---|---|---|---|---|
| XM_378582.2 | IOH43485 | PREDICTED: Homo sapiens hypothetical LOC400523 (LOC400523) | AD | 0.033955 |
| NM_001006666.1 | IOH58588 | apolipoprotein B mRNA editing enzyme, catalytic polypeptide-like 3F (APOBEC3F), transcript variant 2, mRNA. | AD | 0.033955 |
| BC041876.1 | IOH27738 | tau tubulin kinase 2 (TTBK2) | AD | 0.033955 |
| BC036335.1 | IOH25781 | BTB (POZ) domain containing 12 (BTBD12) | AD | 0.033955 |
| BC036099.1 | IOH27225 | aryl-hydrocarbon receptor nuclear translocator 2 (ARNT2) | AD | 0.033955 |
| NM_054012.1 | IOH14007 | argininosuccinate synthetase 1 (ASS1), transcript variant 2 | AD | 0.033955 |
| NM_057749.1 | IOH43526 | cyclin E2 (CCNE2) | AD | 0.033955 |
| PV3839 | | CDC-like kinase 4 (CLK4) | AD | 0.033955 |
| BC005026.1 | IOH6532 | sirtuin (silent mating type information regulation 2 homolog) 6 (S. cerevisiae) (SIRT6) | AD | 0.033955 |
| NM_013975.1 | IOH40893 | ligase III, DNA, ATP-dependent (LIG3), nuclear gene encoding mitochondrial protein, transcript variant alpha | AD | 0.033955 |
| NM_181509.1 | IOH42908 | microtubule-associated protein 1 light chain 3 alpha (MAP1LC3A), transcript variant 2 | AD | 0.033955 |
| BC001709.1 | IOH4911 | NAD kinase (NADK) | AD | 0.033955 |
| NM_002638.1 | IOH13658 | peptidase inhibitor 3, skin-derived (SKALP) (PI3) | AD | 0.033955 |
| NM_005901.2 | IOH22138 | SMAD family member 2 (SMAD2), transcript variant 1 | AD | 0.033955 |
| BC046199.1 | IOH26969 | family with sequence similarity 72, member B (FAM72B) | AD | 0.033955 |
| NM_015417.2 | IOH11253 | sperm flagellar 1 (SPEF1) | AD | 0.033955 |
| NM_018328.1 | IOH12893 | methyl-CpG binding domain protein 5 (MBD5) | AD | 0.033955 |
| BC017328.2 | IOH14721 | angiotensin II receptor-associated protein (AGTRAP) | AD | 0.033955 |
| NM_182739.1 | IOH44393 | NADH dehydrogenase (ubiquinone) 1 beta subcomplex, 6, 17 kDa (NDUFB6), nuclear gene encoding mitochondrial protein, transcript variant 2 | AD | 0.033955 |
| NM_001032293.1 | IOH3584 | zinc finger protein 207 (ZNF207), transcript variant 2 | AD | 0.033955 |
| NM_012227.1 | IOH57121 | Putative GTP-binding protein 6 | AD | 0.033955 |
| BC026039.1 | IOH40656 | mitochondrial GTPase 1 homolog (S. cerevisiae) (MTG1) | AD | 0.033955 |
| BC072409.1 | IOH62546 | Serine/threonine-protein phosphatase 4 regulatory subunit 3A | AD | 0.033955 |
| BC066938.1 | IOH40083 | DEAD (Asp-Glu-Ala-Asp) box polypeptide 43 (DDX43) | AD | 0.034253 |
| BC000712.1 | IOH4703 | kinesin family member C1 (KIFC1) | AD | 0.034253 |
| BC000052.1 | IOH4650 | peroxisome proliferator-activated receptor alpha (PPARA) | AD | 0.035152 |
| NM_199124.1 | IOH43439 | chromosome 11 open reading frame 63 (C11orf63), transcript variant 2 | Control | 0.035152 |
| NM_004117.2 | IOH27424 | FK506 binding protein 5 (FKBP5) | AD | 0.035152 |
| NM_002629.2 | IOH13682 | phosphoglycerate mutase 1 (brain) (PGAM1) | AD | 0.035152 |
| NM_015122.1 | IOH26137 | FCH domain only 1 (FCHO1) | AD | 0.035152 |
| NM_001021.2 | IOH27847 | ribosomal protein S17 (RPS17) | AD | 0.035152 |
| NM_013323.1 | IOH3822 | sorting nexin 11 (SNX11), transcript variant 2 | AD | 0.035152 |
| BC002950.1 | IOH46164 | chromosome 18 open reading frame 8 (C18orf8) | AD | 0.035152 |
| NM_017612.1 | IOH11180 | Zinc finger CCHC domain-containing protein 8 | AD | 0.035152 |
| BC035048.2 | IOH27687 | neurogenic differentiation 6 (NEUROD6) | AD | 0.035152 |
| BC046117.1 | IOH26985 | dynein, axonemal, light intermediate chain 1 (DNALI1) | AD | 0.035152 |
| NM_005335.3 | IOH57089 | Hematopoietic lineage cell-specific protein | AD | 0.035152 |

TABLE 7-continued

| Database ID | Ultimate ORF ID | Description | Indication | P-Value |
|---|---|---|---|---|
| NM_144679.1 | IOH40679 | chromosome 17 open reading frame 56 (C17orf56) | AD | 0.035152 |
| NM_004881.1 | IOH3658 | tumor protein p53 inducible protein 3 (TP53I3), transcript variant 1 | AD | 0.035152 |
| NM_006442.2 | IOH14520 | DR1-associated protein 1 (negative cofactor 2 alpha) (DRAP1) | Control | 0.035766 |
| BC047733.1 | IOH26736 | tRNA aspartic acid methyltransferase 1 (TRDMT1) | Control | 0.035766 |
| NM_033122.1 | IOH26918 | chromosome 4 open reading frame 35 (C4orf35) | Control | 0.035766 |
| NM_080423.1 | IOH23012 | protein tyrosine phosphatase, non-receptor type 2 (PTPN2), transcript variant 3 | Control | 0.035766 |
| BC015665.2 | IOH40642 | LATS, large tumor suppressor, homolog 1 (*Drosophila*) (LATS1) | Control | 0.035766 |
| BC001716.1 | IOH4447 | poly(A) binding protein interacting protein 2 (PAIP2) | Control | 0.035766 |
| NM_138316.2 | IOH59336 | Pantothenate kinase 1 | Control | 0.035766 |
| NM_005900.1 | IOH4970 | SMAD family member 1 (SMAD1), transcript variant 1 | Control | 0.035766 |
| BC039337.1 | IOH62273 | Polyadenylate-binding protein-interacting protein 2 | Control | 0.035766 |
| NM_001950.3 | IOH23241 | E2F transcription factor 4, p107/p130-binding (E2F4) | Control | 0.035766 |
| BC008819.1 | IOH6323 | nuclear receptor subfamily 1, group H, member 3 (NR1H3) | Control | 0.035766 |
| NM_024818.1 | IOH9860 | ubiquitin-activating enzyme E1-domain containing 1 (UBE1DC1), transcript variant 1 | Control | 0.035766 |
| NM_004838.2 | IOH12410 | homer homolog 3 (*Drosophila*) (HOMER3) | Control | 0.035766 |
| NM_012419.3 | IOH11052 | regulator of G-protein signaling 17 (RGS17) | Control | 0.035766 |
| BC042999.2 | IOH25869 | Putative Polycomb group protein ASXL2 | Control | 0.035766 |
| NM_005441.2 | IOH13577 | chromatin assembly factor 1, subunit B (p60) (CHAF1B) | Control | 0.035766 |
| BC009055.1 | IOH3376 | Protein FAM184A | Control | 0.035766 |
| BC006818.1 | IOH3186 | 1-acylglycerol-3-phosphate O-acyltransferase 1 (lysophosphatidic acid acyltransferase, alpha), mRNA (cDNA clone IMAGE: 3448169), complete cds. | Control | 0.035766 |
| BC053509.1 | IOH29394 | 5,10-methylenetetrahydrofolate reductase (NADPH) (MTHFR) | Control | 0.035766 |
| BC051888.1 | IOH27068 | tRNA-yW synthesizing protein 1 homolog (*S. cerevisiae*) (TYW1) | Control | 0.035766 |
| NM_001952.2 | IOH6989 | E2F transcription factor 6 (E2F6) | Control | 0.035766 |
| PV3871 | | dual-specificity tyrosine-(Y)-phosphorylation regulated kinase 4 (DYRK4) | Control | 0.035766 |
| BC012746.1 | IOH14565 | mesoderm development candidate 2 (MESDC2) | Control | 0.035766 |
| NM_003341.3 | IOH43236 | Ubiquitin-conjugating enzyme E2 E1 | Control | 0.035766 |
| NM_138499.2 | IOH40143 | PWWP domain-containing protein 2B | Control | 0.035766 |
| NM_032051.1 | IOH13231 | POZ (BTB) and AT hook containing zinc finger 1 (PATZ1), transcript variant 4 | Control | 0.035766 |
| BC007565.1 | IOH6820 | phospholipase C, gamma 2 (phosphatidylinositol-specific) (PLCG2) | Control | 0.035766 |
| NM_022083.1 | IOH45531 | Protein Niban | Control | 0.035766 |
| NM_052940.3 | IOH10671 | leucine rich repeat containing 42 (LRRC42) | Control | 0.035766 |
| BC044884.1 | IOH26494 | KIAA0265 protein (KIAA0265) | Control | 0.035766 |
| BC000452.1 | IOH3518 | peroxiredoxin 2 (PRDX2) | Control | 0.035766 |
| NM_018246.1 | IOH40864 | coiled-coil domain containing 25 (CCDC25) | Control | 0.035766 |
| BC005033.1 | IOH6631 | actinin, alpha 4 (ACTN4) | Control | 0.035766 |
| BC000583.1 | IOH22887 | Thimet oligopeptidase | Control | 0.035766 |
| NM_006406.1 | IOH7551 | peroxiredoxin 4 (PRDX4) | Control | 0.035766 |

TABLE 7-continued

| Database ID | Ultimate ORF ID | Description | Indication | P-Value |
|---|---|---|---|---|
| BC034488.2 | IOH22312 | ATP-binding cassette, sub-family F (GCN20), member 1 (ABCF1) | Control | 0.035766 |
| BC020942.1 | IOH11137 | transmembrane protein 140 (TMEM140) | Control | 0.035766 |
| NM_003223.1 | IOH9646 | transcription factor AP-4 (activating enhancer binding protein 4) (TFAP4) | Control | 0.035766 |
| BC011863.2 | IOH14833 | DNA helicase HEL308 (HEL308) | Control | 0.035766 |
| NM_025057.1 | IOH35314 | chromosome 14 open reading frame 45 (C14orf45) | Control | 0.035766 |
| NM_031361.1 | IOH4674 | collagen, type IV, alpha 3 (Goodpasture antigen) binding protein (COL4A3BP), transcript variant 2 | Control | 0.035766 |
| NM_052965.1 | IOH56031 | tRNA-splicing endonuclease subunit Sen15 | Control | 0.035766 |
| NM_199334.2 | IOH6734 | thyroid hormone receptor, alpha (erythroblastic leukemia viral (v-erb-a) oncogene homolog, avian) (THRA), transcript variant 1 | AD | 0.037822 |
| NM_201567.1 | IOH37812 | cell division cycle 25 homolog A (S. pombe) (CDC25A), transcript variant 2 | AD | 0.037822 |
| BC012945.1 | IOH25802 | Uncharacterized protein C19orf57 | AD | 0.038115 |
| NM_005663.2 | IOH46152 | Wolf-Hirschhorn syndrome candidate 2 (WHSC2) | Control | 0.038115 |
| BC025266.1 | IOH23199 | taspase, threonine aspartase, 1 (TASP1) | Control | 0.038169 |
| NM_014487.2 | IOH4416 | zinc finger protein 330 (ZNF330) | Control | 0.038169 |
| NM_197957.2 | IOH41003 | MYC associated factor X (MAX), transcript variant 6 | Control | 0.038169 |
| NM_006695.2 | IOH5798 | RUN domain containing 3A (RUNDC3A) | Control | 0.038169 |
| NM_144594.1 | IOH10942 | family with sequence similarity 112, member B (FAM112B) | Control | 0.038169 |
| NM_032146.2 | IOH10608 | ADP-ribosylation factor-like 6 (ARL6), transcript variant 1 | Control | 0.038169 |
| BC014218.2 | IOH12802 | THAP domain-containing protein 3 | Control | 0.038169 |
| BC037845.1 | IOH62213 | Multiple coagulation factor deficiency protein 2 | Control | 0.038169 |
| BC043394.1 | IOH26350 | ankyrin repeat domain 17 (ANKRD17) | AD | 0.040087 |
| NM_053005.2 | IOH40119 | HCCA2 protein (HCCA2) | AD | 0.040087 |
| NM_175065.2 | IOH35055 | histone cluster 2, H2ab (HIST2H2AB) | AD | 0.040087 |
| NM_004706.3 | IOH45526 | Rho guanine nucleotide exchange factor (GEF) 1 (ARHGEF1), transcript variant 2 | AD | 0.040087 |
| NM_014346.1 | IOH22792 | TBC1 domain family, member 22A (TBC1D22A) | AD | 0.040087 |
| NM_133480.1 | IOH13139 | transcriptional adaptor 3 (NGG1 homolog, yeast)-like (TADA3L), transcript variant 2 | AD | 0.040118 |
| BC002448.2 | IOH4300 | actin binding LIM protein 1 (ABLIM1) | Control | 0.041317 |
| BC048969.1 | IOH26897 | TSPY-like 1 (TSPYL1) | AD | 0.041317 |
| NM_020319.1 | IOH27320 | ankyrin repeat and MYND domain containing 2 (ANKMY2) | AD | 0.041317 |
| NM_016046.2 | IOH11580 | exosome component 1 (EXOSC1) | AD | 0.042299 |
| NM_001003396.1 | IOH3597 | tumor protein D52-like 1 (TPD52L1), transcript variant 3 | AD | 0.042315 |
| NM_005870.3 | IOH53845 | Histone deacetylase complex subunit SAP18 | AD | 0.042315 |
| NM_003403.3 | IOH27684 | YY1 transcription factor (YY1) | AD | 0.042315 |
| BC036096.2 | IOH27280 | zinc finger protein 18 (ZNF18) | AD | 0.042315 |
| NM_001010844.1 | IOH43230 | Interleukin-1 receptor-associated kinase 1-binding protein 1 | AD | 0.043024 |
| BC029524.1 | IOH22562 | Coiled-coil domain-containing protein 46 | AD | 0.04393 |
| NM_005884.2 | IOH2475 | p21(CDKN1A)-activated kinase 4 (PAK4), transcript variant 1 | Control | 0.04393 |
| NM_033642.1 | IOH36760 | fibroblast growth factor 13 (FGF13), transcript variant 1B | Control | 0.045355 |
| BC058900.1 | IOH29076 | rabaptin, RAB GTPase binding effector protein 2 (RABEP2) | Control | 0.045355 |
| BC015239.1 | IOH10789 | zinc finger and BTB domain containing 8 (ZBTB8) | Control | 0.045355 |

TABLE 7-continued

| Database ID | Ultimate ORF ID | Description | Indication | P-Value |
|---|---|---|---|---|
| NM_001005339.1 | IOH13018 | regulator of G-protein signaling 10 (RGS10), transcript variant 1 | Control | 0.045355 |
| NM_006819.1 | IOH5061 | stress-induced-phosphoprotein 1 (Hsp70/Hsp90-organizing protein) (STIP1) | Control | 0.045355 |
| NM_152387.2 | IOH53987 | BTB/POZ domain-containing protein KCTD18 | AD | 0.045355 |
| BC002369.1 | | Serine/threonine-protein kinase PLK1 | AD | 0.045355 |
| BC092404.1 | IOH62574 | Rap guanine nucleotide exchange factor 3 | AD | 0.045786 |
| NM_004922.2 | IOH38664 | SEC24 related gene family, member C (S. cerevisiae) (SEC24C), transcript variant 1 | AD | 0.046722 |
| NM_198217.1 | IOH59743 | Inhibitor of growth protein 1 | AD | 0.046722 |
| BC051911.1 | IOH27047 | chromosome 13 open reading frame 24 (C13orf24) | AD | 0.046722 |
| NM_006205.1 | IOH40356 | phosphodiesterase 6H, cGMP-specific, cone, gamma (PDE6H) | AD | 0.046722 |
| NM_024790.2 | IOH13277 | centrosome and spindle pole associated protein 1 (CSPP1), transcript variant 2 | Control | 0.046828 |
| NM_006439.3 | IOH12221 | Protein mab-21-like 2 | AD | 0.046828 |
| NM_173456.1 | IOH45493 | phosphodiesterase 8A (PDE8A), transcript variant 4 | AD | 0.048209 |
| BC019268.1 | IOH13177 | Protein arginine N-methyltransferase 1 | AD | 0.048209 |
| NM_173642.1 | IOH26158 | family with sequence similarity 80, member A (FAM80A) | AD | 0.048209 |
| NM_194299.1 | IOH35431 | Synaptonemal complex protein 2-like | AD | 0.048209 |
| BC062323.1 | IOH40678 | chromosome 21 open reading frame 25 (C21orf25) | AD | 0.048209 |
| NM_021709.1 | IOH21450 | Apoptosis regulatory protein Siva | AD | 0.048209 |
| BC100813.1 | IOH63506 | Putative T-complex protein 1 subunit theta-like 2 | AD | 0.048209 |
| BC026317.1 | IOH11060 | solute carrier family 16, member 1 (monocarboxylic acid transporter 1) (SLC16A1) | AD | 0.048209 |
| BC010956.1 | IOH13684 | Keratinocyte growth factor | AD | 0.048209 |
| NM_005034.2 | IOH10479 | polymerase (RNA) II (DNA directed) polypeptide K, 7.0 kDa (POLR2K) | AD | 0.048209 |
| BC024291.1 | IOH14775 | BR serine/threonine kinase 2 (BRSK2) | AD | 0.048209 |
| NM_001001568.1 | IOH53504 | phosphodiesterase 9A (PDE9A), transcript variant 3, mRNA. | AD | 0.048209 |
| NM_014314.3 | IOH52971 | Probable ATP-dependent RNA helicase DDX58 | AD | 0.048209 |
| BC047420.1 | IOH26512 | UBX domain-containing protein 7 | AD | 0.048209 |
| NM_000430.2 | IOH39940 | platelet-activating factor acetylhydrolase, isoform Ib, alpha subunit 45 kDa (PAFAH1B1) | AD | 0.048209 |
| PV3873 | | epidermal growth factor receptor (erythroblastic leukemia viral (v-erb-b) oncogene homolog, avian) (EGFR); see catalog number for detailed information on wild-type or point mutant status | AD | 0.048209 |
| NM_001328.1 | IOH12818 | C-terminal binding protein 1 (CTBP1), transcript variant 1 | AD | 0.048209 |
| NM_001009959.1 | IOH43447 | Ermin | AD | 0.048209 |
| BC050387.1 | IOH26653 | ankyrin repeat and sterile alpha motif domain containing 3 (ANKS3) | AD | 0.048209 |
| NM_007194.1 | | Serine/threonine-protein kinase Chk2 | AD | 0.048209 |
| NM_018492.2 | IOH12390 | PDZ binding kinase (PBK) | AD | 0.048209 |
| NM_182801.1 | IOH23237 | EGF-like, fibronectin type III and laminin G domains (EGFLAM), transcript variant 4 | AD | 0.048209 |
| BC016615.1 | IOH10688 | RAB37, member RAS oncogene family (RAB37) | AD | 0.048209 |
| BC008950.2 | IOH56909 | Prenylated Rab acceptor protein 1 | AD | 0.048209 |
| BC041831.1 | IOH27713 | transducin-like enhancer of split 3 (E(sp1) homolog, Drosophila) (TLE3) | AD | 0.048209 |

TABLE 7-continued

| Database ID | Ultimate ORF ID | Description | Indication | P-Value |
|---|---|---|---|---|
| NM_003104.2 | IOH14671 | sorbitol dehydrogenase (SORD) | AD | 0.048209 |
| BC003555.1 | IOH4980 | nucleolar complex associated 2 homolog (S. cerevisiae) (NOC2L) | AD | 0.048209 |
| NM_001274.2 | | CHK1 checkpoint homolog (S. pombe) (CHEK1) | AD | 0.048209 |
| NM_153645.1 | IOH11663 | nucleoporin 50 kDa (NUP50), transcript variant 3 | AD | 0.048209 |
| BC017423.1 | IOH12806 | mesoderm induction early response 1 homolog (Xenopus laevis) (MIER1) | AD | 0.048209 |
| BC007424.2 | IOH6160 | PRP4 pre-mRNA processing factor 4 homolog (yeast) (PRPF4) | AD | 0.048209 |
| NM_007107.2 | IOH13133 | signal sequence receptor, gamma (translocon-associated protein gamma) (SSR3) | AD | 0.048209 |
| XM_096472.2 | IOH42996 | hypothetical LOC143678 (LOC143678) | AD | 0.048209 |
| NM_015698.2 | IOH3563 | G patch domain and KOW motifs (GPKOW) | AD | 0.048209 |
| NM_018111.1 | IOH57283 | Putative uncharacterized protein FLJ10490 | AD | 0.048209 |
| NM_006694.1 | IOH2941 | jumping translocation breakpoint (JTB) | AD | 0.048209 |
| NM_000045.2 | IOH14233 | arginase, liver (ARG1) | AD | 0.048209 |
| BC074765.2 | IOH59064 | POU domain, class 6, transcription factor 1 | AD | 0.048209 |
| NM_172028.1 | IOH42497 | ankyrin repeat and BTB (POZ) domain containing 1 (ABTB1), transcript variant 3 | AD | 0.048209 |
| BC026345.1 | IOH10790 | Ermin | AD | 0.048209 |
| NM_201262.1 | IOH41260 | DnaJ (Hsp40) homolog, subfamily C, member 12 (DNAJC12), transcript variant 2 | AD | 0.048209 |
| NM_002966.1 | IOH14651 | S100 calcium binding protein A10 (S100A10) | AD | 0.048209 |
| BC013352.1 | IOH14736 | HpaII tiny fragments locus 9c protein | AD | 0.048209 |
| NM_004873.1 | IOH26366 | BCL2-associated athanogene 5 (BAG5), transcript variant 2 | AD | 0.048209 |
| BC009415.1 | IOH14115 | kinesin family member 26A (KIF26A) | AD | 0.048209 |
| BC012539.1 | IOH12758 | mediator complex subunit 31 (MED31) | AD | 0.048209 |
| BC021247.1 | IOH22996 | Phosphatase and actin regulator 4 | AD | 0.048209 |
| NM_004414.3 | IOH5722 | regulator of calcineurin 1 (RCAN1), transcript variant 1 | AD | 0.048209 |
| BC028840.1 | IOH13887 | ankyrin repeat domain 13C (ANKRD13C) | AD | 0.048209 |
| BC025787.1 | IOH12000 | alkB, alkylation repair homolog 1 (E. coli) (ALKBH1) | AD | 0.048209 |
| NM_000459.1 | | Angiopoietin-1 receptor | AD | 0.048209 |
| NM_000788.1 | IOH42066 | Deoxycytidine kinase | AD | 0.048209 |
| NM_173859.1 | IOH35196 | breast cancer and salivary gland expression gene (RP11-49G10.8) | AD | 0.048209 |
| NM_152382.1 | IOH39899 | JmjC domain-containing protein C2orf60 | AD | 0.048209 |
| NM_002038.2 | IOH14517 | interferon, alpha-inducible protein 6 (IFI6), transcript variant 1 | AD | 0.048209 |
| BC034984.1 | IOH26875 | Kinesin-like protein KIF16B | AD | 0.048209 |
| NM_014582.1 | IOH40248 | odorant binding protein 2A (OBP2A) | AD | 0.048209 |
| BC057760.1 | IOH29220 | MORN repeat-containing protein 3 | AD | 0.048209 |
| NM_005595.1 | IOH12791 | nuclear factor I/A (NFIA) | AD | 0.048209 |
| NM_032726.1 | IOH21106 | phospholipase C, delta 4 (PLCD4) | AD | 0.048209 |
| NM_153276.1 | IOH21851 | solute carrier family 22 (organic anion transporter), member 6 (SLC22A6), transcript variant 2 | AD | 0.048209 |
| NM_001011538.1 | IOH39826 | similar to 60S ribosomal protein L21 (LOC402176) | AD | 0.048209 |
| NM_006433.2 | IOH27865 | granulysin (GNLY), transcript variant NKG5 | AD | 0.048209 |
| NM_024800.1 | | Serine/threonine-protein kinase Nek11 | AD | 0.048209 |
| NM_015850.2 | | Basic fibroblast growth factor receptor 1 | AD | 0.048209 |
| NM_006590.2 | IOH45672 | ubiquitin specific peptidase 39 (USP39) | AD | 0.048209 |

TABLE 7-continued

| Database ID | Ultimate ORF ID | Description | Indication | P-Value |
|---|---|---|---|---|
| NM_199054.1 | IOH37765 | MAP kinase interacting serine/threonine kinase 2 (MKNK2), transcript variant 2 | AD | 0.048209 |
| BC050696.1 | IOH27004 | chromosome 12 open reading frame 48 (C12orf48) | AD | 0.048209 |
| NM_024563.1 | IOH23059 | chromosome 5 open reading frame 23 (C5orf23) | AD | 0.048209 |
| NM_004832.1 | IOH4381 | glutathione S-transferase omega 1 (GSTO1) | AD | 0.048209 |
| NM_003242.2 | | transforming growth factor, beta receptor II (70/80 kDa) (TGFBR2), transcript variant 2 | AD | 0.048209 |
| BC050444.1 | IOH26738 | golgi autoantigen, golgin subfamily a, 4 (GOLGA4) | AD | 0.048209 |
| NM_201259.1 | IOH45586 | Mitochondrial import inner membrane translocase subunit TIM14 | AD | 0.048209 |
| NM_032124.3 | IOH27146 | haloacid dehalogenase-like hydrolase domain containing 2 (HDHD2) | AD | 0.048209 |
| NM_002870.1 | IOH3059 | RAB13, member RAS oncogene family (RAB13) | AD | 0.048209 |
| BC000337.2 | IOH3577 | glucose-6-phosphate dehydrogenase (G6PD) | AD | 0.048209 |
| BC060785.1 | IOH29158 | tripartite motif-containing 40 (TRIM40) | AD | 0.048209 |
| BC030597.1 | IOH22318 | ATR interacting protein (TREX1) | AD | 0.048209 |
| BC050551.1 | IOH26948 | BCL2-associated athanogene 5 (BAG5) | AD | 0.048209 |
| NM_004697.3 | IOH12861 | PRP4 pre-mRNA processing factor 4 homolog (yeast) (PRPF4) | AD | 0.048209 |
| NM_020990.2 | IOH5022 | creatine kinase, mitochondrial 1B (CKMT1B), nuclear gene encoding mitochondrial protein | AD | 0.048209 |
| BC039742.1 | IOH26173 | poly(rC) binding protein 1 (PCBP1) | AD | 0.048209 |
| BC021573.1 | IOH14848 | GTP-binding protein 10 | AD | 0.048209 |
| NM_015068.1 | IOH27074 | paternally expressed 10 (PEG10), transcript variant 1 | AD | 0.048209 |
| NM_001827.1 | IOH5978 | CDC28 protein kinase regulatory subunit 2 (CKS2) | AD | 0.048209 |
| NM_152876.1 | IOH50154 | Tumor necrosis factor receptor superfamily member 6 | AD | 0.048209 |
| BC015548.1 | IOH10351 | RAB3A interacting protein (rabin3) (RAB3IP) | AD | 0.048209 |
| BC062359.1 | IOH40676 | chromosome 8 open reading frame 47 (C8orf47) | AD | 0.048209 |
| BC029424.1 | IOH23140 | Probable glutathione peroxidase 8 | AD | 0.048209 |
| NM_001786.2 | IOH14583 | cell division cycle 2, G1 to S and G2 to M (CDC2), transcript variant 1 | AD | 0.048209 |
| BC000870.1 | IOH3246 | TIMELESS interacting protein (TIPIN) | AD | 0.048209 |
| NM_004103.2 | | Protein tyrosine kinase 2 beta | AD | 0.048209 |
| BC022454.2 | IOH10977 | Transient receptor potential cation channel subfamily M member 3 | AD | 0.048209 |
| NM_024046.1 | IOH21132 | CaM kinase-like vesicle-associated (CAMKV) | AD | 0.048209 |
| BC040521.1 | IOH27477 | testis expressed 2 (TEX2) | AD | 0.048209 |
| BC003164.1 | IOH46140 | leukocyte receptor cluster (LRC) member 4 (LENG4) | AD | 0.048209 |
| NM_000402.2 | IOH2390 | Glucose-6-phosphate 1-dehydrogenase | AD | 0.048209 |
| BC069328.1 | IOH40255 | Bcl2 modifying factor (BMP) | AD | 0.048209 |
| BC063463.1 | IOH39865 | coenzyme Q3 homolog, methyltransferase (*S. cerevisiae*) (COQ3) | AD | 0.048209 |
| NM_000572.2 | IOH29878 | Interleukin-10 | AD | 0.048209 |
| NM_006374.2 | | serine/threonine kinase 25 (STE20 homolog, yeast) (STK25) | AD | 0.048209 |
| NM_017966.1 | IOH5829 | vacuolar protein sorting 37 homolog C (*S. cerevisiae*) (VPS37C) | AD | 0.048209 |
| BC052602.1 | IOH29373 | carbonic anhydrase XIII (CA13) | AD | 0.048209 |
| BC018063.1 | IOH10722 | potassium channel tetramerisation domain containing 4 (KCTD4) | AD | 0.048209 |

TABLE 7-continued

| Database ID | Ultimate ORF ID | Description | Indication | P-Value |
|---|---|---|---|---|
| NM_031305.1 | IOH38124 | Rho GTPase activating protein 24 (ARHGAP24), transcript variant 2 | AD | 0.048209 |
| BC056401.1 | IOH28794 | centaurin, delta 2 (CENTD2) | AD | 0.048209 |
| BC022459.1 | IOH11064 | sulfotransferase family 4A, member 1 (SULT4A1) | AD | 0.048209 |
| XM_373630.2 | IOH41531 | PREDICTED: *Homo sapiens* hypothetical protein LOC145842 (LOC145842) | AD | 0.048209 |
| P3049 | | v-abl Abelson murine leukemia viral oncogene homolog 1 (ABL1), transcript variant a; see catalog number for detailed information on wild-type or point mutant status | AD | 0.048209 |
| NM_153012.1 | IOH12147 | Tumor necrosis factor ligand superfamily member 12 | AD | 0.048209 |
| NM_018270.3 | IOH14702 | MRG-binding protein | AD | 0.048209 |
| BC010739.1 | IOH9887 | COP9 signalosome complex subunit 7b | AD | 0.048209 |
| NM_015002.2 | IOH42260 | F-box protein 21 (FBXO21), transcript variant 2 | AD | 0.048209 |
| BC000497.1 | | CaM kinase-like vesicle-associated protein | AD | 0.048209 |
| NM_001449.2 | IOH13860 | four and a half LIM domains 1 (FHL1) | AD | 0.048209 |
| BC065912.1 | IOH40442 | Tyrosine-protein kinase ABL2 | AD | 0.048209 |
| NM_153356.1 | IOH27369 | TBC1 domain family, member 21 (TBC1D21) | AD | 0.048209 |
| BC032382.1 | IOH21661 | similar to pleckstrin homology domain containing, family M (with RUN domain) member 1; adapter protein 162, mRNA, complete cds. | AD | 0.048209 |
| BC094800.1 | IOH62619 | Jouberin | AD | 0.048362 |
| NM_207035.1 | IOH41684 | UPF0471 protein C1orf63 homolog | Control | 0.048362 |
| NM_003897.2 | IOH6603 | immediate early response 3 (IER3) | AD | 0.048717 |
| NM_178821.1 | IOH22298 | WD repeat domain 69 (WDR69) | AD | 0.048717 |
| NM_198219.1 | IOH59467 | Inhibitor of growth protein 1 | AD | 0.048717 |
| NM_024805.1 | IOH13501 | chromosome 18 open reading frame 22 (C18orf22) | AD | 0.048717 |
| NM_001040633.1 | IOH61663 | protein kinase, AMP-activated, gamma 2 non-catalytic subunit (PRKAG2), transcript variant c, mRNA. | AD | 0.048717 |
| NM_130807.1 | IOH10112 | MOB1, Mps One Binder kinase activator-like 2A (yeast) (MOBKL2A) | AD | 0.049919 |
| BC008623.1 | IOH3309 | roundabout, axon guidance receptor, homolog 3 (*Drosophila*) (ROBO3) | AD | 0.049919 |
| NM_001004285.1 | IOH45460 | DNA fragmentation factor, 40 kDa, beta polypeptide (caspase-activated DNase) (DFFB), transcript variant 3 | AD | 0.049919 |
| BC011885.1 | IOH14206 | eukaryotic translation initiation factor 2A, 65 kDa (EIF2A) | AD | 0.049919 |

Using a small subset of the identified indicators, it was possible to diagnose AD with great efficiency. The twenty protein microarray fluorescence values depicted in Table 4 were used to classify blinded samples as either Alzheimer's or control. A threshold value was calculated for each diagnostic indicator using the following equation:

Diagnostic Threshold=[(Mean AD Fluorescence Value)−(Mean Control Fluorescence Value)/2]+(Mean Control Fluorescence Value)

A fluorescence value for any given diagnostic indicator over the threshold value for that indicator is scored as a positive result. Using the antigens from Table 4, greater than or equal to four positive results out of the possible twenty diagnostic indicators predicts with high accuracy that the sample is from an Alzheimer's Disease patient. Less than four positive results out of the possible twenty diagnostic indicators on Table 4 predicts with high accuracy that the sample is from a healthy Control. (See FIG. 1.) Initial results with this diagnostic logic were as follows:

Alzheimer's Disease (AD) vs. all Controls
(Using twenty biomarkers from Table 4)
(See FIG. 1)
N=90 (50 AD, 40 Control)
Overall Error Rate: 4.44%

| | Predicted | |
|---|---|---|
| True | AD | Control |
| AD | 50 | 4 |
| Control | 0 | 36 |
| Error Rate | 0.000 | 0.010 |

EXAMPLE 9

Diagnosis of Alzheimer's Disease

Twenty antibodies and their respective antigens were selected that were rated as highly significant by multiple statistical analysis programs (Prospector, PAM, Random Forest) and performed well in a single platform. The antibodies are listed in Table 8.

TABLE 8

Diagnostic Autoantibodies in Alzheimer's Disease

| Database ID #: | Name: | MW (kDa): | Indication: | Reactivity: |
|---|---|---|---|---|
| BC051695.1 | FRMD8 | 51.2 | Alzheimer's | ↑AD, ↓CON |
| NM_015833.1 | ADARB1 | 80.8 | Alzheimer's | ↑AD, ↓CON |
| NM_002305.2 | LGALS1 | 14.7 | Alzheimer's | ↑AD, ↓CON |
| NM_001641.2 | APEX1 | 35.6 | Alzheimer's | ↑AD, ↓CON |
| NM_024316.1 | LENG1 | 30.5 | Control | ↓AD, ↑CON |
| NM_014280.1 | DnaJ homolog subfamily C member 8 | 29.8 | Alzheimer's | ↑AD, ↓CON |
| PHC1244 | CCL19 | 11.0 | Alzheimer's | ↑AD, ↓CON |
| BC064984.1 | ASXL1 | 9.5 | Alzheimer's | ↑AD, ↓CON |
| NM_021104.1 | RPL41 | 3.4 | Alzheimer's | ↑AD, ↓CON |
| BC004236.2 | UBE2S | 23.9 | Alzheimer's | ↑AD, ↓CON |
| NM_012387.1 | PADI4 | 74.1 | Alzheimer's | ↑AD, ↓CON |
| NM_003384.1 | VRK1 | 45.5 | Alzheimer's | ↑AD, ↓CON |
| NM_004113.3 | FGF12 | 27.4 | Alzheimer's | ↑AD, ↓CON |
| BC021174.1 | Small EDRK-rich factor 1 | 12.4 | Alzheimer's | ↑AD, ↓CON |
| NM_001001794.1 | FAM116B | 66.5 | Alzheimer's | ↑AD, ↓CON |
| NM_032377.2 | ELOF1 | 9.5 | Alzheimer's | ↑AD, ↓CON |
| NM_024754.2 | PTCD2 | 43.9 | Alzheimer's | ↑AD, ↓CON |
| NM_000984.2 | RPL23A | 17.7 | Alzheimer's | ↑AD, ↓CON |
| NM_139016.2 | C20orf198 | | Alzheimer's | ↑AD, ↓CON |
| NM_024668.1 | ANKHD1 | 269.5 | Alzheimer's | ↑AD, ↓CON |

With these twenty biomarkers (listed in Table 4 and Table 8) and the simple diagnostic logic explained above, it was possible to differentiate Alzheimer's Disease serum samples from Control serum samples with over 95% efficiency.

It is also possible to accurately diagnose using only the four biomarkers from Table 3. Diagnostic efficiency for these diagnostic indicators was assessed for AD, low Mini-Mental Status Examination (MMSE) AD and high-MMSE AD. The results are shown below.

Alzheimer's Disease (AD) vs. all Controls
Random Forest:
N=90 (50 AD, 40 Control)
Overall Error Rate: 7.78%

| | Predicted | |
|---|---|---|
| True | AD | Control |
| AD | 48 | 5 |
| Control | 2 | 35 |
| Error Rate | 0.040 | 0.125 |

Predictive Analysis of Microarrays (PAM):
N=90 (50 AD, 40 Con)
Overall Error Rate: 7.8%

| | Predicted | |
|---|---|---|
| True | AD | Control |
| AD | 50 | 7 |
| Control | 0 | 33 |
| Error Rate | 0.000 | 0.175 |

Low-MMSE AD vs. all Controls
(Low-MMSE AD samples have MMSE<15)
Random Forest:
N=55 (15 Low-MMSE AD, 40 Control)
Overall Error Rate: 7.26%

| | Predicted | |
|---|---|---|
| True | AD | Control |
| AD | 13 | 2 |
| Control | 2 | 38 |
| Error Rate | 0.133 | 0.050 |

Predictive Analysis of Microarrays (PAM):
N=30 (15 Low-MMSE AD, 15 Control)
Overall Error Rate: 9.9%

| | Predicted | |
|---|---|---|
| True | AD | Control |
| AD | 13 | 1 |
| Control | 2 | 14 |
| Error Rate | 0.133 | 0.067 |

High-MMSE AD vs. all Controls
(High-MMSE AD samples have MMSE≥15)
Random Forest:
N=75 (35 High-MMSE AD, 40 Control)
Overall Error Rate: 10.67%

| | Predicted | |
|---|---|---|
| True | AD | Control |
| AD | 32 | 5 |
| Control | 3 | 35 |
| Error Rate | 0.086 | 0.125 |

Predictive Analysis of Microarrays (PAM):
N=70 (35 High-MMSE AD, 35 Control)
Overall Error Rate: 12.8%

| | Predicted | |
|---|---|---|
| True | AD | Control |
| AD | 28 | 2 |
| Control | 7 | 33 |
| Error Rate | 0.200 | 0.057 |

Using a combination of the biomarkers listed in Tables 3 and 5 (totaling nine diagnostic indicators), the efficiency of distinction between AD and Parkinson's Disease was also assessed. The results are shown below.
Alzheimer's Disease (AD) vs. Parkinson's Disease (PK)
Random Forest:
N=79 (29 AD, 29 PK)
Overall Error Rate: 12.07%

| | Predicted | |
|---|---|---|
| True | AD | PK |
| AD | 25 | 3 |
| PK | 4 | 26 |
| Error Rate | 0.138 | 0.103 |

Predictive Analysis of Microarrays (PAM):
N=58 (29 AD, 29 PK)
Overall Error Rate: 12.0%

| | Predicted | |
|---|---|---|
| True | AD | PK |
| AD | 24 | 2 |
| PK | 5 | 27 |
| Error Rate | 0.172 | 0.069 |

It was determined that it was possible to differentiate AD and control with over 95% accuracy using the twenty antigens from Table 4 and over 90% accuracy using the four antigens on Table 3, however, the use of only these four indicators did not allow accurate differentiation of Alzheimer's Disease from other neurodegenerative diseases like Parkinson's Disease. Accurate differentiation requires the inclusion of antigens from Table 5. In practice, however, this distinction is often unnecessary, since patients presenting with suspected Alzheimer's disease come with memory and cognitive deficits, whereas patients with early Parkinson's most often show tremors with no complaints of cognitive and/or memory deficits.

EXAMPLE 10

Diagnosis of Alzheimer's Disease

Ethics Statement
Approval for the use of blood samples for this study was obtained from the UMDNJ-Stratford Institutional Review Board.
Patient Samples
Serum samples from 50 AD subjects and 40 non-demented controls (NDC) were obtained from Analytical Biological Systems, Inc. (Wilmington, Del.). 30 breast cancer (BC) serum samples and 29 Parkinson's disease (PD) serum samples were obtained from Asterand, Inc. (Detroit, Mich.). To represent different disease stages reflecting disease severity, the AD serum pool contained samples with Mini-Mental State Examination (MMSE) scores ranging from 2-24. All samples were handled by standard procedures and stored at −80° C. Diagnosis of AD was based on a medical evaluation, neuropsychiatric testing, and on the National Institute of Neurological and Communicative Disorders and the Alzheimer's Disease and Related Disorders Association criteria. Demographic characteristics of the study population are shown in Table 9.

TABLE 9

Demographics of Serum Donors

| | | Age | | Sex | |
|---|---|---|---|---|---|
| Group | n | Mean | Range | (% male) | MMSE |
| Alzheimer's disease | 50 | 78.5 | 61-97 | 40% | 2-24 |
| Earlier-stage[1] | 35 | 78.7 | 61-97 | 43% | 15-24 |
| Later-stage[2] | 15 | 78.0 | 65-94 | 33% | 2-14 |
| Non-demented Controls | 40 | 40.4 | 19-86 | 82% | — |
| Older Control | 20 | 57.7 | 51-86 | 100% | — |
| Younger Control | 20 | 24.7 | 19-30 | 65% | — |
| Parkinson's disease | 29 | 74.0 | 53-88 | 55% | — |
| Breast Cancer | 30 | 46.7 | 32-54 | 0% | — |

[1]Earlier-stage: AD patients with MMSE ≥ 15
[2]Later-stage: AD patients with MMSE < 15

Human Protein Microarrays
To identify autoantibodies in human sera, Invitrogen's ProtoArray v5.0 Human Protein Microarrays (Cat. No. PAH0525020, Invitrogen, Carlsbad, Calif., USA), each containing 9,486 unique human protein antigens (www.invitrogen.com/protoarray) were used. All proteins had been expressed as GST fusion proteins in insect cells, purified under native conditions, and spotted in duplicate onto nitrocellulose-coated glass slides. All arrays were probed and scanned according to the manufacturer's instructions using commercially prepared reagents. Briefly, microarray slides were blocked (Blocking Buffer, Cat. No. PA055, Invitrogen) and then incubated with serum samples, diluted 1:500 in washing buffer. After washing, the arrays were probed with anti-human IgG (H+L) conjugated to AlexaFluor 647 (Cat. No. A-21445, Invitrogen). Arrays were then washed, dried, and immediately scanned with a GenePix 4000B Fluorescence Scanner (Molecular Devices, Sunnyvale, Calif., USA).
Dot Blot Analysis
One μl volumes of purified recombinant human FRMD8 (0.2 μg/μl) and PTCD2 (0.1 μg/μl) proteins (Cat. No. TP307879 and TP315253, OriGene Technologies, Inc., Rockville, Md., USA), were manually pipetted onto a nitrocellulose membrane. The proteins were blocked in a 5% non-fat milk PBS-Tween solution for one hour at room temperature (RT). The proteins were then probed with human serum samples diluted 1:2000 for one hour at RT. All sera were identical to those used to probe the human protein microarrays. The dot blots were probed with an anti-human IgG (H+L) HRP conjugate antibody (Cat. No. 31410, Thermo Fisher Scientific Inc., Pittsburgh, Pa., USA) for one hour at RT, incubated with ECL reagent (Cat. No. 34096, Thermo Fisher Scientific Inc., Pittsburgh, Pa., USA) for one minute, and then exposed to X-ray film at various intervals.
Data Analysis
The fluorescence data for each microarray was acquired by Genepix Pro analysis software after scanning, and then synced with Invitrogen's lot-specific Genepix Array List (GAL) files. The resulting Genepix Results (GPR) files were then imported into Invitrogen's Prospector 5.2 for analysis. All data was MIAME compliant and the raw data has been deposited in a MIAME compliant database. The "group characterization" and "two-group comparison" features in the IRBP Toolbox allowed for M-statistical analysis of autoantibody expression. Sorting detectable autoantibodies by difference of prevalence between AD and NDC groups in descending order, the top 10 were selected as potential diagnostic biomarkers.

The selected biomarkers were re-verified as significant by Predictive Analysis for Microarrays (PAM)—an independent algorithm relying on nearest shrunken centroid analysis to identify proteins acting as significant class-differentiators. The predictive classification accuracy of the identified biomarkers was tested with Random Forest (RF) using the default settings, another significance algorithm run as an R package (v 2.12.1). In RF, partitioning trees were built by successively splitting the samples according to a measure of statistical impurity at a given node until terminal nodes are as homogenous as possible. Classification accuracy for a given set of diagnostic biomarkers was reported in a confusion matrix and misclassification as an Out-Of-Bag (OOB) error score.

Results

Protein Microarrays Reveal that Autoantibodies are Numerous in Human Serum

To detect autoantibodies in sera, protein microarrays were probed with individual serum samples (n=149) (Table 9). Results using the standard Chebyshev Inequality p-value threshold of 0.05 suggested an average of over one thousand different autoantibodies per serum sample; although the number varied widely from one individual to the next (n=149, 1115±1096) (Table 10).

TABLE 10

Estimate of Autoantibodies Per Sample Group

| Sample Group | (n) | Median | σ | Range |
|---|---|---|---|---|
| All Samples | 149 | 920 | 1096 | 0-6389 |
| Alzheimer's disease | 50 | 969.25 | 770 | 0-3311 |
| Earlier-stage | 35 | 826.5 | 672 | 0-2805 |
| Later-stage | 15 | 1321.5 | 865 | 110-3311 |
| Non-demented controls | 40 | 982 | 965 | 0-3585 |
| Older Controls | 20 | 1066.25 | 896 | 32-2675 |
| Younger Controls | 20 | 942.5 | 1050 | 0-3585 |
| Parkinson's disease | 29 | 539.5 | 762 | 0-2585 |
| Breast Cancer | 30 | 884.5 | 1723 | 5-6389 |

Selection of Autoantibody Biomarkers for AD Diagnosis

A total of 90 human serum samples (50 AD and 40 NDC) were randomly assigned to either a Training or Testing Set composed of 25 AD and 20 NDC sera each; both containing equal proportions of earlier- and later-stage AD samples as well as older and younger controls. To identify potential diagnostic autoantibodies protein microarrays, each containing 9,486 antigens, were probed with Training Set sera and the data was analyzed as described above. Prospector analysis software determined that 451 autoantibodies had a significantly higher prevalence in the AD group than in the NDC group (p<0.01). The 10 biomarkers that demonstrated the largest difference in group prevalence between AD and NDC were selected to serve as diagnostic indicators. As an independent verification of the 10 biomarkers selected, Predictive Analysis for Microarrays (PAM) was utilized. PAM confirmed that the 10 biomarkers originally selected by Prospector were among the most significant classifiers of AD and NDC. The ten biomarkers are shown in Table 11.

TABLE 11

Identity and Significance of 10 AD vs. NDC Diagnostic Biomarkers

| Database ID | Description | Prevalence in AD | Prevalence in Control | p |
|---|---|---|---|---|
| NM_024754.2 | Pentatricopeptide repeat domain 2 (PTCD2) | 94.23% | 14.29% | 8.03E−14 |
| BC051695.1 | FERM domain containing 8 (FRMD8) | 73.08% | 4.76% | 4.06E−13 |
| NM_018956.2 | Chromosome 9 open reading frame 9 (C9orf9) | 82.69% | 14.29% | 3.30E−09 |
| NM_002305.2 | Lectin, galactoside-binding, soluble, 1 (galectin 1) (LGALS1) | 65.39% | 9.52% | 3.76E−08 |
| NM_000939.1 | Proopiomelanocortin (adrenocorticotropin/beta-lipotropin/alpha-melanocyte stimulating hormone/beta-melanocyte stimulating hormone/beta-endorphin) (POMC), transcript variant 2 | 65.39% | 11.91% | 1.18E−05 |
| NM_003668.2 | Mitogen-activated protein kinase-activated protein kinase 5 (MAPKAPK5), transcript variant 1 | 71.15% | 11.91% | 8.91E−09 |
| BC033758.1 | Centaurin, alpha 2 (CENTA2) | 82.69% | 23.81% | 5.27E−08 |
| NM_014280.1 | DnaJ homolog subfamily C member 8 | 78.85% | 11.91% | 9.49E−12 |
| NM_024668.2 | Ankyrin repeat and KH domain containing 1 (ANKHD1), transcript variant 3 | 73.08% | 14.29% | 1.05E−06 |
| NM_023937.1 | Mitochondrial ribosomal protein L34 (MRPL34), nuclear gene encoding mitochondrial protein | 73.08% | 16.67% | 3.15E−05 |

Verification of Biomarkers Via Training and Testing Set Analyses

To assess the Training and Testing set classification accuracies of the 10 selected biomarkers, Random Forest (RF) was used. RF is a statistical algorithm which creates voting classes of decision-making trees to evaluate the significance of each marker and classify samples and is described by Breiman (2001), *Machine Learning* 45: 5-32. Using the 10 biomarkers to "diagnose" the Training Set (n=45; 25 AD and 20 NDC), RF had an overall accuracy of greater than 93% [Out-of-Bag (OOB) Error 6.67%, a positive predictive value (PPV) of 92.3%, and a negative predictive value (NPV) of 94.7%]. When the 10 biomarkers were used to classify the Testing Set sera (n=45; 25 AD and 20 NDC), which played no part in the biomarker selection process, RF distinguished AD samples from NDCs with a similar accuracy (prediction error of 6.67%, PPV of 100.0%, and NPV of 87.0%).

Biomarker Performance in Different Sample Demographics

When the 10 autoantibody biomarkers were used to classify all AD and NDC samples combined (n=90; 50 AD, 40 NDC) using RF, they did so with a 96.0% sensitivity and 92.5% specificity. Their performance in classifying samples from different demographics: earlier-stage AD, later-stage AD, older controls, and younger controls was also tested. The 10 biomarkers classified samples with over 90% accuracy in all subgroups tested (Table 12). AD samples were correctly differentiated from younger controls with high and consistent accuracy, a common-sense indication of biomarker credibility.

samples from PD samples with over 86% accuracy (sensitivity=90.0%, specificity=79.3%).

TABLE 13

Identity and Significance of Five AD vs. PD Diagnostic Biomarkers

| Database ID | Description | Prevalence in AD | Prevalence in PD | p |
|---|---|---|---|---|
| BC051695.1 | FERM domain containing 8 (FRMD8) | 9.62% | 45.16% | 5.93E−04 |
| NM_003177.3 | Spleen tyrosine kinase (SYK) | 19.23% | 70.97% | 1.35E−05 |
| BC019015.2 | Mediator complex subunit 29 (MED29) | 9.62% | 61.29% | 1.61E−06 |
| BC003551.1 | Transglutaminase 2 (C polypeptide, protein-glutamine-gamma-glutamyltransferase) (TGM2) | 13.46% | 61.29% | 9.67E−05 |
| BC001755.1 | Leiomodin-1 | 26.92% | 70.97% | 6.84E−05 |

Dot Blot Confirmation of Potential Biomarkers

To further validate the differential expression of autoantibodies detected with human protein microarrays, a comparative dot-blot analysis using commercially-obtained, purified native proteins was performed. Two of the most potent differentiating antigens identified, PTCD2 and FRMD8, were selected and their reactivity was verified. The two proteins were spotted onto nitrocellulose membrane and

TABLE 12

Diagnostic Accuracies of Selected Biomarkers

| | AD (n = 50) vs. | | | | Earlier-stage AD (n = 35) vs. | | Later-stage AD (n = 15) vs. | |
|---|---|---|---|---|---|---|---|---|
| | All NDC n = 40 | Older Control n = 20 | Younger Control n = 20 | PD* n = 29 | Breast Cancer n = 30 | All NDC n = 40 | Older Control n = 20 | All NDC n = 40 | Older Control n = 20 |
| Sensitivity % | 96.0 | 98.0 | 98.0 | 90.0 | 98.0 | 97.1 | 97.1 | 86.7 | 93.3 |
| Specificity % | 92.5 | 85.0 | 90.0 | 79.3 | 83.0 | 92.5 | 90.0 | 97.5 | 90 |
| PPV % | 94.1 | 94.2 | 96.1 | 88.2 | 90.7 | 91.9 | 94.4 | 92.9 | 87.5 |
| NPV % | 94.9 | 94.4 | 94.7 | 82.1 | 96.2 | 97.4 | 94.7 | 95.1 | 94.7 |

*The biomarkers used for this classification are those of Table 13; all others are the biomarkers identified in Table 11.

Distinction of AD from Other Diseases

The ability of the biomarker diagnostic to differentiate AD from other non-neurological and neurological diseases was assessed. 30 breast cancer serum samples were acquired and the 10 selected diagnostic biomarkers were used to differentiate them from the 50 AD samples. RF reported an OOB Error of 7.5% (PPV and NPV of 90.7% and 96.2%, respectively). These results are similar to those of the AD versus NDC trials above and demonstrate no diagnostic bias toward general disease.

The ability of the biomarker diagnostic to differentiate between two closely related neurodegenerative diseases was also assessed. For this, Parkinson's disease (PD) was selected because it shares much in common with Alzheimer's pathology. There is also a significant overlap (22%~48%) at the pathological and clinical levels, making it difficult to clearly distinguish these two diseases by conventional means alone. Again, Prospector, PAM, and RF were utilized to identify the most significant disease classifiers. It was determined that by using only five diagnostic biomarkers (Table 13), it was possible to differentiate AD probed with identical sera to that used on the microarrays. Results from both AD and NDC sera show strong agreement in the relative intensities of the immunoreaction in protein microarrays and dot blots. The majority of AD sera reacted intensely to purified PTCD2 and FRMD8 protein, while most control sera showed a weak or no reaction. Dot blot assays independently confirmed that anti-FRMD8 and anti-PTCD2 antibodies were more predominant in AD sera than in NDC sera.

All references cited herein are incorporated by reference herein in their entireties.

What is claimed is:

1. A kit for detecting Alzheimer's disease (AD) diagnostic biomarkers in a subject's biological sample, the kit comprising:
   (a) an ordered microarray comprising a substrate and autoantigens immobilized onto said substrate, wherein the only autoantigens in the microarray are the following:
      a first group of autoantigens consisting of Pentatricopeptide repeat domain 2 (PTCD2); FERM domain containing 8 (FRMD8); Chromosome 9 open reading frame 9 (C9orf9); Lectin, galactoside-binding, soluble, 1 (galectin 1) (LGALS1); Proopiomelanocortin (adrenocorticotropin/beta-lipotropin/alpha-melanocyte stimulating hormone/beta-melanocyte stimulating hormone/beta-endorphin) (POMC), transcript variant 2; Mitogen-activated protein kinase-activated protein kinase 5 (MAPKAPK5), transcript variant 1; Centaurin, alpha 2 (CENTA2); DnaJ homolog subfamily C member 8; Ankyrin repeat and KH domain containing 1 (ANKHD1), transcript variant 3; Mitochondrial ribosomal protein L34 (MRPL34), and nuclear gene encoding mitochondrial protein; and a second group of two or more autoantigens selected from the group consisting of hematopoietic SH2 domain containing (HSH2D); proteins corresponding to cDNA clone MGC:27152 IMAGE:4691630, complete cds; cDNA clone MGC:31944 IMAGE: 4878869, complete cds; and cDNA clone MGC: 32654 IMAGE:4701898, complete cds;

(b) assay reagents for label-based detection of at least three immunocomplexes formed by binding of the immobilized autoantigens of (a) to the AD diagnostic biomarkers in an immunoglobulin-containing biological sample from a subject; and (c) a package labeling indicating a diagnosis of AD in said subject upon detecting:

1) formation of at least one immunocomplex from said first group of autoantigens: Pentatricopeptide repeat domain 2 (PTCD2); FERM domain containing 8 (FRMD8); Chromosome 9 open reading frame 9 (C9orf9); Lectin, galactoside-binding, soluble, 1 (galectin 1) (LGALS1); Proopiomelanocortin (adrenocorticotropin/beta-lipotropin/alpha-melanocyte stimulating hormone/beta-melanocyte stimulating hormone/beta-endorphin) (POMC), transcript variant 2; Mitogen-activated protein kinase-activated protein kinase 5 (MAPKAPK5), transcript variant 1; Centaurin, alpha 2 (CENTA2); DnaJ homolog subfamily C member 8; Ankyrin repeat and KH domain containing 1 (ANKHD1), transcript variant 3; Mitochondrial ribosomal protein L34 (MRPL34), and nuclear gene encoding mitochondrial protein; and 2) formation of two or more immunocomplexes from said second group of autoantigens: hematopoietic SH2 domain containing (HSH2D); proteins corresponding to cDNA clone MGC:27152 IMAGE: 4691630, complete cds; cDNA clone MGC:31944 IMAGE:4878869, complete cds; and cDNA clone MGC:32654 IMAGE:4701898, complete cds.

2. The kit of claim 1, wherein two or more autoantigens from said second group are selected from the group consisting of cDNA clone MGC:31944 IMAGE:4878869, complete cds; hematopoietic SH2 domain containing (HSH2D); and cDNA clone MGC:32654 IMAGE:4701898, complete cds.

3. The kit of claim 1, wherein said package labeling indicates a diagnosis of AD upon positive detection of immunocomplexes from FERM domain containing 8 (FRMD8) and at least two autoantigens selected from the group consisting of cDNA clone MGC:31944 IMAGE: 4878869, complete cds; hematopoietic SH2 domain containing (HSH2D); and cDNA clone MGC:32654 IMAGE: 4701898, complete cds in said biological sample.

4. The kit of claim 1, wherein said package labeling indicates a diagnosis of AD upon positive detection of immunocomplexes from FERM domain containing 8 (FRMD8); cDNA clone MGC:31944 IMAGE:4878869, complete cds; hematopoietic SH2 domain containing (HSH2D); and cDNA clone MGC:32654 IMAGE:4701898, complete cds in said biological sample.

5. The kit of claim 1, wherein said package labeling indicates a diagnosis of AD upon positive detection of immunocomplexes from at least five autoantigens from said first group of autoantigens in said biological sample.

6. The kit of claim 1, wherein said package labeling indicates a diagnosis of AD upon positive detection of immunocomplexes from ten autoantigens from said first group of autoantigens in said biological sample.

* * * * *